(12) United States Patent
Daggett et al.

(10) Patent No.: US 9,896,487 B2
(45) Date of Patent: Feb. 20, 2018

(54) AMYLOIDOSIS-INHIBITING POLYPEPTIDES AND THEIR USE

(71) Applicant: UNIVERSITY OF WASHINGTON THROUGH ITS CENTER FOR COMMERCIALIZATION, Seattle, WA (US)

(72) Inventors: Valerie Daggett, Mercer Island, WA (US); Gene Hopping, Seattle, WA (US)

(73) Assignee: University of Washington Through Its Center For Commercialization, Seattle, WA (US)

( * ) Notice: Subject to any disclaimer, the term of this patent is extended or adjusted under 35 U.S.C. 154(b) by 0 days.

(21) Appl. No.: 14/775,272

(22) PCT Filed: Mar. 13, 2014

(86) PCT No.: PCT/US2014/025492
§ 371 (c)(1),
(2) Date: Sep. 11, 2015

(87) PCT Pub. No.: WO2014/159941
PCT Pub. Date: Oct. 2, 2014

(65) Prior Publication Data
US 2016/0031952 A1    Feb. 4, 2016

Related U.S. Application Data

(60) Provisional application No. 61/785,356, filed on Mar. 14, 2013.

(51) Int. Cl.
| | | |
|---|---|---|
| *A61K 38/03* | (2006.01) | |
| *A61K 38/10* | (2006.01) | |
| *A61K 38/16* | (2006.01) | |
| *C07K 4/00* | (2006.01) | |
| *C07K 7/08* | (2006.01) | |
| *C07K 14/00* | (2006.01) | |
| *C07K 14/435* | (2006.01) | |
| *G01N 33/68* | (2006.01) | |
| *C07K 14/47* | (2006.01) | |
| *C07K 7/06* | (2006.01) | |
| *A61K 38/00* | (2006.01) | |

(52) U.S. Cl.
CPC ........... *C07K 14/435* (2013.01); *A61K 38/03* (2013.01); *A61K 38/10* (2013.01); *A61K 38/16* (2013.01); *C07K 4/00* (2013.01); *C07K 7/06* (2013.01); *C07K 7/08* (2013.01); *C07K 14/00* (2013.01); *C07K 14/4711* (2013.01); *G01N 33/6893* (2013.01); *G01N 33/6896* (2013.01); *A61K 38/00* (2013.01); *G01N 2800/2821* (2013.01); *G01N 2800/2828* (2013.01); *G01N 2800/709* (2013.01)

(58) Field of Classification Search
CPC ........ A61K 38/03; A61K 38/10; A61K 38/16; C07K 4/00; C07K 7/08; C07K 14/00
See application file for complete search history.

(56) References Cited

U.S. PATENT DOCUMENTS

| | | | |
|---|---|---|---|
| 7,745,574 B2 | 6/2010 | Satterthwait et al. | |
| 8,242,241 B2 | 8/2012 | Daggett et al. | |
| 2004/0214272 A1 | 10/2004 | La Rosa et al. | |
| 2009/0076244 A1* | 3/2009 | Kulp .................... | C07K 14/001 530/317 |
| 2012/0283409 A1 | 11/2012 | Daggett et al. | |

FOREIGN PATENT DOCUMENTS

| | | |
|---|---|---|
| EP | 2123668 A1 | 11/2009 |
| EP | 2972388 | 1/2016 |
| WO | 2009120371 A2 | 10/2009 |
| WO | 2014159941 A1 | 10/2014 |

OTHER PUBLICATIONS

Armen et al., "Characterization of a possible amyloidogenic precursor in glutamine-repeat neurodegenerative diseases," Proceedings of the National Academy of Sciences USA, vol. 102, No. 38, pp. 13433-13438, 2005.
Armen et al., "Characterization of two distinct beta2-microglobulin unfolding intermediates that may lead to amyloid fibrils of different morphology," Biochemistry, vol. 44, No. 49, pp. 16098-16107, 2005.
Armen, et al., "Anatomy of an amyloidogenic intermediate: conversion of beta-sheet to alpha-sheet structure in transthyretin at acidic pH," Structure, vol. 12, No. 10, pp. 1847-1863, 2004.
Armen, et al., "Pauling and Corey's alpha-pleated sheet structure may define the prefibrillar amyloidogenic intermediate in amyloid disease," Proceedings of the National Academy of Sciences USA, vol. 101, No. 32, pp. 11622-11627, 2004.
Barth, et al., "What vibrations tell us about proteins," Quarterly Reviews of Biophysics, vol. 35, No. 4, pp. 369-430, 2002.
Beck, et al., "In lucem molecular mechanics (ilmm)," Computer Program, University of Washington—information available at: http://depts.washington.edu/daglab/ilmm.html , 2013.
Beck, et al., "Methods for molecular dynamics simulations of protein folding/unfolding in solution," Methods, 34 (1):112-120, 2004.
Beck, et al., "The intrinsic conformational propensities of the 20 naturally occurring amino acids and reflection of these propensities in proteins," Proceedings of the National Academy of Sciences USA, vol. 105, No. 34, pp. 12259-12264, 2008.
Bitan, et al., "Neurotoxic protein oligomers—what you see is not always what you get," Amyloid, vol. 12, No. 2, pp. 88-95, 2005.
Bodner, et al., "Pharmacological promotion of inclusion formation: a therapeutic approach for Huntington's and Parkinson's diseases," Proceedings of the National Academy of Sciences USA, vol. 103, No. 11, pp. 4246-4251, 2006.

(Continued)

*Primary Examiner* — Jeffrey E. Russel
(74) *Attorney, Agent, or Firm* — McDonnell Boehnen Hulbert & Berghoff LLP

(57) ABSTRACT

Isolated polypeptides that possess an a-sheet structure are disclosed that can be used to treat or diagnose amyloid diseases.

21 Claims, 11 Drawing Sheets

(56) References Cited

OTHER PUBLICATIONS

Bucciantini et al., "Inherent toxicity of aggregates implies a common mechanism for protein misfolding diseases," Nature, vol. 416, No. 6880, pp. 507-511, 2002.
Bunkoczi, et al., "The Antiviral Antibiotic Feglymycin: First Direct-Methods Solution of a 1000+ Equal-Atom Structure," Angewandte Chemie International Edition, vol. 44, No. 9, pp. 1340-1342, 2005.
Carulla, et al., "Experimental characterization of disordered and ordered aggregates populated during the process of amyloid fibril formation," Proceedings of the National Academy of Sciences USA, vol. 106, No. 19, pp. 7828-7833, 2009.
Chiti, et al., "Amyloid formation by globular proteins under native conditions," Nature Chemical Biology, vol. 5, No. 1, pp. 15-22, 2009.
Clark, et al., "Engineering stable peptide toxins by means of backbone cyclization: stabilization of the alpha-conotoxin MII," Proceedings of the National Academy of Sciences USA, vol. 102, No. 39, pp. 13767-13772, 2005.
Cochran, et al., "A minimal peptide scaffold for beta-turn display: optimizing a strand position in disulfide-cyclized beta-hairpins," Journal of the American Chemical Society, vol. 123, No. 4, pp. 625-632, 2001.
Cochran, et al., "Tryptophan zippers: stable, monomeric beta-hairpins," Proceedings of the National Academy of Sciences USA, vol. 98, No. 10, pp. 5578-5583, 2001.
Colon, et al., "Partial denaturation of transthyretin is sufficient for amyloid fibril formation in vitro," Biochemistry, vol. 31, No. 36, pp. 8654-8660, 1992.
Daggett, "Alpha-sheet: The toxic conformer in amyloid diseases?" Accounts of Chemical Research, vol. 39, No. 9, pp. 594-602, 2006.
De Santis, et al., "Conformational Analysis of Regular Enantiomeric Sequences," Macromolecules, vol. 7, No. 1, pp. 52-58, 1974.
DeMarco et al., "Structural properties of prior protofibrils and fibrils: an experimental assessment of atomic models," Biochemistry, vol. 45, No. 51, pp. 15573-15582, 2006.
Di Blasio, et al., "A crystal structure with features of an antiparallel alpha-pleated sheet," Biopolymers, vol. 34, No. 11, pp. 1463-1468, 1994.
Du, et al., "Characterization of the interaction of β-amyloid with transthyretin monomers and tetramers," Biochemistry, vol. 49, No. 38, pp. 8276-8289, 2010.
Foss, et al., "The pathway by which the tetrameric protein transthyretin dissociates," Biochemistry, vol. 44, No. 47, pp. 15525-15533, 2005.
Glabe, et al., "Common structure and toxic function of amyloid oligomers implies a common mechanism of pathogenesis," Neurology, vol. 66, 2 Suppl 1, pp. S74-S78, 2006.
Härd, et al., "Inhibition of amyloid formation," Journal of Molecular Biology, vol. 421, No. 4-5, pp. 441-465, 2012.
Hardy, et al., "The amyloid hypothesis of Alzheimer's disease: progress and problems on the road to therapeutics," Science, vol. 297, No. 5580, pp. 353-356, 2002.
Heitz, et al., "Sheet structures in alternating poly(D,L-peptides)," Macromolecules, vol. 14, No. 1, pp. 47-50, 1981.
Jahn, et al., "The Common Architecture of Cross-Beta Amyloid," Journal of Molecular Biology, vol. 395, No. 4, pp. 717-727, 2010.
Kayed, et al., "Common structure of soluble amyloid oligomers implies common mechanism of pathogenesis," Science, vol. 300, No. 5618, pp. 486-489, 2003.
Klunk et al. (Aug. 1989) "Two simple methods for quantifying low-affinity dye-substrate binding," Journal of Histochemistry and Cytochemistry, vol. 37, No. 8, pp. 1293-1297.
Koeppe, et al., "On the helix sense of gramicidin A single channels," Proteins, vol. 12, No. 1, pp. 49-62, 1992.
Lelievre, et al., "Synthesis and characterization of retro gramicidin A-dAla-gramicidin A, a 31-residue-long gramicidin analogue," International Journal of Peptide and Protein Research, vol. 33, No. 5, pp. 379-385, 1989.
Levitt, et al., "Calibration and Testing of a Water Model for Simulation of the Molecular Dynamics of Proteins and Nucleic Acids in Solution," Journal of Physical Chemistry B, vol. 101, No. 25, pp. 5051-5061, 1997.
Levitt, et al., "Potential energy function and parameters for simulations of the molecular dynamics of proteins and nucleic acids in solution," Computer Physics Communications, vol. 91, No. 1-3, pp. 215-231, 1995.
Pauling, et al., "The pleated sheet, a new layer configuration of polypeptide chains," Proceedings of the National Academy of Sciences USA, vol. 37, No. 5, pp. 251-256, 1951.
PCT/US2009/001925 International Search Report and Written Opinion, dated 2009.
PCT/US2014/025492, International Search Report and Written Opinion, dated 2014.
Quintas, et al., "The amyloidogenic potential of transthyretin variants correlates with their tendency to aggregate in solution," FEBS Letters, vol. 418, No. 3, pp. 297-300, 1997.
Reixach, et al., "Tissue damage in the amyloidoses: Transthyretin monomers and nonnative oligomers are the major cytotoxic species in tissue culture," Proceedings of the National Academy of Sciences USA, vol. 101, No. 9, pp. 2817-2822, 2004.
Schoch, et al., "Conformational characteristics of alternating stereo-co-oligopeptides of D- and L-norleucine: influence of an N-methyl group," International Journal of Peptide and Protein Research, vol. 44, No. 1, pp. 10-18, 1994.
Silveira, et al., "The most infectious prion protein particles," Nature, vol. 437, No. 7056, pp. 257-261, 2005.
Steward, et al., "Different disease-causing mutations in transthyretin trigger the same conformational conversion," Protein Engineering Design and Selection, vol. 21, No. 3, pp. 187-195, 2008.
Tomic et al., "Soluble fibrillar oligomer levels are elevated in Alzheimer's disease brain and correlate with cognitive dysfunction," Neurobiology of Disease, vol. 35, No. 3, pp. 352-358, 2009.
Torii, "Amide I infrared spectral features characteristic of some untypical conformations appearing in the structures suggested for amyloids," Journal of Physical Chemistry B, vol. 112, No. 29, pp. 8737-874, 2008.
van der Kamp, et al., "Dynameomics: a comprehensive database of protein dynamics," Structure, vol. 18, No. 4, pp. 423-435, 2010.
Wüthrich, "Chapter 9: Polypeptide Secondary Structures in Proteins by NMR," in NMR of Proteins and Nucleic Acids, pp. 162-175, 1986.
Xue et al., "Fibril fragmentation enhances amyloid cytotoxicity," Journal of Biological Chemistry, vol. 284, No. 49, pp. 34272-34282, 2009.
Yamin, et al., "A peptide hairpin inhibitor of amyloid beta-protein oligomerization and fibrillogenesis," Biochemistry, vol. 48, No. 48, pp. 11329-11331, 2009.

* cited by examiner

FIGURE 5

(top to bottom: SEQ ID NO: 38, 92, 104, 106, 31, 91, 38, 108, 74, 150, 89, 91, 90, 113, 154, 155, 156, 157, 147, 38)

AMYLOIDOSIS-INHIBITING POLYPEPTIDES AND THEIR USE

CROSS-REFERENCE

This application is a U.S. National Phase of International Application No. PCT/US2014/025492, filed Mar. 13, 2014, which claims priority to U.S. Application No. 61/785,356, filed Mar. 14, 2013, the disclosures of which are hereby incorporated by reference in their entireties.

STATEMENT OF GOVERNMENT SUPPORT

This invention was made with government support under Grant No. R01 GM050789 awarded by the National Institutes of Health, and Grant No. CBET-0966977 awarded by the National Science Foundation. The government has certain rights in the invention.

BACKGROUND

There are now over 40 different human amyloid diseases, each linked to the buildup of a specific precursor protein or peptide. These diseases involve the conversion of a protein from its soluble native state into insoluble amyloid fibrils, or, in the case of peptides, the conversion from a soluble, loosely structured form to fibrils. Given that many different sequences can form amyloid fibrils of similar architecture, there may be some common structural features of the prefibrillar amyloidogenic intermediates. X-ray fiber diffraction indicates that the insoluble, mature amyloid fibrils are composed of cross β-sheet structure. Therefore, it is widely held that the formation of amyloid fibrils involves a transition to β-sheet structure in the amyloidogenic intermediate. However, the mechanism of self-assembly at the atomic level remains elusive. Another feature of these diseases is that soluble oligomeric intermediates, not the insoluble well-ordered fibrils, are preferentially responsible for cellular toxicity. Similarly, the soluble oligomeric forms of the prion protein are the most infectious per unit protein. As such, fibrils may be protective, at least up to a point, as their breakdown to smaller aggregates yields greater toxicity and infectivity.

SUMMARY OF THE INVENTION

In a first aspect, the invention provides isolated polypeptides, comprising or consisting of 12-23 contiguous amino acids according to the general formula X1-X2-X3-X4-X5 (SEQ ID NO: 1), wherein X1 is 0-7 contiguous amino acid residues that do not alternate between L and D residues;

X2 is 5-9 contiguous amino acid residues alternating between D amino acids and L amino acids;

X3 is 0-5 contiguous amino acid residues that do not alternate between L and D residues;

X4 is 4-12 contiguous amino acid residues alternating between D amino acids and L amino acids; and X5 is 0-4 contiguous amino acid residues that do not alternate between L and D residues;

wherein the isolated polypeptide is not:

(SEQ ID NO: 2)
RGE(m)N(l)S(w)MNEYSGW(t)M(n)L(k)MGR.

In one embodiment, X1 is 0-2 contiguous amino acid residues that do not alternate between L and D residue. In another embodiment, all X1 amino acid residues are L amino acids. In a further embodiment, X2 is 6-8 contiguous amino acid residues alternating between D amino acids and L amino acids. In another embodiment, X3 is 1-5 contiguous amino acid residues that do not alternate between L and D residues. In a further embodiment, all X3 amino acids are L amino acids. In various other embodiments X4 is 6-12 contiguous amino acid residues alternating between D amino acids and L amino acids; X5 is 0-3 contiguous amino acid residues that do not alternate between L and D residues; and all X5 amino acids are L amino acids.

In one embodiment. X1 is absent; X2 is 5-7 contiguous amino acid residues alternating between D amino acids and L amino acids; X3 is 0-3 contiguous amino acid residues that do not alternate between L and D residues; X4 is 6-11 contiguous amino acid residues alternating between D amino acids and L amino acids; and X5 is 0 or 1 amino acid residue.

In another embodiment, X1 is absent; X2 is 7 contiguous amino acid residues alternating between D amino acids and L amino acids; X3 is 3 contiguous amino acid residues that do not alternate between L and D residues; X4 is 9 contiguous amino acid residues alternating between D amino acids and L amino acids; and X5 is absent.

In a further embodiment, X1 is absent; X2 is 8 contiguous amino acid residues alternating between D amino acids and L amino acids; X3 is 3 contiguous amino acid residues that do not alternate between L and D residues; X4 is 10 contiguous amino acid residues alternating between D amino acids and L amino acids; and X5 is absent.

In a still further embodiment, X1 is 2 contiguous amino acid residues that do not alternate between L amino acids and D amino acids; X7 is 7 contiguous amino acid residues alternating between D amino acids and L amino acids; X3 is 3 contiguous amino acid residues that do not alternate between L and D residues; X4 is 9 contiguous amino acid residues alternating between D amino acids and L amino acids; and X5 is 2 contiguous amino acid residues that do not alternate between L amino acids and D amino acids.

In another embodiment, X1 is absent; X7 is 7 contiguous amino acid residues alternating between D amino acids and L amino acids; X3 is 4 contiguous amino acid residues that do not alternate between L and D residues; X4 is 8 contiguous amino acid residues alternating between D amino acids and L amino acids; and X5 is absent.

In one embodiment, X1 is absent; X7 is 7 contiguous amino acid residues alternating between D amino acids and L amino acids; X3 is 1 contiguous amino acid residues that do not alternate between L and D residues; X4 is 4 contiguous amino acid residues alternating between D amino acids and L amino acids; and X5 is absent.

In a further embodiment, X1 is absent; X2 is 7 contiguous amino acid residues alternating between D amino acids and L amino acids; X3 is 5 contiguous amino acid residues that do not alternate between L and D residues; X4 is 7 contiguous amino acid residues alternating between D amino acids and L amino acids; and X5 is absent.

In another embodiment, X1 is absent; X2 is 6 contiguous amino acid residues alternating between D amino acids and L amino acids; X3 is 3 contiguous amino acid residues that do not alternate between L and D residues; X4 is 1 contiguous amino acid residues alternating between D amino acids and L amino acids; and X5 is 1 amino acid residue.

In a still further embodiment, X1 is absent; X2 is 7 contiguous amino acid residues alternating between D amino acids and L amino acids; X3 is 1 amino acid residue that do not alternate between L and D residues; X4 is 6 contiguous amino acid residues alternating between D amino acids and L amino acids; and X5 is absent.

In one embodiment, X1 is absent; X2 is 6 contiguous amino acid residues alternating between D amino acids and L amino acids; X3 is 3 contiguous amino acid residues that do not alternate between L and D residues; X4 is 10 contiguous amino acid residues alternating between D amino acids and L amino acids; and X5 is 1 amino acid residue.

In another embodiment, X1 is absent; X2 is 8 contiguous amino acid residues alternating between D amino acids and L amino acids; X3 is 3 contiguous amino acid residues that do not alternate between L and D residues; X4 is 12 contiguous amino acid residues alternating between D amino acids and L amino acids; and X5 is absent.

In various embodiments, the polypeptide comprises or consists of 14-23, 17-23, or 21-23 contiguous amino acids according to the recited formula.

In another aspect, the invention provides pharmaceutical compositions, comprising:

(a) the isolated polypeptide of any embodiment or combination of embodiments of the invention; and (b) a pharmaceutically acceptable carrier.

In a further aspect, the invention provides methods for treating an amyloid disease, comprising administering to a subject with an amyloid disease an amount effective of the isolated polypeptide of any embodiment or combination of embodiments of the invention, or the pharmaceutical composition of the invention to treat the amyloid disease. In various embodiments, the amyloid disease may be selected from the group consisting of Creutzfeldt-Jakob disease, spongiform encephalopathy, Huntington's disease, amyotrophic lateral sclerosis (ALS), senile systemic amyloidosis, familial amyloid polyneuropathy. Kennedy disease, Machado-Joseph disease, Alzheimer's disease, bovine spongiform encephalopathy, scrapie, type 2 diabetes, amyloidosis caused by transthyretin (ATTR), Parkinson's disease, atherosclerosis, rheumatoid arthritis, aortic medial amyloid, prolactinomas, dialysis-related amyloidosis, cerebral amyloid angiopathy, Finnish amyloidosis, lattice corneal dystrophy, and multiple myeloma.

In another aspect, the invention provides methods for diagnosing or prognosing an amyloid disease, comprising (a) contacting a tissue sample from a subject at risk of having an amyloid disease with the isolated polypeptide of any embodiment of the invention, or a pharmaceutical composition of the invention, under conditions suitable for binding of the isolated polypeptide with an amyloid intermediate, if present in the tissue sample, to produce a binding complex;

(b) detecting binding complexes in the tissue sample; and (c) diagnosing or prognosing an amyloid disease based on the detecting.

In various embodiments, the tissue sample may be a blood sample, serum sample, nasal secretions, urine or a cerebral spinal fluid sample.

DESCRIPTION OF THE FIGURES

FIG. 5. Table showing properties of designed peptides. (Sequence identifiers corresponding to peptides 1-14, 16-21, from top to bottom: SEQ ID NO: 38, 92, 104, 106, 31, 91, 38, 108, 74, 150, 89, 91, 90, 113, 154, 155, 156, 157, 147, 38.)

DETAILED DESCRIPTION OF THE INVENTION

Figure 1:
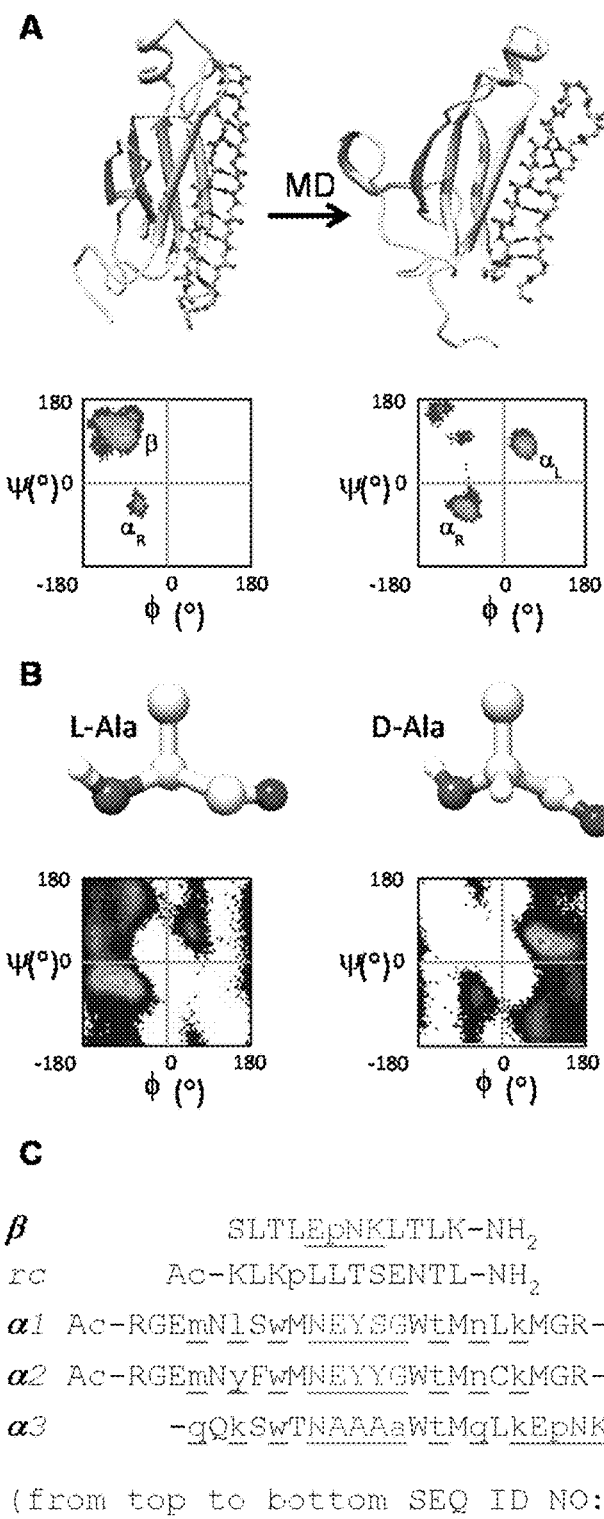
FIG. 1. α-sheet conversion, conformational properties and peptide designs. (A) β- to α-sheet conversion of transthyretin (TTR), which is implicated in systemic amyloidosis and familial peripheral polyneuropathy, as reported by Armen and co-workers (11, 13). The protein backbone is shown in cartoon representation with the region of interest (residues 105-121) shown as sticks. At 0 ns (top left) the residues of interest form a β-hairpin. The dihedral angles for 1 ns of dynamics of these residues are found mainly in the β-region of the Ramachandran plot (top left quadrant, lower left panel; increasing frequency of occupancy is shown from blue through red) with several turn residues in the $\alpha_R$ conformation (bottom left quadrant). After 30 ns (top right) the β-sheet has converted to an α-sheet. The dihedral angles for 1 ns of dynamics of the same residues reveal that the majority of residues have moved from the β-region to the $\alpha_L$ (top right quadrant) or $\alpha_R$ region of the Ramachandran plot (lower right panel). (B) Intrinsic residue propensities for L- and D-alanine were calculated from 100 ns of MD simulations of a GGXGG (SEQ ID NO: 3) peptide system (18) (D-alanine was simulated using the same protocol). The backbone structure (upper panels) as well as the Ramachandran plot of the conformation of the alanine residue during the entire simulation, demonstrate the conformational preference for L-alanine to adopt the $\alpha_R$ conformation and for D-alanine to favor the $\alpha_L$ conformation (lower panels). (C) Peptide designs reported in Example 1. Designs are linear single turn hairpins or closed cyclic hairpins, i.e., a cyclic peptide backbone resulting in two turns, as illustrated by α3. Hairpin peptides are N- and C-terminally acetylated and amidated, respectively, except for β, which had a free N-terminus. D-amino acids are denoted by lower case and underlined, and turn residues are identified in red and blue.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego. Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*. 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments of any aspect of the invention can be used in combination, unless the context clearly dictates otherwise.

In a first aspect, the present invention provides isolated polypeptides, comprising or consisting of 12-23 contiguous amino acids according to the general formula 1 X1-X2-X3-X4-X5 (SEQ ID NO: 1), wherein X1 is 0-7 contiguous amino acid residues that do not alternate between L amino acids and D amino acids;

X2 is 5-9 contiguous amino acid residues alternating between D amino acids and L amino acids;

X3 is 0-5 contiguous amino acid residues that do not alternate between L amino acids and D amino acids;

X4 is 4-12 contiguous amino acid residues alternating between D amino acids and L amino acids; and X5 is 0-4 contiguous amino acid residues that do not alternate between L amino acids and D amino acids;

wherein the isolated polypeptide is not:

(SEQ ID NO: 2)
RGE(m)N(l)S(w)MNEYSGW(t)M(n)L(k)MGR.

In the various general formulae and sequences disclosed herein, amino acid residues recited in the uppercase and not within parentheses are in the "L" configuration ("L amino acids"), while those in lower case and within parentheses are in the 'D" configuration ("D amino acids"). In the individual polypeptide sequences provided herein, amino acid residues in uppercase are L amino acids, while amino acid residues in lowercase are D amino acids.

As is disclosed in detail below, the inventors have discovered that the polypeptides of the invention adopt an α-sheet structure, regardless of the primary amino acid sequence and thus can be used, for example, in the therapeutic and diagnostic methods of the invention described herein. As demonstrated herein, the polypeptides of the invention are useful for inhibiting aggregation and/or binding of the toxic oligomeric form of amyloidogenic intermediates. As further demonstrated herein, the primary amino acid sequence of the polypeptides does not per se dictate the inhibitory activity (here defined as inhibition of aggregation and/or binding of toxic oligomer). Instead it is the ability of the polypeptides to adopt a stable α-sheet structure that is operative here, and that is achieved through the recited polypeptide generic structure and the recited arrangement of alternating D/L amino acids. As demonstrated herein, random primary sequences of amino acids are active in the polypeptides of the invention. These same primary sequences are not active if the polypeptide is composed entirely of L-amino acids or if the L/D amino acids are randomly distributed within the polypeptide such that they are not alternating. The primary amino acid sequence of the polypeptides does however modulate the stability, solubility and degree of activity of the polypeptide.

As used throughout the present application, the term "polypeptide" is used in its broadest sense to refer to a sequence of subunit amino acids. The polypeptides of the invention comprise regions of alternating L-amino acids and D-amino acids. "L amino acids" are L-steroisomers (left-handed isomers), while 'D amino acids" are D steroisomers (right-handed isomers), as is known to those of skill in the art. The amino acids may be any of the naturally occurring L- or D-amino acids, analogues thereof, or may be any non-natural or uncoded amino acids. Exemplary non-natural/uncoded amino acids include, but are not limited to aminoisobuteric acid, cyclohexylalanine, naphthylalanine, norvaline, norleucine, aminoheptanoic acid, aminoctanoic acid, and selenomethionine. Those of skill in the art are well aware that many such non-natural/uncoded amino acids exist, and it is well within the level of skill in the art to use such non-natural/uncoded amino acids in the polypeptides of the invention, based on the teachings herein.

As used herein, "alternating" means a stretch of at least 3 amino acids that alternate between L isomers and D isomers (i.e., L-D-L; D-L-D; etc.)

As used herein, "do not alternate between L and D residues" means that the region does not include a stretch of at least 3 amino acids that alternate between L isomers and D isomers. Such regions (X1, X3, and X5) may thus include both D and L residues. For example, the polypeptide eLkSwTNAAAaWtMqLIDpNR (SEQ ID NO: 4) (amino acid residues in uppercase are L amino acids, while amino acid residues in lowercase are D amino acids) has the following subunit structure according to the present invention:

X1 is 0 contiguous amino acid residues that do not alternate between L amino acids and D amino acids;

X2 is 6 contiguous amino acid residues alternating between D amino acids and L amino acids (eLkSwT) (SEQ ID NO: 5);

X3 is 3 contiguous amino acid residues that do not alternate between L amino acids and D amino acids (NAA);

X4 is 11 contiguous amino acid residues alternating between D amino acids and L amino acids (AaWtMqLIDpN) (SEQ ID NO: 6); and X5 is 1 amino acid residue that does not alternate between L amino acids and D amino acids (R).

In another example, the polypeptide RGEmNISwMNEYSNWtMnLkMGR (SEQ ID NO: 7) (amino acid residues in uppercase are L amino acids, while amino acid residues in lowercase are D amino acids) has the following subunit structure according to the present invention:

X1 is 2 contiguous amino acid residues that do not alternate between L amino acids and D amino acids (RG);

X2 is 7 contiguous amino acid residues alternating between D amino acids and L amino acids (EmNISwM) (SEQ ID NO: 8);

X3 is 5 contiguous amino acid residues that do not alternate between L amino acids and D amino acids (NEYSN) (SEQ ID NO: 9);

X4 is 7 contiguous amino acid residues alternating between D amino acids and L amino acids (WtMnLkM) (SEQ ID NO: 10); and X5 is 2 contiguous amino acid residues that do not alternate between L amino acids and D amino acids (GR).

Those of skill in the art will recognize how other polypeptides sequences fit within the various general formulae described herein. The polypeptides described herein may be chemically synthesized using standard techniques.

In various embodiments, X1 is 0-6, 0-5, 0-4, 0-3, or 0-2 contiguous amino acid residues that do not alternate between L and D residues. In other embodiments, X1 is 1 amino acid or is absent. In a further embodiment of any of these embodiments, all X1 amino acid residues are L amino acids.

In various embodiments, X2 is 5-8, 5-7, 6-9, 6-8, 6-7, 5, 6, 7, 8, or 9 contiguous amino acid residues alternating between D amino acids and L amino acids.

In various further embodiment X3 is 0-4, 0-3, 0-2, 1-5, 1-4, 1-3, 1-2, 2-5, 2-4, 2-3, 3-5, 3-4, 4-5, 5, 4, 3, or 2 contiguous amino acid residues that do not alternate between L and D residues. In various further embodiments, X3 is a single amino acid residue or is absent. In a further embodiment of any of these embodiments, all X3 amino acids are L amino acids.

In various embodiments, X4 is 4-11, 4-10, 4-9, 4-8, 4-7, 4-6, 4-5, 5-12, 5-11, 5-10, 5-9, 5-8, 5-7, 5-6, 6-12, 6-11, 6-10, 6-9, 6-8, 6-7, 7-12, 7-11, 7-10, 7-9, 7-8, 8-12, 8-11, 8-10, 8-9, 9-12, 9-11, 9-10, 10-12, 10-11, 11-12, 12, 11, 10, 9, 8, 7, 6, 5, or 4 contiguous amino acid residues alternating between D amino acids and L amino acids.

In various embodiments, X5 is 0-3, 0-2, 1-4, 1-3, 1-2, 2-4, 2-3, 3-4, 4, 3, or 2 contiguous amino acid residues that do not alternate between L and D residues. In a further embodiment of any of these embodiments, all X5 amino acids are L amino acids.

In various further embodiments, at least one of the following (i.e.: 1, 2, 3, 4, or all 5) is/are true about polypeptides according to general formula 1:

(a) X1 is 0 or 1 amino acid;
(b) X2 is 5, 6, 8, or 9 contiguous amino acid residues alternating between D amino acids and L amino acids;
(c) X3 is 0-4 contiguous amino acid residues that do not alternate between L and D residues;
(d) X4 is 6, 8, 9, 10, 11, or 12 contiguous amino acid residues alternating between D amino acids and L amino acids; or
(e) X5 is 0, 1, 3, or 4 contiguous amino acid residues that do not alternate between L and D residues.

In one embodiment, the polypeptides are linear and possess an α-strand-turn-α-strand structure. In one such embodiment that can be combined with any other embodiment herein unless the context clearly dictates otherwise, X2 and X4 are of different length (i.e.: they are not symmetrical). For example, where X2 is 5 contiguous amino acid residues alternating between D amino acids and L amino acids. X4 might be 7 contiguous amino acid residues alternating between D amino acids and L amino acids.

In one such embodiment:
X1 is absent;
X2 is 7 contiguous amino acid residues alternating between D amino acids and L amino acids;
X3 is 3 contiguous amino acid residues that do not alternate between L and D residues;
X4 is 9 contiguous amino acid residues alternating between D amino acids and L amino acids; and
X5 is absent.

In another embodiment, the isolated polypeptide is not rgeMnLsWmneysgwTmNlKmgr (SEQ ID NO: 2).

Exemplary polypeptides according to this embodiment include, but are not limited to the following polypeptides or their reverse chiral counterparts:

```
                                     (SEQ ID NO: 11)
EqQISwINAAAaWtQqLkQ;

(SEQ ID NO: 12)
EqQISwKNAAAaWtQqLkQ;
```

-continued

```
                                       (SEQ ID NO: 13)
EqQISwTNAAAaWtKqLkQ;

(SEQ ID NO: 14)
EqQISwTNAAAaWtQqLkK;

(SEQ ID NO: 15)
EqQISwKNAAAaWtQqLkK;

(SEQ ID NO: 16)
EqQISwTNAAAaWtKqLkK;

(SEQ ID NO: 17)
EqQISwKNAAAaWtKqLkQ;

(SEQ ID NO: 18)
EqQISwTNPAAaWtQqLkQ;

(SEQ ID NO: 19)
EqQISwTNAPAaWtQqLkQ;

(SEQ ID NO: 20)
EqQIEwTNAAAaWkQqLkQ;

(SEQ ID NO: 21)
EqQIEwTNAAAaWkQqLkQ;

(SEQ ID NO: 22)
EqQISITNAAAaLtQqLkQ;

(SEQ ID NO: 23)
EqQISiTNAAAaItQqLkQ;

(SEQ ID NO: 24)
EqQiSiTNAAAaItQqLkQ;

(SEQ ID NO: 25)
NmNISIMNEYSaLtMnLqM;

(SEQ ID NO: 26)
NmNISIMNAAAaLtMnLqM;

(SEQ ID NO: 27)
NmNISIMNAASaLtMnLqM;
and (SEQ ID NO: 28)
QqQqQqQNAAAaQqQqQqQ.
```

As will be understood by those of skill in the art, the "reverse chiral counterpart" of a listed polypeptide is a polypeptide with an identical amino acid sequence but wherein each residue has the opposite chirality (e.g., each "L" residue is changed to a 'D" residue and each 'D" residue is changed to an "L" residue. By way of non-limiting example, the reverse chiral counterpart of EqQlSwT-NAAAaWtQqLkQ (SEQ ID NO: 11) is eQqLsWtnaaaAw-TqQlKq (SEQ ID NO: 11). Based on the teachings herein, the identity of the reverse chiral counterpart of each specific polypeptide disclosed herein will be clear to those of skill in the art.

In another embodiment:

X1 is absent;

X2 is 8 contiguous amino acid residues alternating between D amino acids and L amino acids;

X3 is 3 contiguous amino acid residues that do not alternate between L and D residues;

X4 is 10 contiguous amino acid residues alternating between 1) amino acids and L amino acids; and X5 is absent.

Exemplary polypeptides according to this embodiment include, but are not limited to the following polypeptides or their reverse chiral counterparts:

```
                                       (SEQ ID NO: 29)
kEqQISwTNAAAaWtQqLkQq;

(SEQ ID NO: 30)
kEqQISwTNPAAaWtQqLkQq;

(SEQ ID NO: 31)
kEqQISwTNAPAaWtQqLkQq;

(SEQ ID NO: 32)
kEqQIEwTNAAAaWkQqLkQq;

(SEQ ID NO: 33)
kEqQISwTNAPAaWtQqLrQq;
and (SEQ ID NO: 34)
kEqQIEwTNAPAaWkQqLkQq.
```

In another embodiment:

X1 is 2 contiguous amino acid residues that do not alternate between L amino acids and D amino acids;

X7 is 7 contiguous amino acid residues alternating between D amino acids and L amino acids;

X3 is 3 contiguous amino acid residues that do not alternate between L and D residues;

X4 is 9 contiguous amino acid residues alternating between D amino acids and L amino acids; and X5 is 2 contiguous amino acid residues that do not alternate between L amino acids and D amino acids.

Exemplary polypeptides according to this embodiment include, but are not limited to the following polypeptides or their reverse chiral counterparts:

```
                                       (SEQ ID NO: 35)
RGEqQISwTNAAAaWtQqLkQGR;

(SEQ ID NO: 36)
RGEmNISwMNAAAaWtMnLkMGR;

(SEQ ID NO: 37)
RGEqQISwTNAAAaWtMqLkQGR;

(SEQ ID NO: 38)
RGEmNISwMNEYSGWtMnLkMGR;
and (SEQ ID NO: 39)
RGEmNISwANEYSNWtMnLkMGR.
```

In another embodiment:

X1 is absent;

X7 is 7 contiguous amino acid residues alternating between D amino acids and L amino acids;

X3 is 4 contiguous amino acid residues that do not alternate between L and D residues;

X4 is 8 contiguous amino acid residues alternating between D amino acids and L amino acids; and X5 is absent.

Exemplary polypeptides according to this embodiment include, but are not limited to the following polypeptides or their reverse chiral counterparts:

```
                                       (SEQ ID NO: 40)
NmNISIMAEYSGltMnLqM;

(SEQ ID NO: 41)
NmNISIMNETSGltMnLqM.
```

In another embodiment:

X1 is absent;

X7 is 7 contiguous amino acid residues alternating between D amino acids and L amino acids;

X3 is 1 contiguous amino acid residues that do not alternate between L and D residues;

X4 is 4 contiguous amino acid residues alternating between D amino acids and L amino acids; and X5 is absent.

Exemplary polypeptides according to this embodiment include, but are not limited to the following polypeptides or their reverse chiral counterparts:

```
                                         (SEQ ID NO: 42)
QlSwEpNKWtQk;

(SEQ ID NO: 43)
QqSwEpNKWtLk;
and (SEQ ID NO: 44)
SmTlEpNKLtLk.
```

In another embodiment that can be combined with any other embodiment herein unless the context clearly dictates otherwise, X2 and X4 are the same length (i.e.: they are symmetrical). For example, X2 and X4 may each be 5, 6, 7, 8, or 9 contiguous amino acid residues alternating between D amino acids and L amino acids.

In one non-limiting embodiment of such symmetrical polypeptides:

X1 is absent;

X2 is 7 contiguous amino acid residues alternating between D amino acids and L amino acids;

X3 is 5 contiguous amino acid residues that do not alternate between L and D residues;

X4 is 7 contiguous amino acid residues alternating between D amino acids and L amino acids; and X5 is absent.

Exemplary polypeptides according to this embodiment include, but are not limited to the following polypeptides or their reverse chiral counterparts:

```
                                         (SEQ ID NO: 45)
NmNISIMNEYSNLtMnLqM;

(SEQ ID NO: 46)
NmNISIMNEYSDLtMnLqM;

(SEQ ID NO: 47)
NmNISIMNEYSGLtMnLqM;

(SEQ ID NO: 48)
NmNISIMLEYSGLtMnLqM;

(SEQ ID NO: 49)
EmNISIMNEYSGLtMnLkM;

(SEQ ID NO: 50)
NmNISIMNEYSGFtMnLqM;

(SEQ ID NO: 51)
NmNISwMNEYSGWtMnLqM;

(SEQ ID NO: 52)
MnLnLsFNEYSGMfTINmQ;

(SEQ ID NO: 53)
NmNISIMGEYSGLtMnLqM;

(SEQ ID NO: 54)
NmNISIMGEYSNLtMnLqM;

(SEQ ID NO: 55)
NmNISIMNEASGLtMnLqM;

(SEQ ID NO: 56)
NwNISwMNEYSGWtMnWqM;

(SEQ ID NO: 57)
EmNISwMNEYSGWtMnLkM;

(SEQ ID NO: 58)
NtNISIMNETSGLtMnTqK;

(SEQ ID NO: 59)
NmNISIMNKTSGLtMnLqM;

(SEQ ID NO: 60)
NtNISwMNETSGWtMnTqK;

(SEQ ID NO: 61)
NtNISIMNEYSGLtMnTqK;

(SEQ ID NO: 62)
NtNISwMNEYSGWtMnTqK;

(SEQ ID NO: 63)
NmNISIMNAATGLtMnLqM;

(SEQ ID NO: 64)
NmNISIMNAATGLtMnLqM;

(SEQ ID NO: 65)
NmNISIMGDYSNLtMnLqM;

(SEQ ID NO: 66)
NmNISIMGAASNLtMnLqM;

(SEQ ID NO: 67)
QmQISIMNEYSGLtMqLqM;
and (SEQ ID NO: 68)
QmQISIQNEYSGLtMqLqQ.
```

In another non-limiting embodiment of such symmetrical polypeptides:

X1 is 2 contiguous amino acid residues that do not alternate between L amino acids and D amino acids;

X7 is 7 contiguous amino acid residues alternating between D amino acids and L amino acids;

X3 is 5 contiguous amino acid residues that do not alternate between L and D residues;

X4 is 7 contiguous amino acid residues alternating between D amino acids and L amino acids; and X5 is 2 contiguous amino acid residues that do not alternate between L amino acids and D amino acids.

Exemplary polypeptides according to this embodiment include, but are not limited to the following polypeptides or their reverse chiral counterparts:

```
                                         (SEQ ID NO: 69)
RGNmNISwMNEYSGWtMnLqMGR;

(SEQ ID NO: 70)
RGEmNISwMNEYSGWtMnLkMGR;

(SEQ ID NO: 71)
RGEmNISwMNEYYGWtMnLkMGR;

(SEQ ID NO: 72)
RGEmAISwMNEYSGWtMnLkMGR;

(SEQ ID NO: 73)
RGEmNISwMNEYYGWtCnLkMGR;

(SEQ ID NO: 74)
RGEmNISwMNEYYGWtMnCkMGR;

(SEQ ID NO: 75)
RGEmNISwMNEYYGWtMnLkCGR;
```

-continued

```
                                  (SEQ ID NO: 76)
RGEmNISwMNEYYGWtMnLkMCR;

(SEQ ID NO: 77)
RGEmNISwMNEYYGWcMnLkMGR;

(SEQ ID NO: 78)
RGEmNISwMNEYYGWtMcLkMGR;

(SEQ ID NO: 79)
RGEmNISwMNEYYGWtMnLcMGR;

(SEQ ID NO: 80)
RGEmNIFwMNEYYGWtMnLkMGR;

(SEQ ID NO: 81)
RGEmNISwMNEYYGWtKnLkMGR;

(SEQ ID NO: 82)
RGEmNISwMNEYYGWtMnKkMGR;

(SEQ ID NO: 83)
RGEmNIFwMNEYYGWtMnCkMGR;

(SEQ ID NO: 84)
RGEmNIFwMNEYYGWtRnCkMGR;

(SEQ ID NO: 85)
RGEmNIFwMNEYYGWtKnCkMGR;

(SEQ ID NO: 86)
RGEmNIFwMLEYYGWtMnCkMGR;

(SEQ ID NO: 87)
RGEmNIFwMHEYYGwtMnCkMGR;

(SEQ ID NO: 88)
RGEmNIFwMMEYYGWtMnCkMGR;

(SEQ ID NO: 89)
AQQiEcItNVWDKEItMyFnVSE;
and (SEQ ID NO: 90)
WRPwGiDqMNTVKQRkAsVyLQP.

(SEQ ID NO: 91)
RGNwNeSkMNEYSGWmLmLtMGR.
```

In another embodiment, the polypeptides comprise or consist of cyclic α-sheet hairpins that have a second turn engineered to close the sequence. In one such embodiment that can be combined with any other embodiment herein unless the context clearly dictates otherwise, X2 and X4 are of different length (i.e.: they are not symmetrical). In one such embodiment. X1 is 0 or 1 amino acid, and X5 is 0 or 1 amino acid. In another such embodiment.

X1 is absent;
X2 is 5-7 contiguous amino acid residues alternating between D amino acids and L amino acids;
X3 is 0-3 contiguous amino acid residues that do not alternate between L and D residues;
X4 is 6-11 contiguous amino acid residues alternating between D amino acids and L amino acids; and
X5 is 0 or 1 amino acid residue.
In another such embodiment,
X1 is absent;
X2 is 6 contiguous amino acid residues alternating between D amino acids and L amino acids;
X3 is 3 contiguous amino acid residues that do not alternate between L and D residues;
X4 is 11 contiguous amino acid residues alternating between D amino acids and L amino acids; and
X5 is 1 amino acid residue.
Exemplary polypeptides according to this embodiment include, but are not limited to the following polypeptides or their reverse chiral counterparts:

```
                                  (SEQ ID NO: 92)
qQkSwTNAAAaWtMqLkEpNK;

(SEQ ID NO: 93)
qWkSwTNAAAaWtMqLwDpNR;

(SEQ ID NO: 94)
qQkSwTNAAAaWtMqLkDpNR;

(SEQ ID NO: 95)
lQkSwTNAAAaWtMqLkDpNR;

(SEQ ID NO: 96)
qLkSwTNAAAaWtMqLlDpNR;

(SEQ ID NO: 97)
wQkSwTNAAAaWtMqWkDpNR;

(SEQ ID NO: 98)
eWkSwTNAAAaWtMqLwDpNR;

(SEQ ID NO: 99)
eQkSwTNAAAaWtMqLkDpNR;

(SEQ ID NO: 100)
qQlSwTNAAAaWtMqLkEpNK;

(SEQ ID NO: 4)
eLkSwTNAAAaWtMqLlDpNR;

(SEQ ID NO: 102)
eWkSwTNAAAaWtEqLwDpNR;

(SEQ ID NO: 103)
qQkSwTNEYSaWtMqLkEpNK;

(SEQ ID NO: 104)
qQkSwTNEYYaWtMqLkEpNK;

(SEQ ID NO: 105)
qQkFwTNEYYaWtMqLkEpNK;

(SEQ ID NO: 106)
qQkSwTNEYYaWtMqCkEpNK;

(SEQ ID NO: 107)
qQkSwTNEYYaWtCqLkEpNK;

(SEQ ID NO: 108)
qQkFwTNAAAaWtMqLkEpNK;
and (SEQ ID NO: 109)
qQkFwTNAAAaWtEqLkEpNK.
```

In another such embodiment,
X1 is absent;
X2 is 7 contiguous amino acid residues alternating between D amino acids and L amino acids;
X3 is 1 amino acid residue that do not alternate between L and D residues;
X4 is 6 contiguous amino acid residues alternating between D amino acids and L amino acids; and
X5 is absent.
Exemplary polypeptides according to this embodiment include, but are not limited to the following polypeptides or their reverse chiral counterparts:

```
                                  (SEQ ID NO: 110)
SdTlDpNRLtRkpP;

(SEQ ID NO: 111)
SnTlDpNRLtRkpP;
```

-continued

S1T1DpNRLtLkpP; (SEQ ID NO: 112)
and

S1TnDpNRRtLkpP. (SEQ ID NO: 113)

In another such embodiment,
X1 is absent;
X2 is 6 contiguous amino acid residues alternating between D amino acids and L amino acids;
X3 is 3 contiguous amino acid residues that do not alternate between L and D residues;
X4 is 10 contiguous amino acid residues alternating between D amino acids and L amino acids; and
X5 is 1 amino acid residue.

Exemplary polypeptides according to this embodiment include, but are not limited to the following polypeptides or their reverse chiral counterparts:

qQkFwTNAAAaWtMqkEpNK; (SEQ ID NO: 114)
and qQkFwTNEYYaWtMqkEpNK. (SEQ ID NO: 115)

In another such embodiment,
X1 is absent;
X2 is 8 contiguous amino acid residues alternating between D amino acids and L amino acids;
X3 is 3 contiguous amino acid residues that do not alternate between L and D residues;
X4 is 12 contiguous amino acid residues alternating between D amino acids and L amino acids; and
X5 is absent.

Exemplary polypeptides according to this embodiment include, but are not limited to the following polypeptides or their reverse chiral counterparts:

kEqQISwTNAPAaWtQqLkQqPp; (SEQ ID NO: 116)
and kEqQISwTNAAAaWtQqLkQqPp. (SEQ ID NO: 117)

In various embodiments, the polypeptide comprises or consists of 13-23, 14-23, 15-23, 16-23, 17-23, 18-23, 19-23, 20-23, 21-23, 22-23, 12-22, 13-22, 14-22, 15-22, 16-22, 17-22, 18-22, 19-22, 20-22, 21-22, 12-21, 13-21, 14-21, 15-21, 16-21, 17-21, 18-21, 19-21, 20-21, 12-20, 13-20, 14-20, 15-20, 16-20, 17-20, 18-20, 19-20, 12-19, 13-19, 14-19, 15-19, 16-19, 17-19, 18-19, 12-18, 13-18, 14-18, 15-18, 16-18, 17-18, 12-17, 13-17, 14-17, 15-17, 16-17, 12-16, 13-16, 14-16, 15-16, 12-15, 13-15, 14-15, 12-14, 13-14, 12-13, 12, 13, 14, 15, 16, 17, 18, 19, 20, 21, 22, or 23 amino acids of general formula 1.

In another embodiment the isolated polypeptide features a first Fourier-transform infrared (FTIR) signal between about 1675-1680 cm$^{-1}$ and a second FTIR signal at about 1640 cm$^{-1}$, wherein the first signal FTIR signal is stronger than the second FTIR signal. Alternatively, the isolated polypeptide may feature a first Fourier-transform infrared (FTIR) signal between about 1675-1680 cm$^{-1}$ and a second FTIR signal at about 1640 cm$^{-1}$, wherein the first signal FTIR signal is weaker than the second FTIR signal. As shown in the examples, polypeptides of the invention often possess such FTIR signal patterns.

In another embodiment, the polypeptides of the invention comprise or consist of a primary amino acid sequence according to the general formula 2:

R1-R2-R3-R4-R5-R6-R7-R8-R9-R10-R11-R12-R13-
R14-R15-R16-R17-R18-R19-R20-R21-R22-R23
(SEQ ID NO: 118), wherein at least residues R2-R12 are present in the isolated peptide, and wherein R1 is selected from the group consisting of R, M, E, (k), N, K, Q, S, V, L, W (w), (q), and A, or their reverse chiral counterparts, or is absent;

R2 is selected from the group consisting of G, (q), E, (m), (n), (w), (t), (l), A, S, Q, (k), and N, or their reverse chiral counterparts;

R3 is selected from the group consisting of E, Q, (q), N, T, S, (l), (k), W, and P, or their reverse chiral counterparts;

R4 is selected from the group consisting of (q), (m), M, (l), Q, (w), K, (t), E, (i), and (a), or their reverse chiral counterparts;

R5 is selected from the group consisting of Q, N, E, S, (l), L, (t), (k), (w), (q), A, W, and G, or their reverse chiral counterparts;

R6 is selected from the group consisting of (l), G, (w), S, (i), E, (f), and (s), or their reverse chiral counterparts;

R7 is selected from the group consisting of S, N, T, K, (w), M, F, Q, L, (k), (t), W, (l), E, G, I, Y, and D, or their reverse chiral counterparts;

R8 is selected from the group consisting of (w), R, N, T, G, A, (n), (a), K, (q), E, (k), L, (t), and (l), or their reverse chiral counterparts;

R9 is selected from the group consisting of T, M, (k), A, N, P, E, K, D, L, W, (w), and Q, or their reverse chiral counterparts;

R10 is selected from the group consisting of N, E, S, A, P, Y, T, (t), (l), V, (q), L, H, and M, or their reverse chiral counterparts;

R11 is selected from the group consisting of A, E, (p), (n), S, T, L, Q, Y, P, R, W, and N, or their reverse chiral counterparts;

R12 is selected from the group consisting of A, Y, N, M, W, (a), D, G, (k), (q), L, and V, or their reverse chiral counterparts;

R13 is selected from the group consisting of A, S, K, L, W, (a), I, F, W, M, (l), Y, V, R, and Q, or their reverse chiral counterparts, or is absent;

R14 is selected from the group consisting of (a), A, W, N, (t), (k), (f), G, Q, S, (l), (w), (q), T, Y, and E, or their reverse chiral counterpart, s or is absent;

R15 is selected from the group consisting of (q), (k), Q, (w), (t), T, W, G, I, M, L, R, and K, or their reverse chiral counterparts, or is absent;

R16 is selected from the group consisting of (t), M, G, (q), Q, (n), (l), K, (k), L, T, (c), and (m), or their reverse chiral counterparts, or is absent;

R17 is selected from the group consisting of Q, M, (n), (l), L, (q), N, W, T, S, (t), (k), (m), C, K, R, and A, or their reverse chiral counterparts, or is absent;

R18 is selected from the group consisting of (q), (n), L, (w), (k), (m), H, D, W, (l), Q, E, L, T, S, (y), (c), and (s), or their reverse chiral counterparts, or is absent;

R19 is selected from the group consisting of L, (k), S, Q, K, M, F, (q), T, W, (r), (t), C, N, and V, or their reverse chiral counterparts, or is absent;

R20 is selected from the group consisting of (k), M, T, S, (n), (c), (y), (t), N, Q, and (q), or their reverse chiral counterparts or is absent;

R21 is selected from the group consisting of Q, M, G, W, N, (q), T, E, (t), (k), (l), V, C, and L, or their reverse chiral counterparts, or is absent;

R22 is selected from the group consisting of G, R, Y, H, (n), S, C, and Q, or their reverse chiral counterparts, or is absent; and R23 is selected from the group consisting of R, M, E, and P, or their reverse chiral counterparts, or is absent.

In the various general formulae disclosed herein, amino acid residues recited in the uppercase and not within parentheses are in the "L" configuration ("L amino acids"), while those in lower case and within parentheses are in the 'D" configuration ("D amino acids"). In the specific sequences recited, amino acid residues recited in the uppercase are "L amino acids", while those in lower case are "D amino acids".

In one embodiment R1 is an L amino acid residue. In another embodiment the C-terminal residue is an L amino acid residue.

In another embodiment, the primary sequence of cyclic polypeptides according to the invention comprise or consist of a primary amino acid sequence according to the general formula 3:

R1-R2-R3-R4-R5-R6-R7-R8-R9-R10-R1-R12-R13-
R14-R15-R16-R17-R18-R19-R20-R21-R22-R23
(SEQ ID NO: 119), wherein at least residues R1-R14 are present in the isolated peptide, and wherein R1 is selected from the group consisting of S, (q), (l), (w), (e), Q, and (k), or their reverse chiral counterparts;

R2 is selected from the group consisting of (l), Q, W, L, E, (d), and (n), or their reverse chiral counterparts;

R3 is selected from the group consisting of T, (k), (l), (q), and S, or their reverse chiral counterparts;

R4 is selected from the group consisting of (l), S, Q, (w), (n), and F, or their reverse chiral counterparts;

R5 is selected from the group consisting of D, (w), (l), and T, or their reverse chiral counterparts;

R6 is selected from the group consisting of (p), T, S, N, and W, or their reverse chiral counterparts;

R7 is selected from the group consisting of N, (w), and A, or their reverse chiral counterparts;

R8 is selected from the group consisting of R, A, T, and E, or their reverse chiral counterparts;

R9 is selected from the group consisting of (l), L, A, N, and Y, or their reverse chiral counterparts;

R10 is selected from the group consisting of T, (t), A, (a), S, and Y, or their reverse chiral counterparts;

R11 is selected from the group consisting of (l), L, (a), P, A, R, and W, or their reverse chiral counterparts;

R12 is selected from the group consisting of K, (k), W, A, and (t), or their reverse chiral counterparts;

R13 is selected from the group consisting of (p), (t), (a), and M, or their reverse chiral counterparts;

R14 is selected from the group consisting of P, M, W, (q), E, and C, or their reverse chiral counterparts;

R15 is selected from the group consisting of (q), (t), and L, or their reverse chiral counterparts, or is absent;

R16 is selected from the group consisting of L, W, Q, P, (k), and C, or their reverse chiral counterparts, or is absent;

R17 is selected from the group consisting of (k), (w), (l), (q), (p), P, and E, or their reverse chiral counterparts, or is absent;

R18 is selected from the group consisting of E, D, L, (p), and P, or their reverse chiral counterparts, or is absent;

R19 is selected from the group consisting of (p), (k), and N, or their reverse chiral counterparts, or is absent;

R20 is selected from the group consisting of N, Q, and K, or their reverse chiral counterparts, or is absent;

R21 is selected from the group consisting of K, R, and (q), or their reverse chiral counterparts, or is absent;

R22 is P, or its reverse chiral counterpart, or is absent; and

R23 is (p), or its reverse chiral counterpart, or is absent.

In various embodiments, R1 is a D amino acid residue and/or the C-terminal residue is an L-amino acid residue. In a further embodiment of the cyclic polypeptides of the invention, R1 is selected from the group consisting of S, (q), (e), and Q, or their reverse chiral counterparts;

R2 is selected from the group consisting of (l) and Q, or their reverse chiral counterparts;

R3 is selected from the group consisting of T and (k), or their reverse chiral counterparts;

R4 is selected from the group consisting of (l), S, and F, or their reverse chiral counterparts;

R5 is selected from the group consisting of D and (w), or their reverse chiral counterparts;

R6 is selected from the group consisting of (p) and T, or their reverse chiral counterparts;

R7 is N, or its reverse chiral counterpart;

R8 is selected from the group consisting of A and E, or their reverse chiral counterparts;

R9 is selected from the group consisting of L, A, and Y, or their reverse chiral counterparts;

R10 is selected from the group consisting of (t), A, and Y, or their reverse chiral counterparts;

R11 is (a), or its reverse chiral counterpart;

R12 is selected from the group consisting of (k) and W, or their reverse chiral counterparts;

R13 is selected from the group consisting of (p) and (t), or their reverse chiral counterparts;

R14 is selected from the group consisting of P and M, or their reverse chiral counterparts;

R15 is (q), or its reverse chiral counterparts;

R16 is L, or its reverse chiral counterparts;

R17 is selected from the group consisting of (k), (l) and E, or their reverse chiral counterparts;

R18 is selected from the group consisting of E and D, or their reverse chiral counterparts;

R19 is (p), or its reverse chiral counterpart;

R20 is selected from the group consisting of N and K, or their reverse chiral counterparts;

R21 is selected from the group consisting of K and R, or their reverse chiral counterparts;

R22 is absent; and

R23 is absent.

In various further embodiments, the cyclic polypeptide comprises or consists of a primary amino acid sequence selected from the group consisting of the following polypeptides or their reverse chiral counterparts:

TABLE A

| | |
|---|---|
| SlTlDpNRlTlKpP | (SEQ ID NO: 120) |
| SlTlDpNRLtLkpP | (SEQ ID NO: 121) |

TABLE A-continued qQkSwTNAAAaWtMqLkEpNK (SEQ ID NO: 92)

qWkSwTNAAAaWtMqLwDpNR (SEQ ID NO: 93)

qQkSwTNAAAaWtMqLkDpNR (SEQ ID NO: 94)

lQkSwTNAAAaWtMqLkDpNR (SEQ ID NO: 95)

qLkSwTNAAAaWtMqLlDpNR (SEQ ID NO: 96)

wQkSwTNAAAaWtMqWkDpNR (SEQ ID NO: 97)

eWkSwTNAAAaWtMqLwDpNR (SEQ ID NO: 98)

eQkSwTNAAAaWtMqLkDpNR (SEQ ID NO: 99)

qQlSwTNAAAaWtMqLkEpNK (SEQ ID NO: 100)

kEqQlSwTNAPAaWtQqLkQqPp (SEQ ID NO: 116)

kEqQlSwTNAAAaWtQqLkQqPp (SEQ ID NO: 117)

SdTlDpNRLtRkpP (SEQ ID NO: 110)

QlSwTNAAAaWtMqLPp (SEQ ID NO: 101)

QlSnTWAAAaWtMqLkPp (SEQ ID NO: 122)

SnTlDpNRLtRkpP (SEQ ID NO: 111)

SlTlDpNRLtLkpP (SEQ ID NO: 112)

eLkSwTNAAAaWtMqLlDpNR (SEQ ID NO: 4)

eWkSwTNAAAaWtEqLwDpNR (SEQ ID NO: 102)

qQkSwTNEYSaWtMqLkEpNK (SEQ ID NO: 103)

qQkSwTNEYYaWtMqLkEpNK (SEQ ID NO: 104)

qQkFwTNEYYaWtMqLkEpNK (SEQ ID NO: 105)

qQkSwTNEYYaWtMqCkEpNK (SEQ ID NO: 106)

qQkSwTNEYYaWtMqLEpNK (SEQ ID NO: 123)

qQkSwTNEYYaWtCqLkEpNK (SEQ ID NO: 107)

qQkFwTNAAAaWtMqLkEpNK (SEQ ID NO: 108)

qQkFwTNAAAaWtEqLkEpNK (SEQ ID NO: 109)

qQkFwTNAAAaWtMqkEpNK (SEQ ID NO: 114)

qQkFwTNEYYaWtMqkEpNK (SEQ ID NO: 115)

qQlSwTNAAAaWtMqLlPp (SEQ ID NO: 124)

SlTnDpNRRtLkpP (SEQ ID NO: 125)

In another embodiment, the polypeptide comprises or consists of a primary amino acid sequence selected from the group consisting of the following polypeptides or their reverse chiral counterparts:

TABLE B

RGEqQlSwTNAAAaWtQqLkQGR (SEQ ID NO: 35)

RGEmNlSwMNEYSAWtMnLkMGR (SEQ ID NO: 126)

RGEmNlSwMNAAAaWtMnLkMGR (SEQ ID NO: 36)

RGEmNlSwMEpNKWtMnLkMGR (SEQ ID NO: 127)

MGEMEGNRkSnMLNRGlwStWYm (SEQ ID NO: 128)

EqQlSwTNAAAaWtQqLkQ (SEQ ID NO: 11)

EqQlSwKNAAAaWtQqLkQ (SEQ ID NO: 12)

EqQlSwTNAAAaWtKqLkQ (SEQ ID NO: 13)

EqQlSwTNAAAaWtQqLkK (SEQ ID NO: 14)

kEqQlSwTNAAAaWtQqLkQq (SEQ ID NO: 29)

EqQlSwKNAAAaWtQqLkK (SEQ ID NO: 15)

EqQlSwTNAAAaWtKqLkK (SEQ ID NO: 16)

EqQlSwKNAAAaWtKqLkQ (SEQ ID NO: 17)

qQlSwTNAAAaWtQqLk (SEQ ID NO: 129)

EqQlSwTNPAaWtQqLkQ (SEQ ID NO: 18)

EqQlSwTNAPAaWtQqLkQ (SEQ ID NO: 19)

EqQlEwTNAAAaWkQqLkQ (SEQ ID NO: 20)

EqQlEwTNAAAaWkQqLkQ (SEQ ID NO: 21)

EqQlSlTNAAAaLtQqLkQ (SEQ ID NO: 22)

EqQlSiTNAAAaItQqLkQ (SEQ ID NO: 23)

TABLE B-continued

| | |
|---|---|
| EqQiSiTNAAAaItQqLkQ | (SEQ ID NO: 24) |
| kEqQlSwTNPAAaWtQqLkQq | (SEQ ID NO: 30) |
| kEqQlSwTNAPAaWtQqLkQg | (SEQ ID NO: 31) |
| kEqQlEwTNAAAaWkQqLkQq | (SEQ ID NO: 32) |
| NmNlSlMNEYSNLtMnLqM | (SEQ ID NO: 45) |
| NmNlSlMNEYSDLtMnLqM | (SEQ ID NO: 46) |
| NmNlSlMNEYSGLtMnLqM | (SEQ ID NO: 47) |
| NmNlSlMLEYSGLtMnLqM | (SEQ ID NO: 48) |
| EmNlSlMNEYSGLtMnLkM | (SEQ ID NO: 49) |
| NmNlSfMNEYSGFtMnLqM | (SEQ ID NO: 50) |
| NmNlSwMNEYSGWtMnLqM | (SEQ ID NO: 51) |
| MnLnLsFNEYSGMfTlNmQ | (SEQ ID NO: 52) |
| NmNlSlMGEYSGLtMnLqM | (SEQ ID NO: 53) |
| NmNlSlMGEYSNLtMnLqM | (SEQ ID NO: 54) |
| NmNlSlMNEASGLtMnLqM | (SEQ ID NO: 55) |
| NmNlSlMAEYSGltMnLqM | (SEQ ID NO: 40) |
| NmNlSlMNETSGltMnLqM | (SEQ ID NO: 41) |
| NwNlSwMNEYSGWtMnWqM | (SEQ ID NO: 56) |
| EmNlSwMNEYSGWtMnLkM | (SEQ ID NO: 57) |
| NtNlSlMNETSGLtMnTqK | (SEQ ID NO: 58) |
| NmNlSlMNKTSGLtMnLqM | (SEQ ID NO: 59) |
| NtNlSwMNETSGWtMnTqK | (SEQ ID NO: 60) |
| NtNlSlMNEYSGLtMnTqK | (SEQ ID NO: 61) |
| NtNlSwMNEYSGWtMnTqK | (SEQ ID NO: 62) |
| RGNmNlSwMNEYSGWtMnLqMGR | (SEQ ID NO: 69) |
| NmNlSlMnEYSGLtMnLqM | (SEQ ID NO: 47) |
| NmNlSlMNEYSaLtMnLqM | (SEQ ID NO: 25) |

TABLE B-continued

| | |
|---|---|
| NmNlSlMNAATGLtMnLqM | (SEQ ID NO: 63) |
| NmNlSlMNAATGLtMnLqM | (SEQ ID NO: 64) |
| NmNlSlMNAAAaLtMnLqM | (SEQ ID NO: 26) |
| NmNlSlMNAASaLtMnLqM | (SEQ ID NO: 27) |
| NmNlSlMaAAAaLtMnLqM | (SEQ ID NO: 130) |
| NmNlSlMGDYSNLtMnLqM | (SEQ ID NO: 65) |
| NmNlSlMGAASNLtMnLqM | (SEQ ID NO: 66) |
| RGEmNlSwMNEYSGWtMnLkMGR | (SEQ ID NO: 38) |
| QmQlSlMNEYSGLtMqLqM | (SEQ ID NO: 67) |
| QmQlSlQNEYSGLtMqLqQ | (SEQ ID NO: 68) |
| SmTlEpNKLtLk | (SEQ ID NO: 44) |
| RGEqQlSwTNAAAaWtMqLkQGR | (SEQ ID NO: 37) |
| QlSwEpNKWtQk | (SEQ ID NO: 42) |
| QqSwEpNKWtLk | (SEQ ID NO: 43) |
| RGEmNlSwMNEYSGWtMnLkMGR | (SEQ ID NO: 70) |
| RGEmNlSwMNEYSNWtMnLkMGR | (SEQ ID NO: 7) |
| RGEmNyFwMNEYYGWtMnkMGR | (SEQ ID NO: 131) |
| VALKLHKNEYYGVALKLHK | (SEQ ID NO: 132) |
| LALKSDFNEYYGLALKSDF | (SEQ ID NO: 133) |
| QwEqSLQkNAPAakQltWqqT | (SEQ ID NO: 134) |
| WSqQtqLwNAPAaQqkklQTE | (SEQ ID NO: 135) |
| QqEtkwkTNAPAaSqLlQqQW | (SEQ ID NO: 136) |
| wqEtLlQqNAPAakqQkWQST | (SEQ ID NO: 137) |
| kQqWwqtTNAPAalkqLEQSQ | (SEQ ID NO: 138) |
| QkEWqwSqNAPAalqQQLTkt | (SEQ ID NO: 139) |
| SQltQqkTNAPAawqLWEqQk | (SEQ ID NO: 140) |

TABLE B-continued

QtkqSwWENAPAaqQTLqQkl (SEQ ID NO: 141)

klQtEqwqNAPAaSQLkQWTq (SEQ ID NO: 142)

qEWqLQlkNAPAaqwQkTStQ (SEQ ID NO: 143)

kEqQlSwTNAPAaWtQqLrQq (SEQ ID NO: 33)

LlqqQkEwNAPAaQTkQStqW (SEQ ID NO: 144)

qqEwSQLkNAPAaqWklQtQT (SEQ ID NO: 145)

kQQqwEqLNAPAaTklqQtSW (SEQ ID NO: 146)

KEQQLSWTNAPAaWTQQLKQQ (SEQ ID NO: 31)

kEqQlEwTNAPAaWkQqLkQq (SEQ ID NO: 34)

MNWESkGEwlRMRYGtmLSNGnM (SEQ ID NO: 147)

AQQiEcItNVWDKEItMyFnVSE (SEQ ID NO: 89)

QqQqQqQNAAAaQqQqQqQ (SEQ ID NO: 28)

QqQqEpNKQqQq (SEQ ID NO: 148)

RGEmNlSwMNEYYGWtMnLkMGR (SEQ ID NO: 71)

RGEmAlSwMNEYSGWtMnLkMGR (SEQ ID NO: 72)

RGEmNlSwMNEYYGWtCnLkMGR (SEQ ID NO: 73)

RGEmNlSwMNEYYGWtMnCkMGR (SEQ ID NO: 74)

RGEmNlSwMNEYYGWtMnLkCGR (SEQ ID NO: 75)

RGEmNlSwMNEYYGWtMnLkMCR (SEQ ID NO: 76)

RGEmNlSwMNEYYGWcMnLkMGR (SEQ ID NO: 77)

RGEmNlSwMNEYYGWtMcLkMGR (SEQ ID NO: 78)

RGEmNlSwMNEYYGWtMnLcMGR (SEQ ID NO: 79)

RGEmNlFwMNEYYGWtMnLkMGR (SEQ ID NO: 80)

RGEmNlSwMNEYYGWtKnLkMGR (SEQ ID NO: 81)

RGEmNlSwMNEYYGWtMnKkMGR (SEQ ID NO: 82)

RGEmNlFwMNEYYGWtMnCkMGR (SEQ ID NO: 83)

RGEmNlFwMNEYYGWtRnCkMGR (SEQ ID NO: 84)

TABLE B-continued

RGEmNlFwMNEYYGWtKnCkMGR (SEQ ID NO: 85)

RGEmNlFwMLEYYGWtMnCkMGR (SEQ ID NO: 86)

RGEmNlFwMHEYYGWtMnCkMGR (SEQ ID NO: 87)

RGEmNlFwMMEYYGWtMnCkMGR (SEQ ID NO: 88)

RGEaWmYlKNNLSETmMsNMWGR (SEQ ID NO: 149)

WRPwGiDqMNTVKQRkAsVyLQP (SEQ ID NO: 90)

RGNwNeSkMNEYSGWmLmLtMGR (SEQ ID NO: 91)

RGEaWmYlKNNLSETmMsNMWGR (SEQ ID NO: 149)

The inventors have discovered that the polypeptides of the invention adopt an α-sheet structure, regardless of the primary amino acid sequence and thus can be used, for example, in the therapeutic and diagnostic methods of the invention described herein. The polypeptides of the invention are useful for inhibiting aggregation and/or binding of the toxic oligomeric form of amyloidogenic intermediates, as well as for use as diagnostic/imaging agents Referring to FIG. 5, and as detailed in the examples that follow, evidence that the primary amino acid sequence of the polypeptides does not per se dictate the inhibitory activity (here defined as inhibition of aggregation and/or binding of toxic oligomer) of the polypeptides is presented. Instead it is the ability of the polypeptides to adopt a stable α-sheet structure that is operative, which is achieved through the recited polypeptide generic structure and the recited arrangement of alternating D/L amino acids. Random primary sequences of amino acids are active in the polypeptides of the invention; these same primary sequences are not active if the polypeptide is provided in an entirely L-amino acid peptide or if the L/D amino acids are randomly distributed within the polypeptide such that they are not alternating (i.e.: if they are not polypeptides according to the invention).

Based on all of the above, the inventors have clearly demonstrated that the primary amino acid sequences are not determining the α-sheet structure and associated activity, or in other words, there is degeneracy and many primary amino acid sequences are active within the templated structure provided by alternating L/D amino acids. The specific amino acids do modulate the stability, solubility and degree of activity, however.

In a further aspect, the present invention provides pharmaceutical compositions, comprising one or more (1, 2, 3, 4, 5, 6, 7, 8, 9, 10, or more) polypeptides of any embodiment or combination of embodiments of the invention and a pharmaceutically acceptable carrier. The pharmaceutical compositions of the invention can be used, for example, in the methods of the invention described below. The pharmaceutical composition may comprise in addition to the polypeptide(s) of the invention (a) a lyoprotectant; (b) a surfactant; (c) a bulking agent; (d) a tonicity adjusting agent; (e) a stabilizer; (f) a preservative and/or (g) a buffer.

In some embodiments, the buffer in the pharmaceutical composition is a Tris buffer, a histidine buffer, a phosphate buffer, a citrate buffer or an acetate buffer. The pharmaceutical composition may also include a lyoprotectant. e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The polypeptides of the invention may be the sole active agent in the pharmaceutical composition, or the composition may further comprise one or more other active agents suitable for an intended use.

The pharmaceutical compositions described herein are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be formulated for administration by any suitable route. The pharmaceutical compositions can be in any suitable form, including but not limited to tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

The polypeptides of the invention can be capped or uncapped, as most appropriate for any given use. In various embodiments, one or both of the N-terminus or the C-terminus of the polypeptide is acetylated or amidated. In other embodiments, neither the N-terminus nor the C-terminus is capped. The polypeptides may be linked to other compounds to promote an increased half-life in vivo, such as by PEGylation, HESylation, PASylation, or glycosylation. Such linkage can be covalent or non-covalent as is understood by those of skill in the art.

In one embodiment, the polypeptide comprises the recited amino acid structure; in this embodiment, the polypeptides may, for example, be linked (covalently or non-covalently) onto other polypeptides to increase stability, reduce half-life, provide bifunctionality, etc.; or onto other compounds or moieties as desired, including but not limited to detectable labels. The label(s) can be linked to the polypeptide through covalent bonding, including, but not limited to, disulfide bonding, hydrogen bonding, electrostatic bonding, recombinant fusion and conformational bonding. Alternatively, the label(s) can be linked to the polypeptide by means of one or more linking compounds. Techniques for conjugating labels to polypeptides are well known to the skilled artisan. Polypeptides comprising a detectable label can be used diagnostically to, for example, assess if a subject has toxic amyloidogenic intermediates in a tissue or bodily fluid sample, or monitor the development or progression of an a treatment regimen to eradicate toxic amyloidogenic intermediates (i.e., determine the efficacy of a given treatment regimen. However, they may also be used for other detection and/or analytical and/or diagnostic purposes. Any suitable detection label can be used, including but not limited to enzymes, prosthetic groups, fluorescent materials, luminescent materials, bioluminescent materials, radioactive materials, positron emitting metals, and nonradioactive paramagnetic metal ions. The label used will depend on the specific detection/analysis/diagnosis techniques and/or methods used such as immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., neutralization assays), Western blotting applications, etc.

The polypeptides of the invention can also be attached to solid supports, which are particularly useful for in vitro assays or therapeutic procedures to remove toxic amyloidogenic intermediates from a subject. Such solid supports might be porous or nonporous, planar or nonplanar and include, but are not limited to, glass, nanoparticles, quantum dots, cellulose, polyacrylamide, nylon, polystyrene, polyvinyl chloride or polypropylene supports. The polypeptides can also, for example, usefully be conjugated to filtration media, such as NHS-activated Sepharose or CNBr-activated Sepharose, agarose beads for purposes of affinity chromatography. They can also usefully be attached to paramagnetic microspheres, typically by biotin-streptavidin interaction. As another example, the polypeptides of the invention can usefully be attached to the surface of a microtiter plate for ELISA.

In a third aspect, the present invention provides methods for treating an amyloid disease, comprising administering to a subject with an amyloid disease an amount effective of the isolated polypeptide of any embodiment or combination of embodiments of the invention, or a pharmaceutical composition thereof, to treat the amyloid disease.

As described in the examples that follow, while the alpha sheet polypeptides of the present invention were not designed against a specific protein target, inhibition of aggregation was observed in three very different amyloid systems. These results support the hypothesis that the α-sheet structure may constitute a broad-based inhibitor of amyloidosis, and thus the polypeptides of the invention a novel class of amyloid inhibitors that specifically target the toxic soluble oligomeric state of different amyloidogenic peptides and proteins. In various non-limiting embodiments, the amyloid disease may be selected from the group consisting of Creutzfeldt-Jakob disease, spongiform encephalopathy, Huntington's disease, amyotrophic lateral sclerosis (ALS), senile systemic amyloidosis, familial amyloid polyneuropathy (transthyretin). Kennedy disease, Machado-Joseph disease, Alzheimer's disease, bovine spongiform encephalopathy, scrapie, type 2 diabetes, amyloidosis caused by transthyretin (ATTR), Parkinson's disease, atherosclerosis, rheumatoid arthritis, aortic medial amyloid, prolactinomas, dialysis-related amyloidosis, cerebral amyloid angiopathy, Finnish amyloidosis, lattice corneal dystrophy, and multiple myeloma.

As used herein, "treating an amyloid disease" means accomplishing one or more of the following: (a) reducing the severity of the amyloid disease; (b) limiting or preventing development of symptoms characteristic of the amyloid disease(s) being treated; (c) inhibiting worsening of symptoms characteristic of the amyloid disease(s) being treated; (d) limiting or preventing recurrence of the amyloid disease(s) in patients that have previously had the disorder(s); (e) limiting or preventing recurrence of symptoms in patients that were previously symptomatic for the amyloid disease(s); and (f) limiting development of the amyloid disease in a subject at risk of developing the amyloid disease, or not yet showing the clinical effects of the dental disease.

As used herein, an "amount effective" refers to an amount of the polypeptide that is effective for treating and/or limiting amyloid disease. The polypeptides are typically formulated as a pharmaceutical composition, such as those disclosed above, and can be administered via any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally.

Dosage regimens can be adjusted to provide the optimum desired response (e.g., a therapeutic or prophylactic response). A suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. The polypeptides can be delivered in a single bolus, or may be administered more than once (e.g., 2, 3, 4, 5, or more times) as determined by an attending physician.

In a fourth aspect, the present invention provides methods for diagnosing or prognosing an amyloid disease, comprising (a) contacting a tissue sample from a subject at risk of having an amyloid disease with any embodiment or combination of embodiments of the invention, or a pharmaceutical composition thereof, under conditions suitable for binding of the isolated polypeptide with an amyloid intermediate, if present in the tissue sample, to produce a binding complex;

(b) detecting binding complexes in the tissue sample; and (c) diagnosing or prognosing an amyloid disease based on the detecting.

The methods of this aspect of the invention can be used to more accurately diagnose or prognose patients that may be suffering from an amyloid disease and to thus provide more informed determination of treatment options by an attending caregiver. Individuals at risk of an amyloid disease are those exhibiting one or more signs, symptoms, or risk factors for an amyloid disease, including but not limited to Creutzfeldt-Jakob disease, spongiform encephalopathy, Huntington's disease, amyotrophic lateral sclerosis (ALS), senile systemic amyloidosis, familial amyloid polyneuropathy, Kennedy disease, Machado-Joseph disease, Alzheimer's disease, bovine spongiform encephalopathy, scrapie, type 2 diabetes, amyloidosis caused by transthyretin (ATTR), Parkinson's disease, atherosclerosis, rheumatoid arthritis, aortic medial amyloid, prolactinomas, dialysis-related amyloidosis, cerebral amyloid angiopathy, Finnish amyloidosis, lattice corneal dystrophy, and multiple myeloma.

The tissue sample may be any suitable tissue sample including, but not limited to blood, serum, cerebral spinal fluid, nasal secretions, urine or other biological material from a subject at risk of an amyloid disease.

Conditions suitable for binding the polypeptides of the invention with an amyloid intermediate, if present in the tissue sample, to produce a binding complex will depend on specifics of the polypeptide(s) being used, the tissue sample, and the technique employed. Determining such suitable conditions are within the level of skill in the art based on the teachings herein.

The formation of such complexes, if any, indicating the presence of amyloid intermediates in the sample, is then detected and measured by suitable means. Such methods include, but are not limited to homogeneous and heterogeneous binding immunoassays, such as radioimmunoassays (RIA), ELISA, immunofluorescence, immunohistochemistry. FACS, BIACORE and Western blot analyses.

The polypeptides of the invention for use in this aspect may comprise a conjugate as disclosed above, to provide a tag useful for any detection technique suitable for a given assay. The tag used will depend on the specific detection/analysis/diagnosis techniques and/or methods used. The methods may be carried in solution, or the polypeptide(s) of the invention may be bound or attached to a carrier or substrate, e.g., microtiter plates (ex: for ELISA), membranes and beads, etc. Carriers or substrates may be made of glass, plastic (e.g., polystyrene), polysaccharides, nylon, nitrocellulose, or teflon, etc. The surface of such supports may be solid or porous and of any convenient shape.

Example 1. Designed α-Sheet Peptides Inhibit Amyloid Formation by Targeting the Toxic Oligomeric Form Previous studies suggest that the toxic soluble-oligomeric form of different amyloid proteins share a common backbone conformation, but the amorphous nature of this oligomer prevents its structural characterization by experiment. Here the experimental characterization of peptides designed to be complementary to the α-sheet conformation observed in the simulations is reported. Inhibition of aggregation is demonstrated in two different amyloid systems, β-amyloid peptide 1-42 (Aβ) and transthyretin (TTR), by these designed α-sheet peptides. When immobilized the α-sheet designs preferentially bind species from solutions enriched in the toxic conformer compared with non-aggregated, non-toxic species or mature fibrils. The designs display characteristic spectroscopic signatures distinguishing them from conventional secondary structures, supporting α-sheet as a structure involved in the toxic oligomer stage of amyloid formation and paving the way for novel therapeutics and diagnostics.

There are now over 40 different human amyloid diseases, each linked to the buildup of a specific precursor protein or peptide (1). These diseases involve the conversion of a protein from its soluble native state into insoluble amyloid fibrils, or, in the case of peptides, the conversion from a soluble, loosely structured form to fibrils. Given that many different sequences can form amyloid fibrils of similar architecture, there may be some common structural features of the prefibrillar amyloidogenic intermediates. X-ray fiber diffraction indicates that the insoluble, mature amyloid fibrils are composed of cross β-sheet structure (2). Therefore, it is widely held that the formation of amyloid fibrils involves a transition to β-sheet structure in the amyloidogenic intermediate. However, the mechanism of self-assembly at the atomic level remains elusive. Another feature of these diseases is that soluble oligomeric intermediates, not the insoluble well-ordered fibrils, are preferentially responsible for cellular toxicity (3-6). Similarly, the soluble oligomeric forms of the prion protein are the most infectious per unit protein (7). As such, fibrils may be protective, at least up to a point, as their breakdown to smaller aggregates yields greater toxicity and infectivity. The discovery of a compound that promotes inclusion formation while reducing toxicity and cellular pathology supports this hypothesis (8).

Research on the soluble oligomers has become critically important since there is a consensus that the soluble oligomer species is more toxic than mature fibrils (5, 6). In fact, structural similarities between soluble oligomers from a range of unrelated proteins/peptides has been suggested based on an antibody that recognizes a common backbone structure (5, 6, 9). Glabe and co-workers developed an antibody (denoted A11) that binds soluble oligomeric intermediates derived from a variety of peptides and proteins, including Aβ(1-42), α-synuclein, islet amyloid polypeptide, polyglutamine, lysozyme, human insulin, and a prion peptide (10). The antibody does not, however, bind the corresponding insoluble fibrils (cross-β structure) or the natively folded precursors (various structures). Based on the specificity of the antibody for soluble oligomers with various sequences, it was proposed that the antibody recognizes a unique conformation of the backbone. This antibody inhibits toxicity associated with the intermediates, implying a common mechanism of toxicity and offering hope for a broad-based therapeutic agent.

Some years ago the inventors "discovered" a novel secondary structure, which is called "α-sheet", that is populated during molecular dynamics (MD) simulations of a range of amyloid proteins (and peptides) with different structures and sequences under amyloidogenic conditions (FIG. 1a) (11-14). The position where the α-sheet forms along the sequence coincides with the most amyloidogenic regions of the proteins, as determined experimentally (13). An α-sheet is similar to a β-sheet, but instead of alternating main chain NH and C=O groups along the strands, an α-sheet has the NH groups aligned on one side and the carbonyls on the other. As such, the α-sheet has a molecular dipole and a very different hydrogen-bonding pattern across the sheet compared to a β-sheet. Interestingly, the main chain (Φ, Ψ) dihedral angles of the α-sheet alternate between the $α_L$ and $α_R$ conformations (15) (FIG. 1a). Although locally helical, the alternating dihedral angles form an extended chain resulting in the carbonyl groups and amide groups aligning in a plane. Such an arrangement creates uniform electrostatic faces to aid in the addition of further strands (11). Once a sheet is formed, a simple peptide plane flip could convert the α-sheet into a β-sheet and ultimately a mature fibril (15). Extensive α-sheet formation has not been observed in native proteins.

To investigate the role of α-sheet in amyloid formation, numerous small, stable α-hairpin peptides were computationally designed. It was reasoned that if α-sheet is the novel backbone structure in toxic oligomers, then α-sheet peptides designed to be complementary to the structure in the oligomer should bind to the toxic oligomer and inhibit amyloidosis. The designs began with a backbone template in an ideal α-sheet conformation. Investigation was then carried out on combinations of residues with high propensities to populate desired regions of conformational space using the Structural Library of Intrinsic Residue Propensities (SLIRP), which is part of the Dynameomics project (18, 19). Owing to the expected transient nature of the at conformation, the structure was stabilized using D-amino acids, which essentially have inverted conformational propensities compared with their normal L-counterparts (FIG. 1b). Peptides containing alternating D- and L-amino acids have previously been shown to form extended structures (20, 21), and they populate similar conformational space as the MD-identified α-sheet sequences in amyloid systems consisting solely of L-amino acids. MD simulations (22) were performed to assess the stability of the de novo designed amino acid sequences. Sequences designed to adopt β-sheet and random coil conformations were included in the experiments as controls.

Several of the most promising peptide designs were selected for experimental characterization in two different amyloid systems: transthyretin (TTR) and beta amyloid 1-42 [Aβ(1-42) or Aβ for short]. Both are associated with amyloid diseases but have completely different sequences and structures. Aβ is a largely unstructured peptide fragment in aqueous solution, but it aggregates to become the dominant component of plaques from patients with Alzheimer's Disease. In contrast, TTR is a tetramer composed of immunoglobulin-like β-sandwich domains; TTR aggregation is associated with peripheral polyneuropathy and systemic senile amyloidosis. Both systems have well characterized aggregation profiles and aggregate under mild, non-denaturing conditions (23-25). Here the focus is on five peptide designs (β, rc, α1, α2, α3) (FIG. 1c). β is the Trpzip 3 peptide (26) but with Trp to Leu substitutions to improve spectroscopic properties. The β-design was intended to be a negative control for TTR and a positive control for Aβ, as β-hairpins are known inhibitors of Aβ aggregation (27). rc was designed to be an unstructured random coil to provide a negative control; it is a scrambled, random sequence of the β-sheet design, β. The remaining three peptides were designed to adopt α-sheet structure. α1 and α2 are linear hairpins containing a sheet of alternating D- and L-amino acids. α1 was designed to have high α-sheet propensity. α2 is a derivative of α1 with modifications aimed to improve stability and the introduction of a Cys for coupling experiments. α3 consists of a sheet of alternating D- and L-amino acids and two turns, creating a cyclic amide backbone. It was not possible to design a soluble, random coil control based on the α-sheet peptides, i.e. the same composition and length. Shuffling of the amino acid sequences resulted in insoluble peptides that were unusable in the solution-phase assays, so it was determined to use smaller but well-defined controls.

Figure 2:
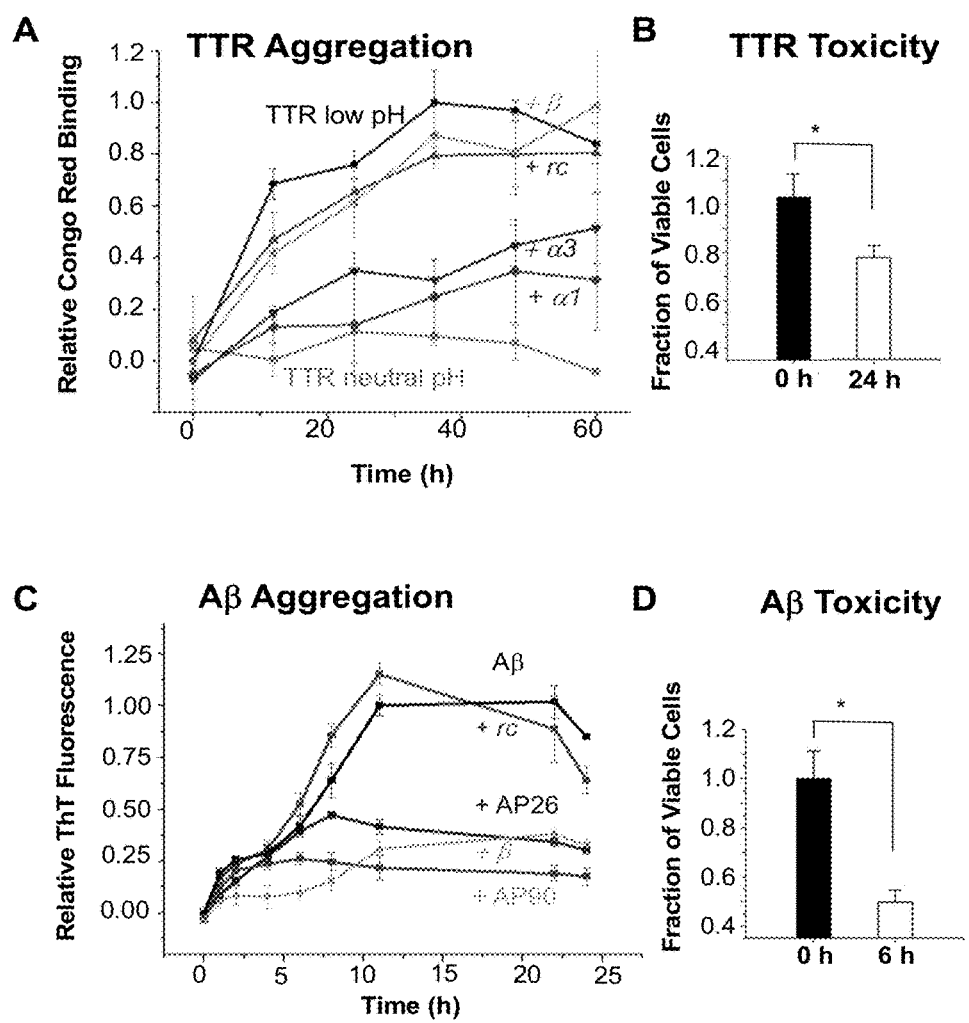
FIG. 2. α-Sheet designs inhibit amyloid formation and selectively bind toxic species. (A) Peptide designs (800 μM) were co-incubated at pH 4.5 with 40 μM TTR (monomer) at 37° C. and aggregation was monitored by Congo red binding. Error bars indicate the standard deviation. (B) Toxicity of the TTR solution after 24 hr pre-incubation at pH 4.5 against the human neuroblastoma cell line SH-SY5Y in a MTT metabolic viability assay. (C) Thioflavin T (ThT) monitoring of 10 μM of the A-beta (1-42) peptide implicated in Alzheimer's Disease (hereafter referred to as Aβ) aggregation and inhibitory effects of 100 μM designed peptides present from the beginning of the aggregation at 37° C. (D) Aβ toxicity after 6 hrs of aggregation, as probed using the MTT assay and the SH-SY5Y cell line. All data represent average±s.d. and (* indicates P<0.05, determined using Student's t-test).

First the peptides were tested for anti-amyloidogenic activity in a fibrillization assay using transthyretin (TTR). Four of the five designed peptides (α2 was sparingly soluble and therefore not tested in any solution-phase experiments) were co-incubated with TTR (in excess 20:1, expressed relative to TTR monomer) at pH 4.5 to trigger dissociation of the native tetramer followed by aggregation (23, 24). The aggregation was monitored via binding of Congo red (FIG. 2a). It was not possible to use thioflavin T (ThT) as an extrinsic dye to monitor the aggregation of transthyretin, as addition of ThT to freshly dissolved and filtered TTR gives high background fluorescence. For this reason Congo red was used, which did not bind monomeric TTR. The percentage inhibition of aggregation was determined after 48 hours at 37° C., after the aggregation stabilized. At these concentrations, α1 and α3 resulted in 72 and 56% inhibition, respectively, relative to TTR alone at low pH. In contrast, the rc and β controls resulted in little to no inhibition. The neutral pH tetrameric TTR control changed little over time. Moreover, the designs in the absence of TTR did not bind Congo red and were indistinguishable from the buffer-only controls (data not shown).

Since the aim is to target the toxic oligomer, it was determined when the toxic oligomeric species was present during the course of aggregation. The toxicity of TTR was assessed by monitoring cell viability using the MTT assay after treating SH-SY5Y neuroblastoma cells with TTR that had been allowed to aggregate for different periods of time at pH 4.5. Toxicity began to build up around 24 hrs, and the results from this time point are shown in FIG. 2b. Under these conditions, the viability of the treated cells was reduced by approximately 20%, indicating that TTR was aggregating via the toxic pathway. Addition of the controls, rc or β, to a 24-hr pre-incubated TTR sample had no little to no effect on further aggregation, as detected with the Congo red assay. However, when α1 and α3 were mixed with 24-hour pre-incubated, toxic TTR, they inhibited 81% and 77%, respectively, of the remaining TTR aggregation observed in the absence of inhibitor.

Similarly, the designs were co-incubated (in 10:1 excess) with Aβ at pH 7.4 and followed fibril formation with ThT fluorescence changes upon binding at 37° C. (FIG. 2c). As observed for TTR, both α1 and α3 inhibited aggregation. Again α1 was more efficient, inhibiting approximately 87% of fibril formation compared with 66% for α3, when measured after the reaction stabilized at 22 hours. The β-sheet design, β, also resulted in 62% inhibition of Aβ fibrillization, and it exerted its effect primarily between 0 and 6 hrs. In contrast, α1 and α3 showed a distinct lag, becoming inhibitory after aggregation proceeded for approximately 6 hrs. The peptide designs alone did not alter the fluorescence of ThT, and, as with Congo red, they were indistinguishable from buffer-only controls over the time course of the assay (data not shown). Also note that the α-sheet designs are effective at lower concentrations and the efficacy increases at lower temperature; for example, a 4-fold excess of α1 essentially completely abolishes aggregation at 25° C. The 37° C. studies are reported here, though, for comparison with TTR, which aggregates very slowly at 25° C.

Aβ toxicity was also assessed using the MT assay and found to reduce the viability of treated SH-SY5Y cells to less than 50% after 6 hrs incubation (FIG. 2d). Addition of the α-sheet designs to a pre-aggregated (6 hrs), toxic sample of Aβ showed essentially complete inhibition, amounting to 97 and 96%, respectively for α1 and α3, compared with the extent of aggregation observed in the absence of inhibitor.

Figures 3A, 3B:
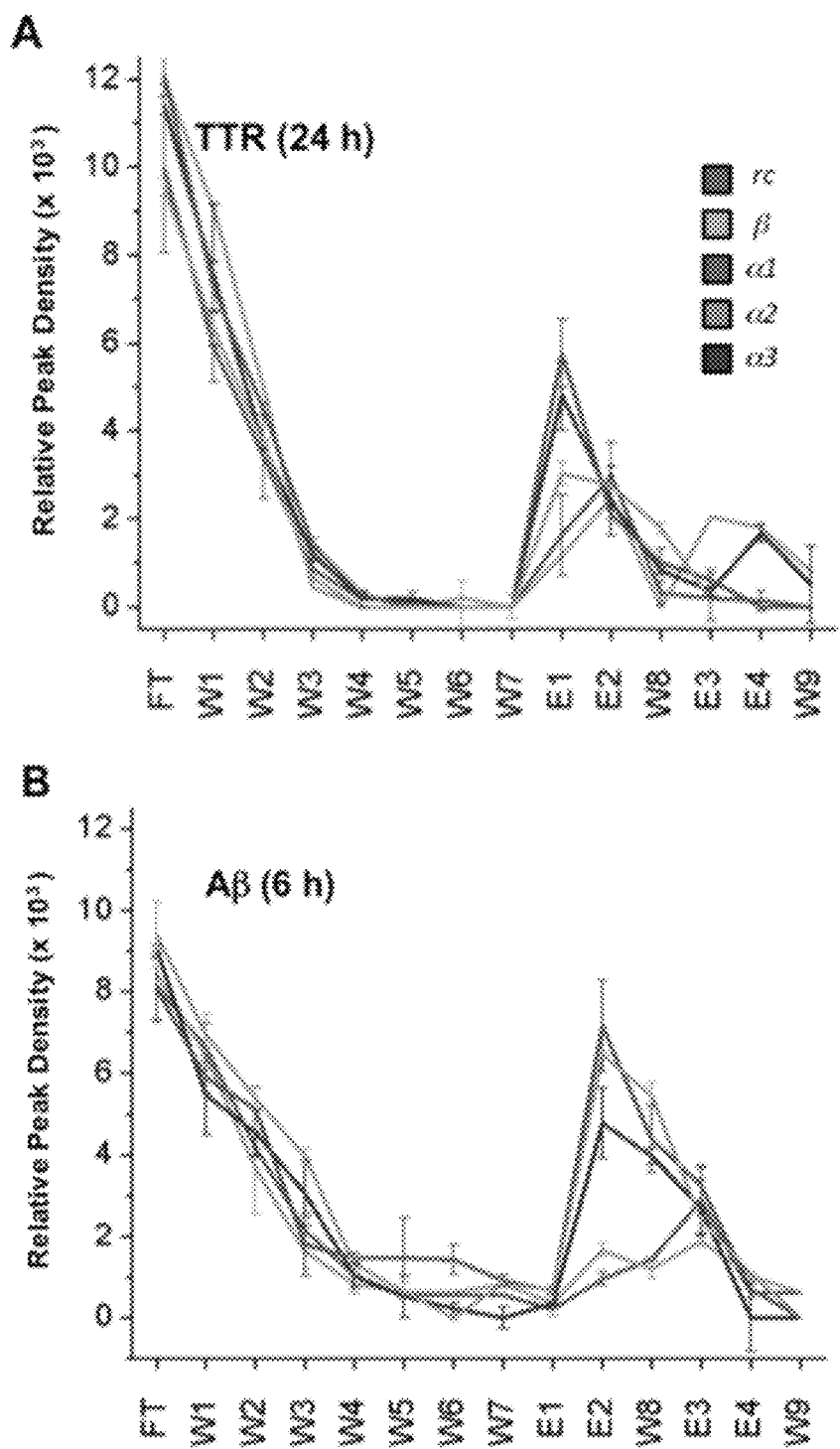
FIG. 3. Immobilized designs bind species from solutions. Peptide designs were immobilized via lysine residues on aldehyde-functionalized agarose beads and their ability to bind TTR or Aβ from solution at various stages of aggregation was probed using dot blot analysis. The presence of TTR or Aβ in the initial flow through (FT), sequential buffer washes (W), and sequential guanidine hydrochloride elution steps (E1-E2 and E3-E4) (x-axes) was detected by the integrated peak density of the dot blot analysis (y-axes). E1-W9 are within the linear range of the immunochemistry. (A) All three α-sheet designs, α1, α2 and α3 more strongly bound species from the 24 h pre-aggregated, toxic TTR solutions than did either control. (B) Similar results were observed with the α-sheet designs binding to toxic Aβ solutions pre-aggregated for 6 hrs. Despite the inhibitory effects seen with the β design in the Aβ assay, little Aβ from a pre-aggregated solution bound to the immobilized β design. (C) Comparison of binding from a fresh (0 h), or pre-aggregated (6 h), toxic Aβ solution. β is the only design that preferentially bound fresh Aβ over the aggregated toxic form, indicating that the inhibition observed was due to interactions with monomeric Aβ. (D) In contrast to the β control, α1 preferentially bound the pre-aggregated, toxic form of Aβ compared to fresh, monomeric Aβ.
Figures 3C, 3D:
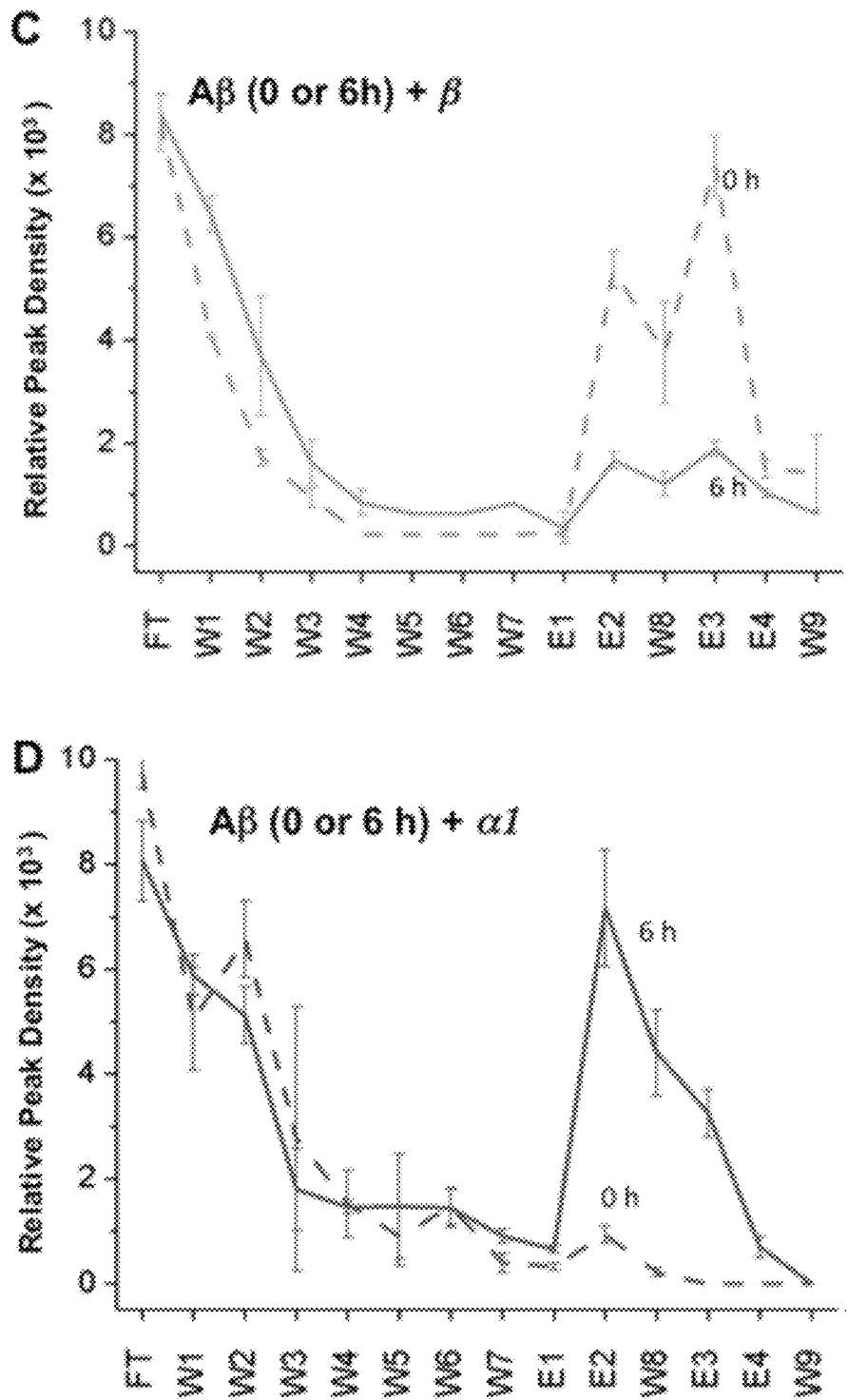

To further probe which species the peptide designs are binding to, the designs were immobilized on agarose beads and applied solutions of either fresh or pre-incubated, toxic samples of Aβ 3 and TTR. Immobilization in this manner also allowed us to test the sparingly soluble α2 design by limiting self-aggregation. All three immobilized α-sheet designs (α1, α2 and α3) bound pre-incubated, toxic oligomer-containing TTR solutions (pre-incubated at low pH for 24 hrs) to a greater extent than the rc and β controls (FIG. 3a). α1, α2 and α3 also bound pre-aggregated, toxic Aβ preferentially, whereas rc did not (FIG. 3b). In the case of the β design, it preferentially bound the fresh, monomeric Aβ (FIG. 3c), indicating that inhibition was due to interactions with the "native" form, not the toxic oligomer. β-hairpins are known inhibitors of Aβ aggregation (27). In contrast, α-sheet, as demonstrated with α1, did not bind native, tetrameric TTR nor fresh, monomeric Aβ but instead preferentially bound species from the toxic, aggregated samples (shown for Aβ in FIG. 3d). Moreover, the α-sheet designs did not bind the fibrillar forms of Aβ or TTR acquired by allowing the aggregation reactions to continue for over 3 weeks (data not shown).

The instability of α-sheet structure in proteins and peptides containing solely L-amino acids leaves no established spectroscopic signatures with which to assess the structures. However, predictions can be made and tested based on the unique conformational and electronic environments resulting from this structure. Circular dichroism (CD) signals arise from the differential absorption of left- and right-hand polarized light by chiral molecules. For proteins, the orientation of individual amide bonds is responsible for the resulting CD spectra in the far-UV region. Mirror image structures, formed by replacing whole L-amino acid sequences with D-amino acids, such as gramicidin A, produce mirror-image CD-spectra (29). The α-sheet structure is expected to be effectively invisible due to near equal absorbance of both left and right polarized light, with any residual signal emanating from the turns and terminal residues.

The electrostatic interactions between aligned amide groups in an α-sheet (13, 15) are expected to give rise to strong Fourier-transform infrared (FTIR) signals. Torii recently performed density functional theory calculations of three slightly different orientations of α-sheet structures (30). All models featured a strong high-frequency absorbance in the 1675-1680 $cm^{-1}$ region, with a weaker band around 1640 $cm^{-1}$, which is distinct from α-helix (~1650-1658 $cm^{-1}$) and β-sheet (~1620-1640 $cm^{-1}$) and instead overlaps somewhat with turn structures (~1670 $cm^{-1}$) (31).

Nuclear magnetic resonance (NMR) spectroscopy can provide site-specific conformational information. Owing to the unique alignment of the amide groups in an α-sheet, to see strong sequential $d_{NN}$ Nuclear Overhauser Effect (NOE) crosspeaks are expected along the backbone since the NH groups are aligned on one side of the chain instead of alternating between opposite faces as in β-sheet structure. Furthermore, the long-range $d_{NN}$ or the strong sequential $d_{αN}$ NOEs characteristic of β-sheets would not be expected. Thus, CD, FTIR and NMR studies were performed to assess the structures of the peptide designs.

Figures 4A, 4B:
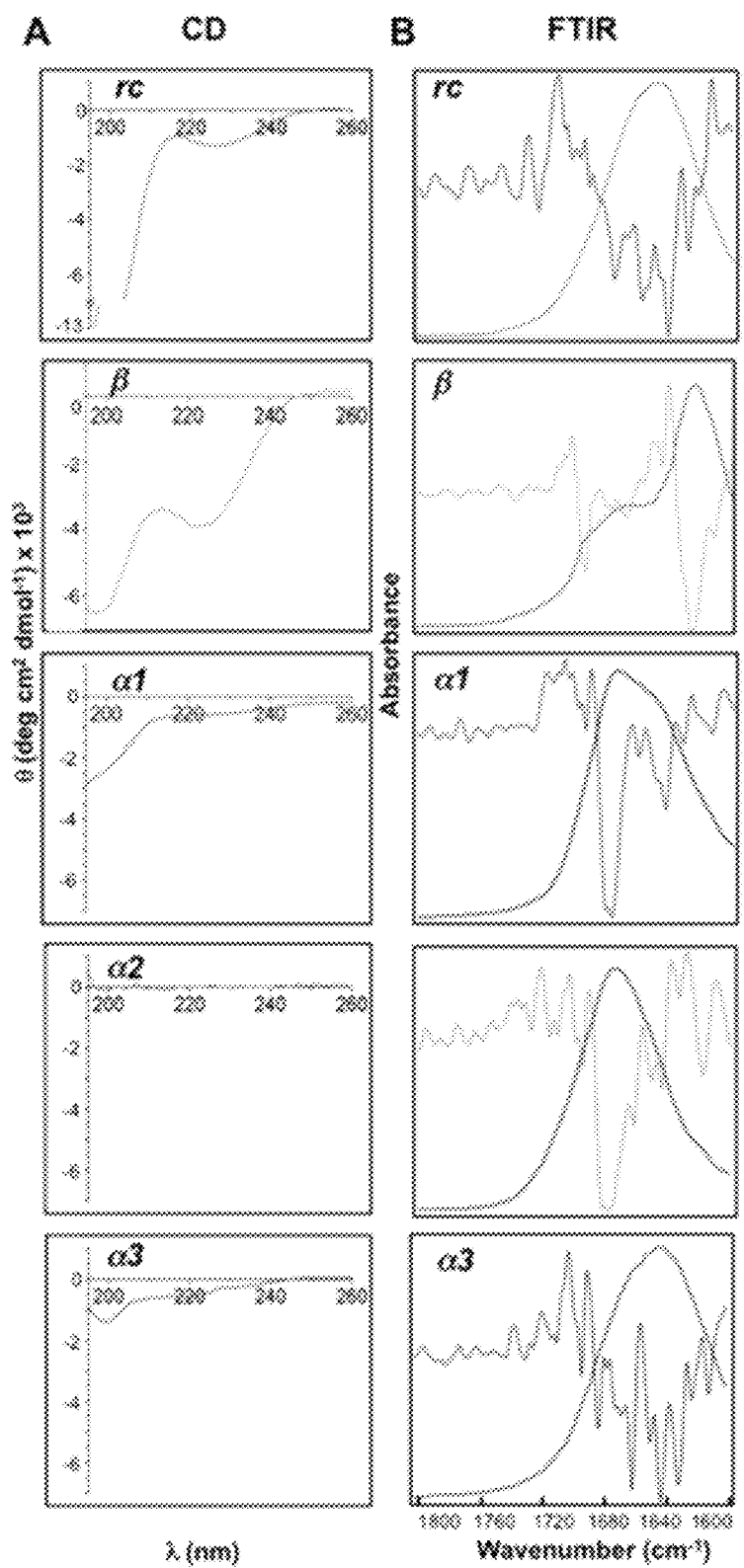
FIG. 4. Designed peptides display unique spectroscopic signatures expected for α-sheet. (A) CD spectra for peptide designs reveal a random coil structure for rc, and characteristic β-structure spectrum for β, with some random coil from the ends of the structure. In contrast, α1, α2 and α3 have largely featureless CD spectra with some random coil content expected to arise from the turns and tail residues. Note the different scales for the y-axes. All spectra are presented as molar ellipticity, highlighting the difference in intensity of the random coil component for each design. (B) FTIR spectra of the peptide designs, displayed as both absorbance (black line) and the second derivative (colored line), correlate well with the CD spectra. The β design shows a strong signal at 1632 cm$^{-1}$, as expected for β-structure. The α-sheet designs have signals near 1640 and 1675-1680 cm$^{-1}$ and the absorption is more intense for α1 and α2. (C) Fingerprint (top) and NH region (bottom) of the $^1$H NOESY spectra for α1. Sequential assignments are shown in red and multiple sequential NOEs are observed and labeled. (D) Fingerprint (top) and NH region (bottom) of the $^1$H NOESY spectra for α3. The NH region reflects the predominance of NH—NH interactions and lack of other main-chain interactions characteristic of the common secondary structures. Mapping backbone NOEs on computational models as green bars (E, α1 and F, α3) reveal in-plane alignment of the peptide groups along the majority of the sheet. NOEs in the turn regions determined whether the carbonyl or amide hydrogens pointed up in the structures as oriented in the figure (N-terminus top left). Cα, C, N, H and O atoms are shown in grey, grey, blue, white and red, respectively.

The CD spectrum of rc shows a random coil signal with a strong negative absorption around 195 nm (FIG. 4a). In its FTIR spectrum multiple small absorbance peaks not corresponding to a predominance of any specific structure are observed (FIG. 4b). The β-sheet control is a modified version of the Trpzip peptide, which forms a relatively stable β-hairpin in solution. In agreement with previous structural work (32), fl exhibits a CD spectrum reflective of β-structure with some random coil, with a minimum near 220 nm and another near 195 nm (FIG. 4a). The substitution of Leu for Trp removed the strong exciton-coupling between the Trp residues observed in the parent peptide thereby 'exposing' the β-structure CD signal. The β-sheet structure was confirmed by FTIR through its strong absorbance at 1632 $cm^{-1}$ (FIG. 4b). The CD spectra for α1, α2 and α3 are essentially featureless, as expected for the cancellation of $α_L$ and $α_R$ signals, except for a slight dip around 195 nm consistent with turn formation (FIG. 4a). α2 has a particularly featureless spectrum with a slight positive inflection around 195 nm, possibly due to a better ordered α-hairpin turn. α1 and α2 exhibited the predicted FTIR α-sheet bands at 1640 and 1675-1680 $cm^{-1}$ (FIG. 4b). These bands were less pronounced in α3. Cyclization of the amide backbone of α3 through a non-optimal turn may have caused distortion of the structure, as has been reported in other peptide systems (33) and suggests an area for improvement in future designs. Altogether, these results prove that the designed α-sheet peptides do not form α-helix or β-sheet structure, and that the random coil content is not large (compare against the scale of the rc control CD spectrum). Thus, these results are consistent with and supportive of the designed α-sheet structure.

Figures 4C, 4D:
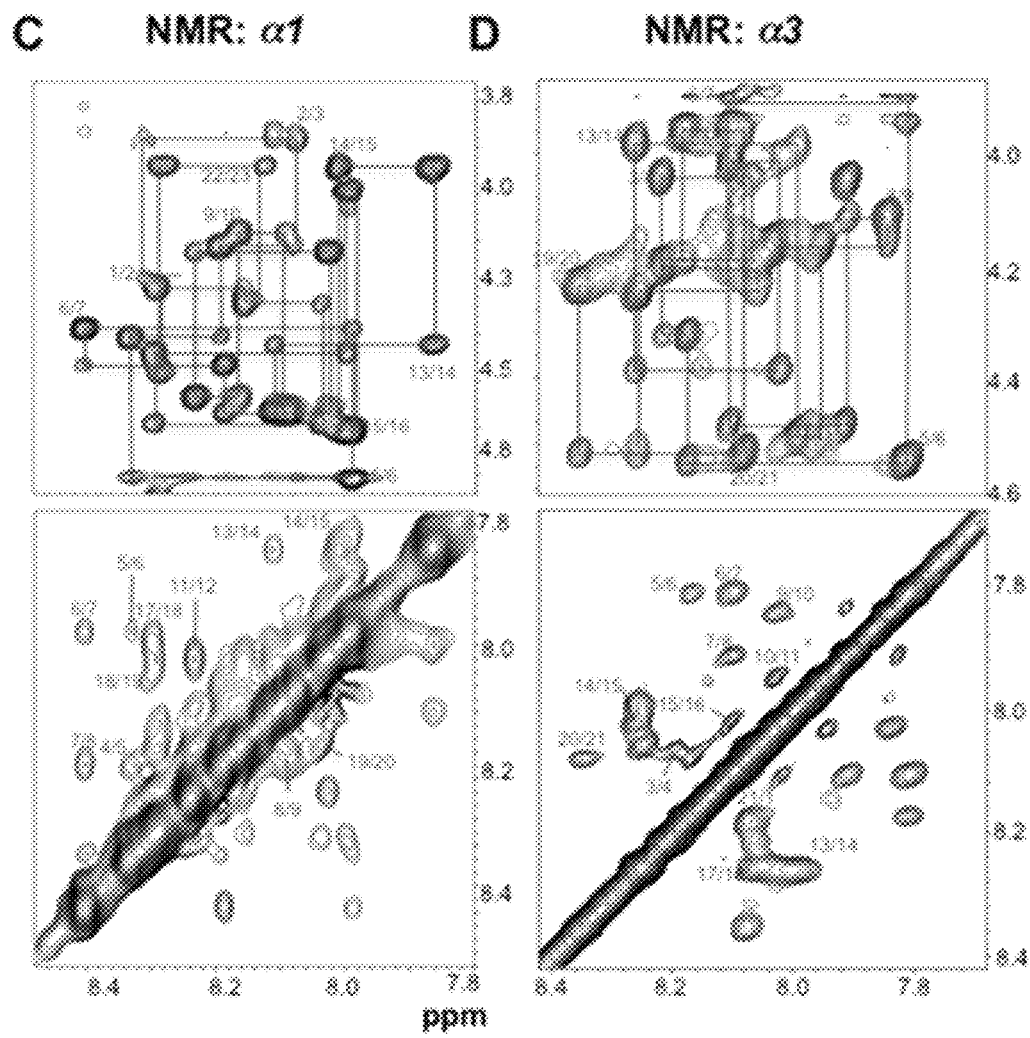
Figures 4E, 4F:
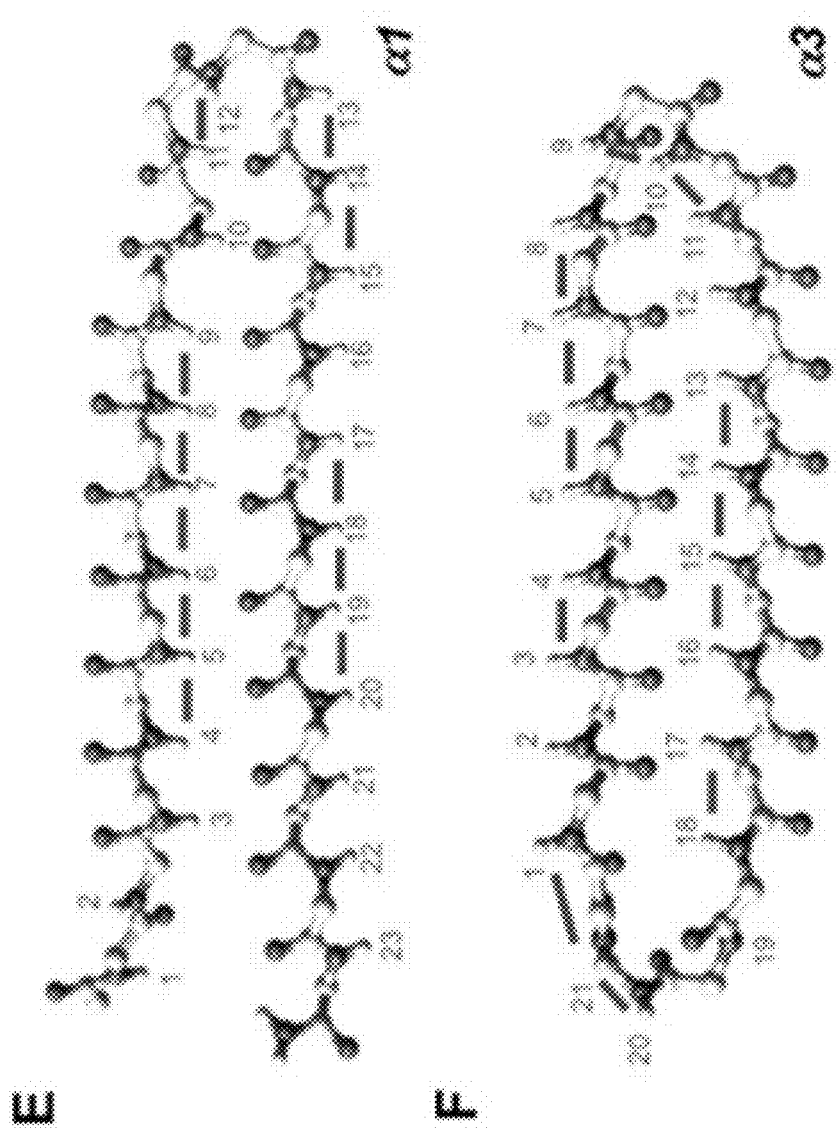

Further structural studies were performed utilizing homonuclear NMR spectroscopy. Multiple sequential $d_{NN}$ NOEs were observed along the backbones of both α1 and α3) (FIG. 4c,d). The α1 and α3 designs were well-behaved monomers under the conditions of the NMR experiments, which include very high sample concentrations in solvent conditions similar to those of the aggregation assays. In contrast, α2 was not soluble enough for NMR. Consequently the focus was on α1 and α3 here, and the observed NH . . . NH NOEs are mapped onto structural models of α1 and α3 in FIGS. 4e and f, highlighting the stretches of α-strand structure in both designs. No long-range $d_{NN}$ or $d_{\alpha N}$ NOEs indicative of α-helical or β-sheet structure (34) were observed. The breaks in the α-strand structure and the deformed turns highlight vulnerabilities in the design and provide suggestions for improved designs. No long-range side chain-side chain NOEs were observed despite increasing the mixing time of the NOESY experiments up to 400 ms, perhaps due to residual dynamics in the peptide. The lack of these distance restraints prevented the generation of a well-converged solution structure; however, the NMR data are consistent with α-sheet secondary structure and inconsistent with α-helix, random coil, and β-sheet structures.

Ten years ago a common conformation was demonstrated among soluble oligomeric species from amyloid proteins/peptides of diverse sequence and structures that cross react with the A11 antibody (9). Also at that time a novel target structure, α-sheet, was identified through MD simulations and proposed that it is the defining feature of the toxic oligomeric species (13, 15). Unfortunately, the precise structure of this toxic intermediate remains elusive, and it has become clear that the oligomers are conformationally heterogeneous (35, 36 and references therein). Here another approach was taken to probe these soluble oligomeric species and experimentally test the α-sheet hypothesis through peptides designed to be complementary to the proposed α-sheet structure. Three of these computationally derived designs have been synthesized and characterized experimentally, and they do indeed appear to adopt α-sheet structure (as shown by FTIR, CD and NMR). The two soluble α-sheet designs (α1 and α3) inhibited both TTR and Aβ aggregation in solution. In addition, conformation-specific binding was confirmed by passing solutions of nontoxic and toxic TTR and Aβ over all three α-sheet designs immobilized to agarose beads, which preferentially bound species from the toxic preparations. In contrast, the f/control formed a β-hairpin, as supported by CD and FTIR, and it preferentially bound the monomeric form of Aβ and it did not react with TTR in any form. When mature fibrils were applied to the immobilized α-sheet designs, the fibrils did not bind and appeared to have no affinity for the α-sheet structure.

While these α-sheet peptides were not designed against a specific protein target, inhibition of aggregation was observed in two very different amyloid systems. These findings extend to many other sequences and a third independent amyloid system, as summarized in FIG. 5 and discussed further in Example 2. These results support the hypothesis that α-sheet structure is involved in the toxic oligomer stage of aggregation, and they provide a reference to determine spectroscopic signatures that can now be used to investigate the structural changes amyloid proteins undergo during amyloidosis. Having demonstrated that the α-sheet structure may constitute a broad-based inhibitor of amyloidosis, the α-sheet designs introduce a novel class of amyloid inhibitors that specifically target the toxic soluble oligomeric state of different amyloidogenic peptides and proteins.

REFERENCES AND NOTES

1. F. Chiti, C. M. Dobson, Amyloid formation by globular proteins under native conditions, *Nat. Chem. Biol.* 5, 15-22 (2009).
2. T. R. Jahn et al., The Common Architecture of Cross-β Amyloid, *Journal of Molecular Biology* 395, 717-727 (2010).
3. M. Bucciantini et al., Inherent toxicity of aggregates implies a common mechanism for protein misfolding diseases, *Nature* 416, 507-511 (2002).
4. J. Hardy. D. J. Selkoe, The amyloid hypothesis of Alzheimer's disease: progress and problems on the road to therapeutics, *Science* 297, 353-356 (2002).
5. J. L. Tomic, A. Pensalfini, E. Head, C. G. Glabe, Soluble fibrillar oligomer levels are elevated in Alzheimer's disease brain and correlate with cognitive dysfunction, *Neurobiology of Disease* 35, 352-358 (2009).
6. W.-F. Xue et al., Fibril fragmentation enhances amyloid cytotoxicity, *Journal of Biological Chemistry* 284, 34272-34282 (2009).
7. J. R. Silveira et al., The most infectious prion protein particles, *Nature* 437, 257-261 (2005).
8. R. A. Bodner et al., Pharmacological promotion of inclusion formation: a therapeutic approach for Huntington's and Parkinson's diseases, *Proc. Natl. Acad. Sci. U.S.A.* 103, 4246-4251 (2006).
9. R. Kayed et al., Common structure of soluble amyloid oligomers implies common mechanism of pathogenesis, *Science* 300, 486-489 (2003).
10. C. G. Glabe, R. Kayed, Common structure and toxic function of amyloid oligomers implies a common mechanism of pathogenesis, *Neurology* 66, S74-8 (2006).
11. R. S. Armen, D. O. V. Alonso, V. Daggett, Anatomy of an Amyloidogenic Intermediate: Conversion of β-Sheet to α-Sheet Structure in Transthyretin at Acidic pH, *Structure* 12, 1847-1863 (2004).
12. R. S. Armen, B. M. Bernard. R. Day, D. O. V. Alonso, V. Daggett, Characterization of a possible amyloidogenic precursor in glutamine-repeat neurodegenerative diseases, *Proc. Natl. Acad. Sci. U.S.A.* 102, 13433-13438 (2005).
13. R. S. Armen, M. L. DeMarco, D. O. Alonso, V. Daggett, Pauling and Corey's α-pleated sheet structure may define the prefibrillar amyloidogenic intermediate in amyloid disease, *Proc. Natl. Acad. Sci. USA* 101, 11622-11627 (2004).
14. R. E. Steward, R. S. Armen, V. Daggett, Different disease-causing mutations in transthyretin trigger the same conformational conversion, *Protein Engineering Design and Selection* 21, 187-195 (2008).
15. V. Daggett, α-Sheet: The Toxic Conformer in Amyloid Diseases? *Acc. Chem. Res.* 39, 594-602 (2006).
16. L. Pauling, R. B. Corey, The pleated sheet, a new layer configuration of polypeptide chains, *Proc. Natl. Acad. Sci. U.S.A.* 37, 251-256 (1951).

17. B. Di Blasio et al., A crystal structure with features of an antiparallel alpha-pleated sheet, *Biopolymers* 34, 1463-1468 (1994).
18. D. A. C. Beck, D. O. V. Alonso, D. Inoyama, V. Daggett, The intrinsic conformational propensities of the 20 naturally occurring amino acids and reflection of these propensities in proteins, *Proc. Natl. Acad. Sci. USA* 105, 12259-12264 (2008).
19. M. W. van der Kamp et al., Dynameomics: a comprehensive database of protein dynamics, *Structure* 18, 423-435 (2010).
20. P. De Santis, S. Morosetti, R. Rizzo, Conformational Analysis of Regular Enantiomeric Sequences, *Macromolecules* 7, 52-58 (1974).
21. F. Heitz, G. Detriche, F. Vovelle, G. Spach, Sheet structures in alternating poly (D, L-peptides), *Macromolecules* 14, 47-50 (1981).
22. D. A. C. Beck, M. McCully, D. O. V. Alonso, V. Daggett, In lucemn molecular mechanics (ilmm), Computer Program, University of Washington (2000-2013).
23. T. R. Foss, R. L. Wiseman, J. W. Kelly, The Pathway by Which the Tetrameric Protein Transthyretin Dissociates, *Biochemistry* 44, 15525-15533 (2005).
24. A. Quintas, M. J. Saraiva, R. M. Brito, The amyloidogenic potential of transthyretin variants correlates with their tendency to aggregate in solution, *FEBS Letters* 418, 297-300 (1997).
25. W. Colon, J. W. Kelly, Partial denaturation of transthyretin is sufficient for amyloid fibril formation in vitro, *Biochemistry* 31, 8654-8660 (1992).
26. A. G. Cochran et al., A Minimal Peptide Scaffold for β-Turn Display: Optimizing a Strand Position in Disulfide-Cyclized β-Hairpins, *J. Am. Chem. Soc.* 123, 625-632 (2001).
27. G. Yamin, P. Ruchala, D. B. Teplow, A Peptide Hairpin Inhibitor of Amyloid β-Protein Oligomerization and Fibrillogenesis. *Biochemistry* 48, 11329-11331 (2009).
28. J. Du, R. M. Murphy. Characterization of the Interaction of β-Amyloid with Transthyretin Monomers and Tetramers, *Biochemistry* 49, 8276-8289 (2010).
29. R. E. Koeppe et al., On the helix sense of gramicidin A single channels, *Proteins: Structure. Function, and Bioinformatics* 12, 49-62 (1992).
30. H. Torii, Amide I Infrared Spectral Features Characteristic of Some Untypical Conformations Appearing in the Structures Suggested for Amyloids, *J. Phys. Chem. B* 112, 8737-8743 (2008).
31. A. Barth, C. Zscherp, What vibrations tell about proteins, *Quart. Rev. Biophys.* 35, 369-430 (2002).
32. A. G. Cochran, N. J. Skelton, M. A. Starovasnik, Tryptophan zippers: stable, monomeric beta-hairpins, *Proc. Natl. Acad. Sci. U.S.A.* 98, 5578-5583 (2001).
33. R. Clark et al., Engineering stable peptide toxins by means of backbone cyclization; Stabilization of the alpha-conotoxin MII, *Proc. Natl. Acad. Sci. U.S.A.* 102, 13767-13772 (2005).
34. K. Wüthrich, in *NMR of Proteins and Nucleic Acids*, (Wiley, New York, 1986), pp. 162-176.
35. N. Carulla, M. Zhou, M. Arimon, M. Gairi, E. Giralt, C. V. Robinson, and C. M. Dobson, Experimental characterization of disordered and ordered aggregates populated during the process of amyloid fibril formation. *Proc. Natl. Acad. Sci. USA* 106, 7828-7833 (2009).
36. G. Bitan, E. A. Fradinger, S. M. Spring, D. B. Teplow, Neurotoxic protein oligomers-what you see is not always what you get. *Amyloid-J. of Prot. Fold. Disorders*, 12, 88-95 (2005).
37. M. Levitt, M. Hirshberg, R. Sharon, Potential energy function and parameters for simulations of the molecular dynamics of proteins and nucleic acids in solution, *Computer Physics Communications* (1995).
38. M. Levitt, M. Hirshberg, R. Sharon, K. Laidig, V. Daggett, Calibration and testing of a water model for simulation of the molecular dynamics of proteins and nucleic acids in solution, *J. Phys. Chem. B* 101, 5051-5061 (1997).
39. D. A. Beck, V. Daggett, Methods for molecular dynamics simulations of protein folding/unfolding in solution, *Methods* 34, 112-120 (2004).
40. W. E. Klunk. J. W. Pettegrew. D. J. Abraham, Two simple methods for quantifying low-affinity dye-substrate binding, *J. Histochem. Cytochem.* 37, 1293-1297 (1989).
41. N. Reixach, S. Deechongkit, X. Jiang, J. W. Kelly, J. Buxbaum, Tissue damage in the amyloidoses: Transthyretin monomers and nonnative oligomers are the major cytotoxic species in tissue culture, *Proc. Natl. Acad. Sci. USA* 101, 2817-2822 (2004).

Materials and Methods for Example 1

Computational Design

The α-sheet peptides were designed in silico using a database of amyloid protein MD simulations to determine preferred backbone geometries. The SLIRP database (18, 19) was used to select residues with high propensity to adopt the desired structure. MD simulations were performed to assess both turn and α-sheet stability. Ideal α-sheet and β-sheet templates were created and sequences were chosen based on their intrinsic conformational preferences and to consist of a mix of polar and nonpolar amino acids to maintain good inter-strand interactions and solubility. Intrinsic conformational propensities of all 20 L-amino acids in a GGXGG (SEQ ID NO: 3) peptide were determined by extensive molecular dynamics (MD) simulations (18). D-amino acid propensities were determined in a similar manner (unpublished results). MD simulations were then performed to assess the stability of the designs. Multiple short simulations were performed, at least 3×20 ns, for each peptide at 25° C. using an in-house MD package in lucem molecular mechanics (ilmm) (22), with the Levitt et al. all atom force field (37) and the F3C water model (38). Standard simulation protocols were followed (39). α-Sheet stability was assessed by monitoring both the secondary structure and the turn structure, based on hydrogen bonding over the duration of the simulations. Results were expressed as the fraction of simulation time the atoms were within hydrogen bonding distance. Cα RMSD was used qualitatively to monitor backbone deviation from the ideal hairpin structure in conjunction with the hydrogen bond scoring function to determine promising designs. An iterative approach was used, with the results of the analyses used to modify and refine sequences for further simulation and evaluation. Several sequences were chosen from a pool of well-behaved simulations for experimental evaluation. High scoring designs were synthesized and their inhibitory effects were determined in TTR and Aβ fibrillization assays at 20- or 10-fold molar excess of inhibitor, respectively.

TTR Fibrillization Assay

Aliqouts of transthyretin (TTR) (496-11; Lee Biosolutions, St. Louis Mo.) were made from a 1 mg/mL solution 20 mM ammonium carbonate, pH 8. Aliquots were lyophilized and stored at −18° C. Prior to use, TTR was dissolved to 80 μM (monomer) in acetate buffer (50 mM potassium acetate, 100 mM potassium chloride pH 4.5) and sonicated for 10 minutes. The stock solution was centrifuged before use. Peptide designs were added to stock TTR to a final TTR concentration of 40 µM (monomer) in acetate buffer (pH 4.5) in 500 µL microcentrifuge tubes, which were incubated at 37° C. Periodically, samples were collected from the TTR:peptide mixture by briefly centrifuging, and then carefully pipetting the solution up and down prior to withdrawing a 10 µL sample and diluting it in 190 µL of 10 µM Congo red in an individual well of a 96-well assay plate. Each measurement was performed in triplicate. Absorbance measurements were taken at 477 and 540 nm. Relative Congo red binding was determined using the method of Klunk et al. using the relationship: $rCb=(Abs_{540}/25,295)-(Abs_{477}/46,306)$ (40). All datapoints were normalized to the value recorded for TTR alone pH 4.5 at 48 hrs.

Aβ Fibrillization Assay.

Aβ (1-42) (AMYD-002; CPC Scientific, Sunnyvale Calif.) was stored as 2 mg/mL stock in hexafluoroisopropanol (HFIP) at −18° C. Prior to use, the stock solution was thawed, an aliquot taken and the HFIP was removed under a gentle stream of air. A 1 mg/mL stock solution of Aβ was made in 5 mM NaOH and sonicated for 5-10 minutes. The stock was filtered through a 0.22 µm cellulose filter (Costar Spin-X; Corning Inc, NY). The concentration of stock Aβ was determined by first diluting the stock 1:50 in 5 mM NaOH then taking the absorbance at 220 nm ($\epsilon_{220}$=50,000 $cm^{-1}$ $M^{-1}$). Aliquots of the NaOH stock were placed in separate wells of a 96-well black-walled fluorescence plate (Nunc) and immediately diluted in PBS (11 mM phosphate) containing 20 µM Thioflavin T (ThT) to give 150 µL of 10 µM Aβ at pH 7.5. Peptide inhibitors were added directly to 10 µM Aβ samples from concentrated aqueous stocks. Covered plates were incubated at 37° C. and were periodically removed for fluorescence measurements. ThT fluorescence was measured at $\lambda_{ex}$=450 nm and $\lambda_{em}$=480 nm using a Tecan Safire2 plate reader.

Immobilization and Solution Binding

Peptide designs were immobilized to the Pierce Amino Link resin following the manufacturer's instructions. Peptides were immobilized in a volume of 200 µL of coupling buffer (100 mM sodium phosphate, 150 mM sodium chloride, pH 7.2) and 2 µL cyanoborohydride solution (5 M sodium cyanoborohydride in 1 M NaOH) at a concentration of 358 µM overnight at 4° C. Any residual active sites were blocked with 400 µL quenching buffer (1 M tris hydrochloride, pH 7.4) and 4 µL cyanoborohydride solution for 4 hours at 25° C. Binding experiments were performed from 200 µL amyloid solution (5 µM Aβ or 20 µM TTR (monomer) diluted to the desired concentration in coupling buffer), which was allowed to bind to the peptide-bound agarose beads for 2 h at 25° C. The solution was then collected by centrifugation (flow through, FT). The beads were resuspended in 300 µL coupling buffer, vortexed to obtain an uniform slurry, and the solution was again collected by centrifugation (wash 1, W1). The wash step was performed an additional five times (W2-W6). One final wash step was performed but after resuspending the resin, the solution was allowed to sit for 5 minutes before centrifugation (W7). The resin was next resuspended in 100 µL 2M guanidine hydrochloride, incubated for 5 minutes at room temperature, then collected as before. This was performed twice (E1-E2). The resin was washed again with 300 µL coupling buffer (W8) followed by two elution steps with 6M guanidine hydrochloride (E3-E4). One final wash step was performed with 300 µL coupling buffer (W9). All collected eluents were analyzed by applying triplicate 1 µL spots to nitrocellulose, and then performing standard dot blot analysis as described by Kayed et al. (9) with an anti-TTR (sc-13098, Santa Cruz Biotechnology, Santa Cruz, Calif.) or anti-Aβ (ab39377; Abeam Inc, Cambridge, Mass.) primary antibody diluted 1:1.000 in 5% or 10% nonfat milk, respectively.

SH-SY5Y Cell Viability

The toxicity of aggregates was tested against the human neuroblastoma cell line SH-SY5Y in an MTT cell viability assay. The human neuroblastoma cell line SH-SY5Y (CRL-226; American Type Culture Collection) was grown in 75 $cm^2$ flasks in 1:1 DMEM/F12 (CellGro) supplemented with 10% FBS and 50 units/mL penicillin/50 µg/mL streptomycin (complete media), and incubated at 37° C. in humidified 5% $CO_2$ environment. Cells were routinely passaged when they reached 90% confluence by addition of trypsin (Gibco) and replated at a ratio of 1:10 in complete media. Cells were plated to a density of 25,000 cells/well in a 96-well plate (100 µL/well) and allowed to attach overnight. The cell assay was performed as described by Reixach et al. (41).

CD Spectroscopy

Far UV CD spectra were recorded on an Aviv model 420 spectrometer (Aviv Biomedical) over 190-260 nm in a 1 mm quartz cuvette. All samples were prepared at 100 µM in 50 mM phosphate, 100 mM KCl buffer, pH 5.8, and were recorded at 25° C. with a resolution of 0.5 nm, a scan speed of 20 nm/min, and a 2 nm bandwidth. Average values from three scans were plotted using the Origin 8 software (Originlab, Northhampton, Mass.). All spectra were smoothed using the Savitzky-Golay method with 5-12 points/window, and polynomial order 2.

FTIR Spectroscopy

IR spectra were obtained using a Perkin-Elmer Spectrum 100 instrument equipped with a diamond attenuated total reflectance sample unit and an MCT detector. Peptide samples were pelleted and resuspended as a 1-2 µl slurry. The slurry was applied to the diamond and dried to a film over a few minutes while following the disappearance of the broad liquid water band at ~1636 $cm^{-1}$ and the appearance of the protein amide I and amide II bands. The spectra were background-subtracted and comprised of 64 accumulations (4 $cm^{-1}$ resolution; 1 cm/sec OPD velocity; strong apodization). Spectra shown here were recorded as soon as successively collected spectra (each recorded over 80 sec) stabilized, indicating little further evaporation of liquid water. This approach was taken to essentially eliminate spectral contributions from free liquid water without desiccating the peptide film any more than necessary. Second derivative spectra were calculated using the instrument software and 13 data points.

NMR Spectroscopy

Peptides were prepared in 50 mM potassium phosphate buffer containing 100 mM KCl pH 5.8. All NMR experiments were performed on Bruker Avance 600 and/or 500 MHz spectrometers equipped with cryogenic triple resonance probes. The sample temperature was kept at 25° C. 4,4-dimethyl-4-silapentane-1-sulfonic acid (DSS) was used for proton chemical shift referencing whereas indirect referencing was used for carbon and nitrogen. The resonance assignments for peptides were carried out using $^1H$-$^1H$ TOCSY and [$^1H$-$^1H$] NOESY spectra recorded in 90% $H_2O$ and 10% $^2H_2O$. The assignments thus obtained are translated onto the natural abundance $^1H$-$^{15}N$ HSQC and $^1H$-$^{13}C$ HSQC spectra. All spectra were processed with Topspin3.0 (Bruker) and analyzed using CARA (see web site cara.nm-

Example 2. α-Sheet Structure not Specific Amino Acid Sequences Dictate Inhibition Three α-sheet designs are addressed in Example 1, but many more have been evaluated using these same assays and structural methods. FIG. 5 contains a list of other designed α-sheet peptides, both linear and cyclic (specifically peptides #3-5 and #8-9), as well as other control, non-α-sheet designs (peptides #17-18, 20). In addition, FIG. 5 contains 'control' designs aimed at reverse engineering the α1 design, which is presented in more detail in Example 3. FIG. 5 provides evidence that the primary amino acid sequence of the polypeptides does not per se dictate the inhibitory activity (here defined as inhibition of aggregation and/or binding of toxic oligomer). Instead it is the ability of the polypeptides to adopt a stable α-sheet structure that is operative, which is achieved through the recited polypeptide generic structure and the recited arrangement of alternating D/L amino acids. Random primary sequences of amino acids are active in the polypeptides of the invention; these same primary sequences are not active if the polypeptide is provided in an entirely L-amino acid peptide or if the L/D amino acids are randomly distributed within the polypeptide such that they are not alternating (i.e. if they are not polypeptides according to the invention). As noted in FIG. 5:

- An all L-amino acid peptide (llas90, peptide #20, Control9) with the same amino acid sequence as ldas90 (peptide #1) does not form α-sheet and is inactive. The two peptides have 100% sequence identity and 100% composition match.
    - Thus, the primary amino acid sequence alone does not determine activity; it is the L/D patterning of the sequence that is critical.
- All L/D alternating hairpin peptides investigated experimentally to date form α-sheet structure (see, for example, peptides #1-14). They also all inhibit aggregation and/or bind the toxic oligomer. Some of the polypeptides are insoluble and the solution assay can't be performed, but they do bind the targeted toxic oligomer when they are immobilized to agarose beads to promote solubilization.
    - Thus, this provides further evidence that the primary amino acid sequence per se is not determining structure and activity, the L/D patterning is. However, the sequence modulates the activity and solubility properties.
- Both cyclic and linear designs with different sequences form α-sheet polypeptides, inhibit aggregation, and bind the toxic oligomer. (See peptides #1-#13.)
    - This provides further evidence that inhibitory behavior is determined by L/D patterning, not by primary amino acid sequence or the nature of the polypeptide turns.
- Both charged N- and C-termini and neutral capped termini versions of ldas90 adopt α-sheet structure and demonstrate activity. (See peptides #1 and #7.) Note, however, that the charges can modulate the level of activity.
- Next, consider all 14 designed peptides with the L/D turn template, they are all active. Some have issues with solubility but they all form α-sheet and are active amyloid inhibitors in solution and/or binding of the toxic oligomer. These designs are both linear and cyclic peptides designed to be hairpins. The sequence identity relative to ldas90 (peptide #1) ranges from 9-91% across these 14 designs with an average of 43%. Hence, these are different compounds and they show that conventional rules about composition and matter based on amino acid sequence don't hold for this situation. Instead all sequences tried in an L/D template form α-sheet and are active.
- Finally, there are 6 peptides with the same amino acid composition (100% composition match) (peptides #1, 6, 7, 12, 19 and 20) (FIG. 5 and Table 1).
    - Two of these have 100% sequence identity and have alternating L/D amino acids (ldas90: #1 and #7) but one has charged termini and the other has capped termini (N-acetylated and C-amidated). They both form α-sheet and are active in inhibiting aggregation and binding toxic oligomer.
    - The all L-amino acid version of ldas90 (llas90, or control9, peptide #20) has 100% sequence identity, but it doesn't form α-sheet and it's inactive.
    - Control5 (peptide #6) has the ldas90 turn and the tails but the amino acids in the L/D strands were shuffled and randomized while maintaining the L/D patterning. This peptide adopts α-sheet structure and is active.
    - Control6 (peptide #12) has the ldas90 (peptide #1) GR tails (X1 and X5) and the L/D patterning but all the positions aside from the tails are randomized. The sequence composition is 100% and the sequence identity is 25%. This peptide forms α-sheet and is active.
    - Control2 (peptide #19) has 24% sequence identity with ldas90 (peptide #1) and all positions were randomized and the L/D patterning was not imposed. This peptide does not form α-sheet and it is inactive.

Example 3. Reverse Engineering of α1: Sequence Modifications and Effects on Structural Stability and Inhibition To determine the effects of sequence modifications on structure and function of the α-sheet, the α1 ldas90 peptide (peptide #1) was reverse engineered by successively modifying or eliminating stabilizing design features, including amino acid sequence of the strands, turns, and alternation of L- and D-amino acids. These "control" peptides' primary sequences, all applicable names, identity relative to α1, and the modifications that gave rise to each peptide are listed in Table 1 and ordered in terms of decreasing sequence identity to ldas90, α1, in the L/D template group.

Moving down Table 1, Control5 (peptide #6) has the ldas90 L/D template, the ldas90 amino acid composition, the same relative chirality (i.e. the L/D patterning, or relative positions of the L and D residues in the sequence), and 65% sequence identity through scrambling of the amino acids in the two α-strands. Control6 (peptide #12) takes this a step further with scrambling of the strands and the intervening turn, resulting in 25% sequence identity while retaining 100% of the sequence composition of ldas90. Control3 (peptide #11) has the alternating D/L template but with a completely random sequence, resulting in 16% sequence identity. Control4 (peptide #13) is the same, it retains the L/D patterning but has a completely random sequence, this time resulting in 9% sequence identity. Two non-LID template controls are provided. Control2 (peptide #19) has the ldas90 (peptide #1) amino acid composition but everything is scrambled, resulting in 24% sequence identity. Finally, Control9 (or llas90, peptide #20) is a completely L-amino acid version of ldas90. It has 100% sequence identity with ldas90 and 74% chirality in common with ldas90 (i.e. 74% represents the matching of the L-amino acids in the two peptides). The llas90 and ldas90 peptides are identical in chemical terms aside from the stereochemistry.

The results are summarized in Table 1; all peptides containing the L/D template form α-sheet (peptides #1, 6, 12, 11, and 13), while those lacking the alternating D/L amino acids do not (peptides #19, 20).

TABLE 1

α-sheet structure determines inhibitory properties not sequence

| Peptide # in Figure 5 | Design | Sequence | % sequence identity relative to ldas90 | % sequence composition relative to ldas90 | % chirality relative to ldas90 | Description | Inhibits Aggregation and/or binds oligomer? | Contains α-sheet Structure? |
|---|---|---|---|---|---|---|---|---|
| Designs containing alternating L/D amino acids for templated α-sheet structure ||||||||||
| 1 | ldas90, α1 | Ac-RGEmNiS wMNEYSGWt M nLkMGR-NH2 | 100 | 100 | 100 | Parent Design | yes | yes |
| 6 | Control 5 | Ac-RGNwNeS kMNEYSGWmL mLtMGR-NH2 | 65 | 100 | 100 | Scrambled α-strand sequences of ldas90 (res. 3-9 and 15-21) | yes | yes |
| 12 | Control 6 | Ac-RGEaWmY iKNNLSETmM sNmWGR-NH2 | 25 | 100 | 100 | Scrambled sequences through α-strands and turn of ldas90 (res. 3-21) | yes | yes |
| 11 | Control 3 | Ac-AQQiEcI tNVWDKEItM yFnVSE-NH2 | 16 | 43 | 100 | Random sequence selection, L/D template maintained | yes | yes |
| 13 | Control 4 | Ac-WRPwAiD gMNTBKQRkA sVyLQP-NH2 | 9 | 52 | 100 | Random sequence selection, L/D template maintained | yes | yes |
| Designs lacking alternating L/D α-sheet template ||||||||||
| 19 | Control 2 | Ac-MNWESkG EwIRMRYGtm LSNGnM-NH2 | 24 | 100 | 65 | Scrambled sequence and chirality of ldas90, no L/D template | no | no |
| 20 | llas90, Control 9 | Ac-RGEMNLS WMNEYSGWTM NLKMGR-NH2 | 100 | 100 | 74 | All L-amino acid version of ldas90 | no | no |

From top to bottom SEQ ID NOs: 158, 91, 151, 152, 153, 147, 70

The "control" designs in Table 1 were evaluated using circular dichroism (CD) and Fourier Transform Infrared (FTIR) absorbance spectroscopy, carried out as described in Example 1. For hairpin peptides exhibiting stable α-sheet secondary structure, relatively flat CD spectra are expected, with some negative signal at 195-200 nm due to the turns (X3) and RG tails (X1 and X5) (both of which include only L-amino acids). Characteristic "random coil" CD signal for L-amino acids occurs at 195-200 nm. α-sheet secondary structure is expected to give FTIR bands at 1680 $cm^{-1}$ and 1640 $cm^{-1}$. Both CD and FTIR spectroscopy are well-established techniques for secondary structure elucidation.

Figures 6A, 6B:
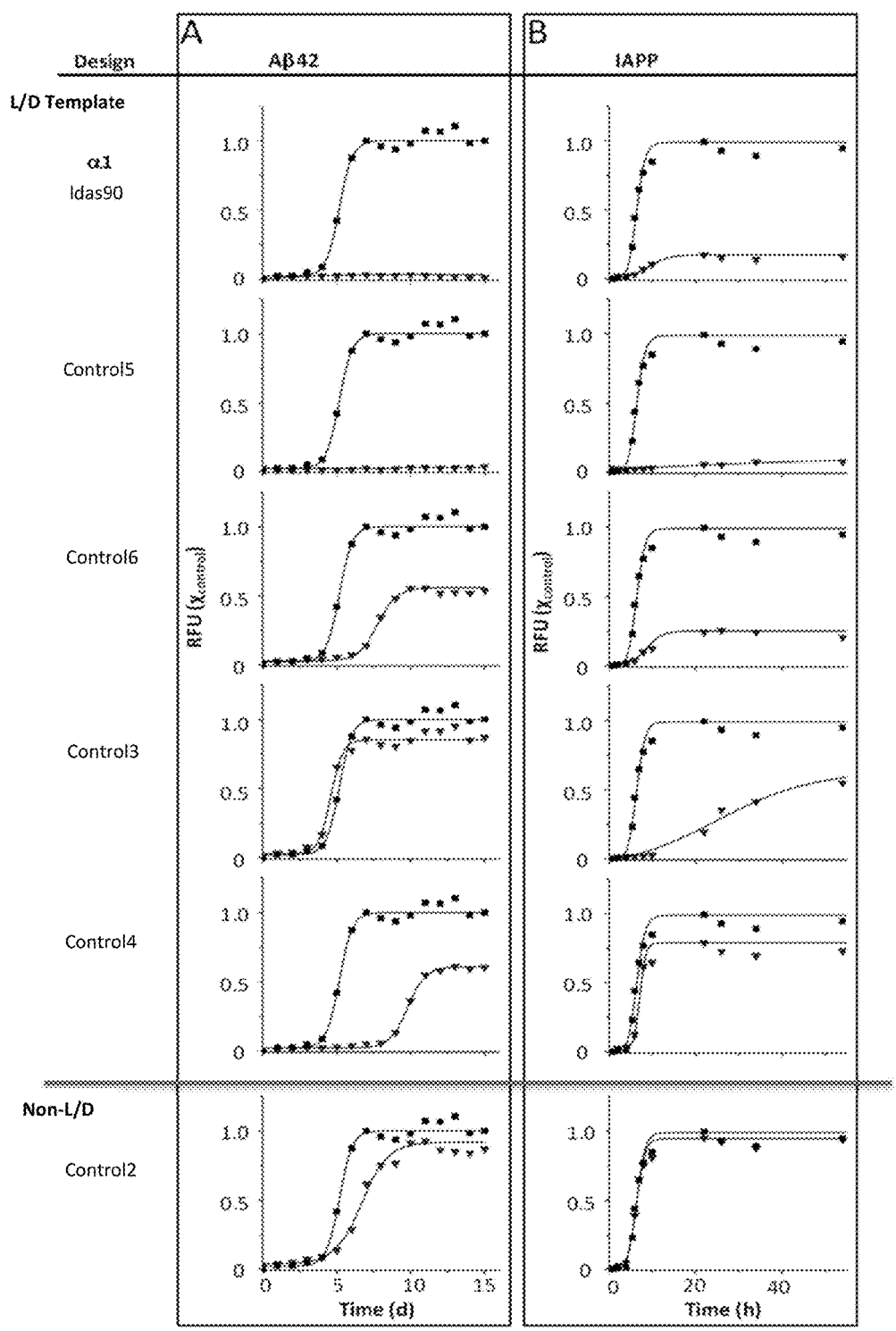
FIG. 6A-C. Graphs showing inhibitory properties of polypeptides of the invention against Amyloid β 1-42 peptide (Aβ42 or Aβ) (panel A), islet amylin polypeptide (IAPP) (panel B), and transthyretin (TTR) (panel C) amyloidosis. Aggregation is tracked over time using ThT or Congo Red without inhibitor in black and addition of inhibitor (colored traces) leads to a drop in aggregation. Inhibitory activity was observed for all peptides featuring alternating L- and D-amino acids.
Figure 6C:
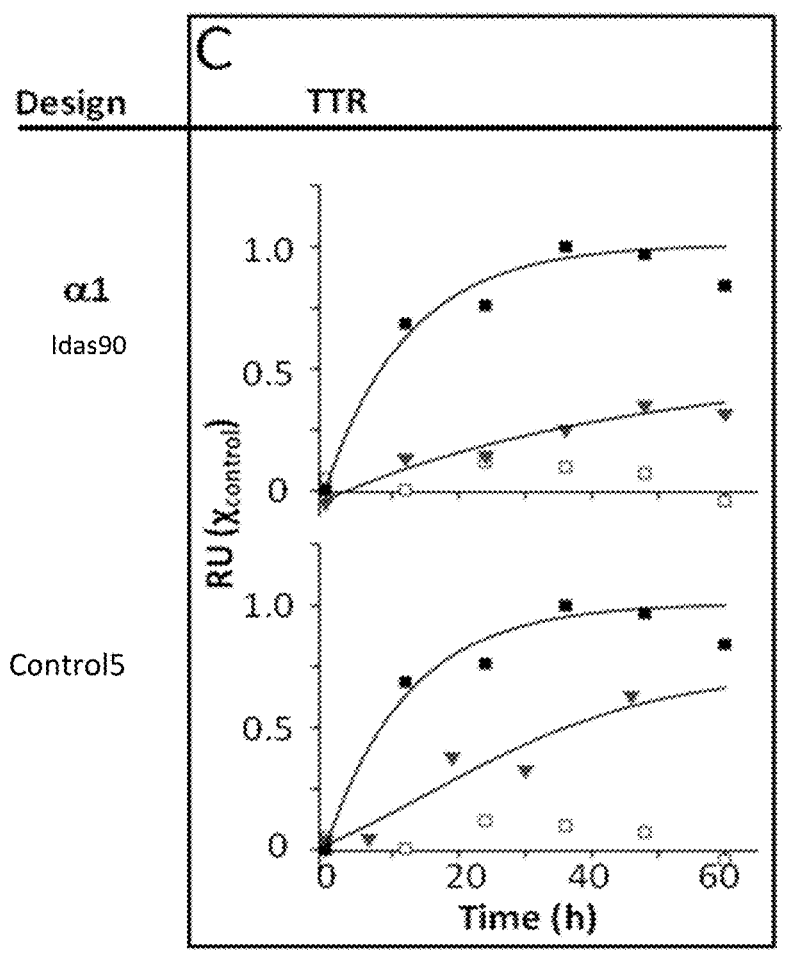

The "control" designs were tested as general inhibitors against the Amyloid β 1-42 peptide (Aβ) (panel A), the islet amylin polypeptide (IAPP, or amylin, which is implicated in type 2 diabetes) (panel B), and transthyretin (TTR) (panel C) amyloidosis (FIG. 6). Inhibitory activity was observed for all peptides featuring alternating L- and D-amino acids. As described in Example 1, a Thioflavin T (ThT) fluorescence assay was used to monitor Aβ and IAPP aggregation. A Congo Red dye-binding assay was used to monitor TTR fibrillization. For inhibition against Aβ, peptides were co-incubated at 4-fold excess of Aβ at RT in neutral pH buffer containing ThT. Note that the results for α1 differ somewhat from what are included in Example 1 because the assay conditions were altered slightly to slow the process down to favor oligomerization of Aβ (rather than fibril elongation) by lowering the temperature to 25° C. The advantages of these systematic changes are evident in FIG. 6: inhibitory activity is improved to the extent that α1 quenches Aβ aggregation at only a 4-fold excess. For inhibition against IAPP, peptides were co-incubated at 8-fold excess of IAPP at 37° C. in neutral pH buffer containing 20 μM ThT. For inhibition against TTR, peptides were co-incubated at 10-fold excess of monomeric TTR. Note that several of the controls bind Congo Red so their inhibitory properties in solution against TTR could not be assessed (Controls 6, 3, 4 and 2), but the α-sheet designs (Controls 6, 3, and 4) do bind toxic oligomer when immobilized while Control 2 does not (Table 1 and FIG. 5).

The data in FIG. 6 were normalized to ThT fluorescence of the negative (uninhibited) control (black squares). Inhibition traces are ordered vertically according to sequence identity to α1 (see Table 1). Sigmoidal fits to data are included. Controls are identical throughout a single panel, and traces for inhibition samples are colored while the uninhibited aggregation profiles are in black. All of the alternating L/D designs inhibit aggregation (although Control 3 is weak) (FIG. 6) and bind the toxic oligomer when immobilized (Table 1), while the non-L/D controls do not inhibit amyloidosis nor do they bind the oligomer.

To investigate the effect of randomizing the amino acids within the two α-strands of ldas90 (peptide #1) a control was investigated in which the residues in the turn (X3) and at the ends of the peptide (X1 and X5) were held constant and the amino acids in the strands were scrambled (peptide #6. Control5). The overall identity in amino acid composition between the polypeptides was 100% but the resulting primary amino acid sequence identity dropped to 65%. Despite having a random sequence in the strands, peptide #6 is a good inhibitor and it binds the toxic oligomer. In fact, this control with scrambled strands is as good as ldas90 (peptide #1) with capped ends and it is better than ldas90 with charged ends (peptide #7).

Control6 (peptide #12) takes the randomization of ldas90 a step further and maintains the GR ends (X1 and X5) but randomizes the strands and turn (X3-X4-X5). The primary amino acid sequence identity drops to 25% while the composition remains at 100%. The scrambling of 75% of the sequence still yields an α-sheet structure and an active peptide: it inhibits aggregation and binds the toxic oligomer. Again this shows that the alternating L/D patterning is critical for activity of the polypeptides of the invention, not the primary amino acid sequence per se.

Taking this a step further, Controls 3 and 4 (peptides #11 and #13) are totally random sequences on the L/D strand-turn-L/D strand template. These peptides have 16 and 9% sequence identity to ldas90 (peptide #1), respectively. Both of these peptides adopt α-sheet structure and are active and prevent aggregation in solution and/or bind the toxic oligomer.

Figure 7:
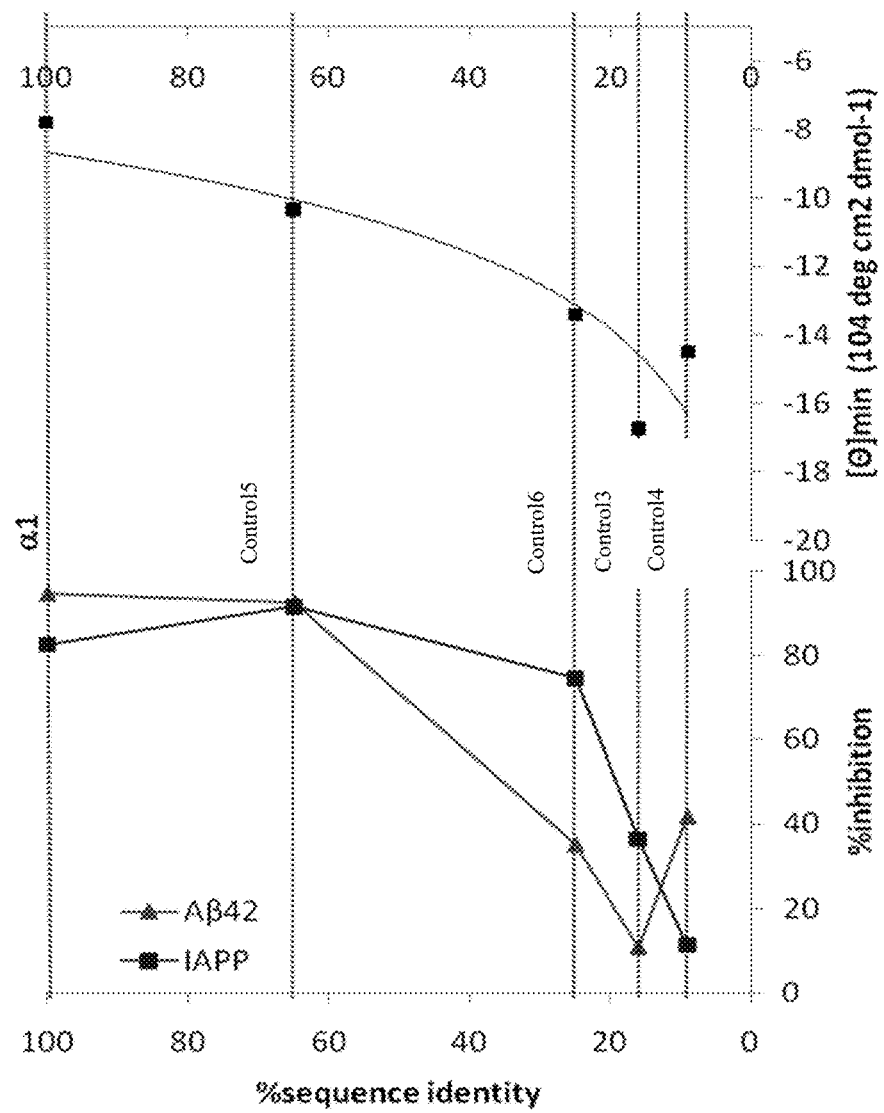
FIG. 7. Graph summarizing the inhibitory activity and "random coil"-character for exemplary polypeptides of the invention plotted against their sequence identity relative to the α1, ldas90 polypeptide. The top y-axis reflects the random coil character as reflected in the CD minimum at ~195-198 nm and that axis should read $[\theta]_{min}$ ($10^4$ deg cm$^2$ dmol$^{-1}$].

All of the L/D template designs are active but as the sequence is modified and the structure is destabilized with concomitant increasing random coil content (indicated by decreasing $[\theta_{min}]$ at 195 nm), inhibition drops. FIG. 7 illustrates the correlation between destabilization of the α-sheet structure, as measured through the increasing random coil signal, and drop in inhibitory potency as the sequence becomes increasingly randomized. All of the L/D template designs are active, even with random sequences through the stands, with some as active (for example Control5, peptide #6) as the parent design, ldas90 (peptide #1). Thus, the sequence per se does not determine inhibition and oligomer binding, the alternating L/D amino acids giving rise to the α-sheet structure direct inhibitory behavior. But, the sequence modulates the stability and some sequences lead to more stable α-sheets than others and more stable α-sheets yield more potent inhibitors of aggregation.

We claim:
1. An isolated polypeptide, comprising 12-23 contiguous amino acids according to the general formula X1-X2-X3-X4-X5 (SEQ ID NO: 1), wherein
X1 is 0-7 contiguous amino acid residues that do not alternate between L and D residues;
X2 is 5-9 contiguous amino acid residues alternating between D amino acids and L amino acids;
X3 is 3-5 contiguous amino acid residues that do not alternate between L and D residues and do not abut residues with an alternative chirality;
X4 is 4-12 contiguous amino acid residues alternating between D amino acids and L amino acids; and
X5 is 0-4 contiguous amino acid residues that do not alternate between L and D residues;
wherein the isolated polypeptide is not: RGE(m)N(l)S(w)MNEYSGW(t)M(n)L(k)MGR (SEQ ID NO: 2).

2. The isolated polypeptide of claim 1, wherein X1 is 0-2 contiguous amino acid residues that do not alternate between L and D residues.

3. The isolated polypeptide of claim 1, wherein X2 is 6-8 contiguous amino acid residues alternating between D amino acids and L amino acids.

4. The isolated polypeptide of claim 1, wherein X4 is 6-12 contiguous amino acid residues alternating between D amino acids and L amino acids.

5. The isolated polypeptide of claim 1, wherein X5 is 0-3 contiguous amino acid residues that do not alternate between L and D residues.

6. The isolated polypeptide of claim 1, wherein at least one of the following is true:
(a) X1 is 0 or 1 amino acid;
(b) X2 is 5, 6, 8, or 9 contiguous amino acid residues alternating between D amino acids and L amino acids;
(c) X4 is 6, 8, 9, 10, 11, or 12 contiguous amino acid residues alternating between D amino acids and L amino acids; or
(d) X5 is 0, 1, 3, or 4 contiguous amino acid residues that do not alternate between L and D residues.

7. The isolated polypeptide of claim 1, wherein
X1 is absent;
X2 is 5-7 contiguous amino acid residues alternating between D amino acids and L amino acids;
X3 is 3-5 contiguous amino acid residues that do not alternate between L and D residues and do not abut residues with an alternative chirality;
X4 is 6-11 contiguous amino acid residues alternating between D amino acids and L amino acids; and
X5 is 0 or 1 amino acid residue.

8. The isolated polypeptide of claim 1, wherein
X1 is absent;
X2 is 7 contiguous amino acid residues alternating between D amino acids and L amino acids;
X3 is 3 contiguous amino acid residues that do not alternate between L and D residues;
X4 is 9 contiguous amino acid residues alternating between D amino acids and L amino acids; and
X5 is absent.

9. The isolated polypeptide of claim 1, wherein
X1 is absent;
X2 is 8 contiguous amino acid residues alternating between D amino acids and L amino acids;
X3 is 3 contiguous amino acid residues that do not alternate between L and D residues;
X4 is 10 contiguous amino acid residues alternating between D amino acids and L amino acids; and
X5 is absent.

10. The isolated polypeptide of claim 1, wherein
X1 is 2 contiguous amino acid residues that do not alternate between L amino acids and D amino acids;
X2 is 7 contiguous amino acid residues alternating between D amino acids and L amino acids;
X3 is 3 contiguous amino acid residues that do not alternate between L and D residues;
X4 is 9 contiguous amino acid residues alternating between D amino acids and L amino acids; and
X5 is 2 contiguous amino acid residues that do not alternate between L amino acids and D amino acids.

11. The isolated polypeptide of claim 1, wherein
X1 is absent;
X2 X7 is 7 contiguous amino acid residues alternating between D amino acids and L amino acids;
X3 is 4 contiguous amino acid residues that do not alternate between L and D residues;
X4 is 8 contiguous amino acid residues alternating between D amino acids and L amino acids; and
X5 is absent.

12. The isolated polypeptide of claim 1, wherein X2 and X4 are the same length.

13. The isolated polypeptide of claim 12, wherein
X1 is absent;
X2 is 7 contiguous amino acid residues alternating between D amino acids and L amino acids;
X3 is 5 contiguous amino acid residues that do not alternate between L and D residues;
X4 is 7 contiguous amino acid residues alternating between D amino acids and L amino acids; and
X5 is absent.

14. The isolated polypeptide of claim 1, wherein
X1 is absent;
X2 is 6 contiguous amino acid residues alternating between D amino acids and L amino acids;
X3 is 3 contiguous amino acid residues that do not alternate between L and D residues and do not abut residues with an alternative chirality;
X4 is 11 contiguous amino acid residues alternating between D amino acids and L amino acids; and
X5 is 1 amino acid residue.

15. The isolated polypeptide of claim 1, wherein
X1 is absent;
X2 is 6 contiguous amino acid residues alternating between D amino acids and L amino acids;
X3 is 3 contiguous amino acid residues that do not alternate between L and D residues;
X4 is 10 contiguous amino acid residues alternating between D amino acids and L amino acids; and
X5 is 1 amino acid residue.

16. The isolated polypeptide of claim 1, wherein
X1 is absent;
X2 is 8 contiguous amino acid residues alternating between D amino acids and L amino acids;
X3 is 3 contiguous amino acid residues that do not alternate between L and D residues;
X4 is 12 contiguous amino acid residues alternating between D amino acids and L amino acids; and
X5 is absent.

17. The isolated polypeptide of claim 1 according to the general formula
R1-R2-R3-R4-R5-R6-R7-R8-R9-R10-R11-R12-R13-R14-R15-R16-R17-R18-R19-R20-R21-R22-R23 (SEQ ID NO: 119), wherein at least residues R1-R14 are present in the isolated polypeptide, and wherein
R1 is selected from the group consisting of S, (q), (l), (w), (e), and (k), or their reverse chiral counterparts;

R2 is selected from the group consisting of (l), Q, W, E, (d), and (n), or their reverse chiral counterparts;
R3 is selected from the group consisting of T, (k), (l), (q), and S, or their reverse chiral counterparts;
R4 is selected from the group consisting of (l), S, Q, (w), (n), and F, or their reverse chiral counterparts;
R5 is selected from the group consisting of D, (w), (l), and T, or their reverse chiral counterparts;
R6 is selected from the group consisting of (p), T, S, N, and W, or their reverse chiral counterparts;
R7 is selected from the group consisting of N, (w), and A, or their reverse chiral counterparts;
R8 is selected from the group consisting of R, A, T, and E, or their reverse chiral counterparts;
R9 is selected from the group consisting of (l), A, N, and Y, or their reverse chiral counterparts;
R10 is selected from the group consisting of T, A, S, and Y, or their reverse chiral counterparts;
R11 is selected from the group consisting of (l), (a), P, R, and W, or their reverse chiral counterparts;
R12 is selected from the group consisting of K, W, A, and (t), or their reverse chiral counterparts;
R13 is selected from the group consisting of (p), (t), (a), and M, or their reverse chiral counterparts;
R14 is selected from the group consisting of P, M, W, (q), E, and C, or their reverse chiral counterparts;
R15 is selected from the group consisting of (q), (t), and L, or their reverse chiral counterparts, or is absent;
R16 is selected from the group consisting of L, W, Q, P, (k), and C, or their reverse chiral counterparts, or is absent;
R17 is selected from the group consisting of (k), (w), (l), (q), (p), and E, or their reverse chiral counterparts, or is absent;
R18 is selected from the group consisting of E, D, L, and P, or their reverse chiral counterparts, or is absent;
R19 is selected from the group consisting of (p), (k), and N, or their reverse chiral counterparts, or is absent;
R20 is selected from the group consisting of N, Q, and K, or their reverse chiral counterparts, or is absent;
R21 is selected from the group consisting of K, R, and (q), or their reverse chiral counterparts, or is absent;
R22 is P, or its reverse chiral counterpart, or is absent; and
R23 is (p), or its reverse chiral counterpart, or is absent.

18. An isolated polypeptide, comprising at least 14 contiguous amino acids according to the general formula R1-R2-R3-R4-R5-R6-R7-R8-R9-R10-R11-R12-R13-R14-R15-R16-R17-R18-R19-R20-R21-R22-R23 (SEQ ID NO: 119), wherein at least residues R1-R14 are present in the isolated polypeptide, and wherein
R1 is selected from the group consisting of S, (q), (l), (w), (e), Q, and (k);
R2 is selected from the group consisting of (l), Q, W, L, E, (d), and (n);
R3 is selected from the group consisting of T, (k), (l), (q), and S;
R4 is selected from the group consisting of (l), S, Q, (w), (n), and F;
R5 is selected from the group consisting of D, (w), (l), and T;
R6 is selected from the group consisting of (p), T, S, N, and W;
R7 is selected from the group consisting of N, (w), and A;
R8 is selected from the group consisting of R, A, T, and E;
R9 is selected from the group consisting of (l), L, A, N, and Y;
R10 is selected from the group consisting of T, (t), A, (a), S, and Y;
R11 is selected from the group consisting of (l), L, (a), P, A, R, and W;
R12 is selected from the group consisting of K, (k), W, A, and (t);
R13 is selected from the group consisting of (p), (t), (a), and M;
R14 is selected from the group consisting of P, M, W, (q), E, and C;
R15 is selected from the group consisting of (q), (t), and L, or is absent;
R16 is selected from the group consisting of L, W, Q, P, (k), and C, or is absent;
R17 is selected from the group consisting of (k), (w), (l), (q), (p), P, and E, or is absent;
R18 is selected from the group consisting of E, D, L, (p), and P, or is absent;
R19 is selected from the group consisting of (p), (k), and N, or is absent;
R20 is selected from the group consisting of N, Q, and K, or is absent;
R21 is selected from the group consisting of K, R, and (q), or is absent;
R22 is P, or is absent; and
R23 is (p), or is absent.

19. A pharmaceutical composition, comprising:
(a) the isolated polypeptide of claim 1; and
(b) a pharmaceutically acceptable carrier.

20. A method for treating an amyloid disease, comprising administering to a subject with an amyloid disease an amount of the isolated polypeptide of claim 1 effective to treat the amyloid disease.

21. A method for diagnosing or prognosing an amyloid disease, comprising
(a) contacting a tissue sample from a subject at risk of having an amyloid disease with the isolated polypeptide of claim 1, under conditions suitable for binding of the isolated polypeptide with an amyloid intermediate, if present in the tissue sample, to produce a binding complex;
(b) detecting binding complexes in the tissue sample; and
(c) diagnosing or prognosing an amyloid disease based on the detecting.

* * * * *

SEQUENCE LISTING

```
<160> NUMBER OF SEQ ID NOS: 158

<210> SEQ ID NO 1
<211> LENGTH: 37
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(7)
<223> OTHER INFORMATION: Xaa is any amino acid or is optionally absent
      and contiguous amino acid residues do not alternate between L and
      D residues
<220> FEATURE:
<221> NAME/KEY: MISC_FEATURE
<222> LOCATION: (8)..(12)
<223> OTHER INFORMATION: Xaa is any amino acid and contiguous amino acid
      residues alternate between D and L residues
<220> FEATURE:
<221> NAME/KEY: MISC_FEATURE
<222> LOCATION: (13)..(16)
<223> OTHER INFORMATION: Xaa is any amino acid or is optionally absent
      and contiguous amino acid residues alternate between D and L
      residues
<220> FEATURE:
<221> NAME/KEY: MISC_FEATURE
<222> LOCATION: (17)..(21)
<223> OTHER INFORMATION: Xaa is any amino acid or is optionally absent
      and contiguous amino acid residues do not alternate between L and
```

```
                D residues
<220> FEATURE:
<221> NAME/KEY: MISC_FEATURE
<222> LOCATION: (22)..(25)
<223> OTHER INFORMATION: Xaa is any amino acid and contiguous amino acid
      residues alternate between D amino acids and L amino acids
<220> FEATURE:
<221> NAME/KEY: MISC_FEATURE
<222> LOCATION: (26)..(33)
<223> OTHER INFORMATION: Xaa is any amino acid or is optinally absent
      and contiguous amino acid residues alternate between D amino acids
      and L amino acids
<220> FEATURE:
<221> NAME/KEY: MISC_FEATURE
<222> LOCATION: (34)..(37)
<223> OTHER INFORMATION: Xaa is any amino acid or is optionally absent
      and contiguous amino acid residues do not alternate between L and
      D residues

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa
        35

<210> SEQ ID NO 2
<211> LENGTH: 23
<212> TYPE: PRT
<213> ORGANISM: Artificial Sequence
<220> FEATURE:
<223> OTHER INFORMATION: Synthetic

<400> SEQUENCE: 2

Arg Gly Glu Met Asn Leu Ser Trp Met Asn Glu Tyr Ser Gly Trp Thr
1               5                   10                  15

Met Asn Leu Lys Met Gly Arg
            20

<210> SEQ ID NO 3
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is any amino acid

<400> SEQUENCE: 3

Gly Gly Xaa Gly Gly
1               5

<210> SEQ ID NO 4
<211> LENGTH: 21
<212> TYPE: PRT
<213> ORGANISM: Artificial Sequence
<220> FEATURE:
<223> OTHER INFORMATION: Synthetic

<400> SEQUENCE: 4

Glu Leu Lys Ser Trp Thr Asn Ala Ala Ala Ala Trp Thr Met Gln Leu
1               5                   10                  15

Leu Asp Pro Asn Arg
            20
```

```
<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

Glu Leu Lys Ser Trp Thr
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic

<400> SEQUENCE: 6

Ala Ala Trp Thr Met Gln Leu Leu Asp Pro Asn
1               5                   10

<210> SEQ ID NO 7
<211> LENGTH: 23
<212> TYPE: PRT
<213> ORGANISM: Artificial Sequence
<220> FEATURE:
<223> OTHER INFORMATION: Synthetic

<400> SEQUENCE: 7

Arg Gly Glu Met Asn Leu Ser Trp Met Asn Glu Tyr Ser Asn Trp Thr
1               5                   10                  15

Met Asn Leu Lys Met Gly Arg
            20

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

Glu Met Asn Leu Ser Trp Met
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Asn Glu Tyr Ser Asn
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Trp Thr Met Asn Leu Lys Met
```

```
1               5
```

<210> SEQ ID NO 11
<211> LENGTH: 19
<212> TYPE: PRT
<213> ORGANISM: Artificial Sequence
<220> FEATURE:
<223> OTHER INFORMATION: Synthetic

<400> SEQUENCE: 11

```
Glu Gln Gln Leu Ser Trp Thr Asn Ala Ala Ala Ala Trp Thr Gln Gln
1               5                   10                  15

Leu Lys Gln
```

<210> SEQ ID NO 12
<211> LENGTH: 19
<212> TYPE: PRT
<213> ORGANISM: Artificial Sequence
<220> FEATURE:
<223> OTHER INFORMATION: Synthetic

<400> SEQUENCE: 12

```
Glu Gln Gln Leu Ser Trp Lys Asn Ala Ala Ala Ala Trp Thr Gln Gln
1               5                   10                  15

Leu Lys Gln
```

<210> SEQ ID NO 13
<211> LENGTH: 19
<212> TYPE: PRT
<213> ORGANISM: Artificial Sequence
<220> FEATURE:
<223> OTHER INFORMATION: Synthetic

<400> SEQUENCE: 13

```
Glu Gln Gln Leu Ser Trp Thr Asn Ala Ala Ala Ala Trp Thr Lys Gln
1               5                   10                  15

Leu Lys Gln
```

<210> SEQ ID NO 14
<211> LENGTH: 19
<212> TYPE: PRT
<213> ORGANISM: Artificial Sequence
<220> FEATURE:
<223> OTHER INFORMATION: Synthetic

<400> SEQUENCE: 14

```
Glu Gln Gln Leu Ser Trp Thr Asn Ala Ala Ala Ala Trp Thr Gln Gln
1               5                   10                  15

Leu Lys Lys
```

<210> SEQ ID NO 15
<211> LENGTH: 19
<212> TYPE: PRT
<213> ORGANISM: Artificial Sequence
<220> FEATURE:
<223> OTHER INFORMATION: Synthetic

<400> SEQUENCE: 15

```
Glu Gln Gln Leu Ser Trp Lys Asn Ala Ala Ala Ala Trp Thr Gln Gln
1               5                   10                  15

Leu Lys Lys
```

<210> SEQ ID NO 16

```
<211> LENGTH: 19
<212> TYPE: PRT
<213> ORGANISM: Artificial Sequence
<220> FEATURE:
<223> OTHER INFORMATION: Synthetic

<400> SEQUENCE: 16

Glu Gln Gln Leu Ser Trp Thr Asn Ala Ala Ala Ala Trp Thr Lys Gln
1               5                   10                  15

Leu Lys Lys

<210> SEQ ID NO 17
<211> LENGTH: 19
<212> TYPE: PRT
<213> ORGANISM: Artificial Sequence
<220> FEATURE:
<223> OTHER INFORMATION: Synthetic

<400> SEQUENCE: 17

Glu Gln Gln Leu Ser Trp Lys Asn Ala Ala Ala Ala Trp Thr Lys Gln
1               5                   10                  15

Leu Lys Gln

<210> SEQ ID NO 18
<211> LENGTH: 19
<212> TYPE: PRT
<213> ORGANISM: Artificial Sequence
<220> FEATURE:
<223> OTHER INFORMATION: Synthetic

<400> SEQUENCE: 18

Glu Gln Gln Leu Ser Trp Thr Asn Pro Ala Ala Ala Trp Thr Gln Gln
1               5                   10                  15

Leu Lys Gln

<210> SEQ ID NO 19
<211> LENGTH: 19
<212> TYPE: PRT
<213> ORGANISM: Artificial Sequence
<220> FEATURE:
<223> OTHER INFORMATION: Synthetic

<400> SEQUENCE: 19

Glu Gln Gln Leu Ser Trp Thr Asn Ala Pro Ala Ala Trp Thr Gln Gln
1               5                   10                  15

Leu Lys Gln

<210> SEQ ID NO 20
<211> LENGTH: 19
<212> TYPE: PRT
<213> ORGANISM: Artificial Sequence
<220> FEATURE:
<223> OTHER INFORMATION: Synthetic

<400> SEQUENCE: 20

Glu Gln Gln Leu Glu Trp Thr Asn Ala Ala Ala Ala Trp Lys Gln Gln
1               5                   10                  15

Leu Lys Gln

<210> SEQ ID NO 21
<211> LENGTH: 19
<212> TYPE: PRT
<213> ORGANISM: Artificial Sequence
<220> FEATURE:
```

<223> OTHER INFORMATION: Synthetic

<400> SEQUENCE: 21

Glu Gln Gln Leu Glu Trp Thr Asn Ala Ala Ala Ala Trp Lys Gln Gln
1               5                   10                  15

Leu Lys Gln

<210> SEQ ID NO 22
<211> LENGTH: 19
<212> TYPE: PRT
<213> ORGANISM: Artificial Sequence
<220> FEATURE:
<223> OTHER INFORMATION: Synthetic

<400> SEQUENCE: 22

Glu Gln Gln Leu Ser Leu Thr Asn Ala Ala Ala Ala Leu Thr Gln Gln
1               5                   10                  15

Leu Lys Gln

<210> SEQ ID NO 23
<211> LENGTH: 19
<212> TYPE: PRT
<213> ORGANISM: Artificial Sequence
<220> FEATURE:
<223> OTHER INFORMATION: Synthetic

<400> SEQUENCE: 23

Glu Gln Gln Leu Ser Ile Thr Asn Ala Ala Ala Ala Ile Thr Gln Gln
1               5                   10                  15

Leu Lys Gln

<210> SEQ ID NO 24
<211> LENGTH: 19
<212> TYPE: PRT
<213> ORGANISM: Artificial Sequence
<220> FEATURE:
<223> OTHER INFORMATION: Synthetic

<400> SEQUENCE: 24

Glu Gln Gln Ile Ser Ile Thr Asn Ala Ala Ala Ala Ile Thr Gln Gln
1               5                   10                  15

Leu Lys Gln

<210> SEQ ID NO 25
<211> LENGTH: 19
<212> TYPE: PRT
<213> ORGANISM: Artificial Sequence
<220> FEATURE:
<223> OTHER INFORMATION: Synthetic

<400> SEQUENCE: 25

Asn Met Asn Leu Ser Leu Met Asn Glu Tyr Ser Ala Leu Thr Met Asn
1               5                   10                  15

Leu Gln Met

<210> SEQ ID NO 26
<211> LENGTH: 19
<212> TYPE: PRT
<213> ORGANISM: Artificial Sequence
<220> FEATURE:
<223> OTHER INFORMATION: Synthetic

<400> SEQUENCE: 26

Asn Met Asn Leu Ser Leu Met Asn Ala Ala Ala Leu Thr Met Asn
1               5                   10                  15

Leu Gln Met

<210> SEQ ID NO 27
<211> LENGTH: 19
<212> TYPE: PRT
<213> ORGANISM: Artificial Sequence
<220> FEATURE:
<223> OTHER INFORMATION: Synthetic

<400> SEQUENCE: 27

Asn Met Asn Leu Ser Leu Met Asn Ala Ala Ser Ala Leu Thr Met Asn
1               5                   10                  15

Leu Gln Met

<210> SEQ ID NO 28
<211> LENGTH: 19
<212> TYPE: PRT
<213> ORGANISM: Artificial Sequence
<220> FEATURE:
<223> OTHER INFORMATION: Synthetic

<400> SEQUENCE: 28

Gln Gln Gln Gln Gln Gln Gln Asn Ala Ala Ala Ala Gln Gln Gln Gln
1               5                   10                  15

Gln Gln Gln

<210> SEQ ID NO 29
<211> LENGTH: 21
<212> TYPE: PRT
<213> ORGANISM: Artificial Sequence
<220> FEATURE:
<223> OTHER INFORMATION: Synthetic

<400> SEQUENCE: 29

Lys Glu Gln Gln Leu Ser Trp Thr Asn Ala Ala Ala Ala Trp Thr Gln
1               5                   10                  15

Gln Leu Lys Gln Gln
            20

<210> SEQ ID NO 30
<211> LENGTH: 21
<212> TYPE: PRT
<213> ORGANISM: Artificial Sequence
<220> FEATURE:
<223> OTHER INFORMATION: Synthetic

<400> SEQUENCE: 30

Lys Glu Gln Gln Leu Ser Trp Thr Asn Pro Ala Ala Ala Trp Thr Gln
1               5                   10                  15

Gln Leu Lys Gln Gln
            20

<210> SEQ ID NO 31
<211> LENGTH: 21
<212> TYPE: PRT
<213> ORGANISM: Artificial Sequence
<220> FEATURE:
<223> OTHER INFORMATION: Synthetic

<400> SEQUENCE: 31

Lys Glu Gln Gln Leu Ser Trp Thr Asn Ala Pro Ala Ala Trp Thr Gln
1               5                   10                  15

```
Gln Leu Lys Gln Gln
         20

<210> SEQ ID NO 32
<211> LENGTH: 21
<212> TYPE: PRT
<213> ORGANISM: Artificial Sequence
<220> FEATURE:
<223> OTHER INFORMATION: Synthetic

<400> SEQUENCE: 32

Lys Glu Gln Gln Leu Glu Trp Thr Asn Ala Ala Ala Ala Trp Lys Gln
1               5                   10                  15

Gln Leu Lys Gln Gln
         20

<210> SEQ ID NO 33
<211> LENGTH: 21
<212> TYPE: PRT
<213> ORGANISM: Artificial Sequence
<220> FEATURE:
<223> OTHER INFORMATION: Synthetic

<400> SEQUENCE: 33

Lys Glu Gln Gln Leu Ser Trp Thr Asn Ala Pro Ala Ala Trp Thr Gln
1               5                   10                  15

Gln Leu Arg Gln Gln
         20

<210> SEQ ID NO 34
<211> LENGTH: 21
<212> TYPE: PRT
<213> ORGANISM: Artificial Sequence
<220> FEATURE:
<223> OTHER INFORMATION: Synthetic

<400> SEQUENCE: 34

Lys Glu Gln Gln Leu Glu Trp Thr Asn Ala Pro Ala Ala Trp Lys Gln
1               5                   10                  15

Gln Leu Lys Gln Gln
         20

<210> SEQ ID NO 35
<211> LENGTH: 23
<212> TYPE: PRT
<213> ORGANISM: Artificial Sequence
<220> FEATURE:
<223> OTHER INFORMATION: Synthetic

<400> SEQUENCE: 35

Arg Gly Glu Gln Gln Leu Ser Trp Thr Asn Ala Ala Ala Ala Trp Thr
1               5                   10                  15

Gln Gln Leu Lys Gln Gly Arg
         20

<210> SEQ ID NO 36
<211> LENGTH: 23
<212> TYPE: PRT
<213> ORGANISM: Artificial Sequence
<220> FEATURE:
<223> OTHER INFORMATION: Synthetic

<400> SEQUENCE: 36

Arg Gly Glu Met Asn Leu Ser Trp Met Asn Ala Ala Ala Ala Trp Thr
```

```
                1               5                   10                  15
Met Asn Leu Lys Met Gly Arg
                20

<210> SEQ ID NO 37
<211> LENGTH: 23
<212> TYPE: PRT
<213> ORGANISM: Artificial Sequence
<220> FEATURE:
<223> OTHER INFORMATION: Synthetic

<400> SEQUENCE: 37

Arg Gly Glu Gln Gln Leu Ser Trp Thr Asn Ala Ala Ala Ala Trp Thr
1               5                   10                  15
Met Gln Leu Lys Gln Gly Arg
                20

<210> SEQ ID NO 38
<211> LENGTH: 23
<212> TYPE: PRT
<213> ORGANISM: Artificial Sequence
<220> FEATURE:
<223> OTHER INFORMATION: Synthetic

<400> SEQUENCE: 38

Arg Gly Glu Met Asn Leu Ser Trp Met Asn Glu Tyr Ser Gly Trp Thr
1               5                   10                  15
Met Asn Leu Lys Met Gly Arg
                20

<210> SEQ ID NO 39
<211> LENGTH: 23
<212> TYPE: PRT
<213> ORGANISM: Artificial Sequence
<220> FEATURE:
<223> OTHER INFORMATION: Synthetic

<400> SEQUENCE: 39

Arg Gly Glu Met Asn Leu Ser Trp Met Asn Glu Tyr Ser Asn Trp Thr
1               5                   10                  15
Met Asn Leu Lys Met Gly Arg
                20

<210> SEQ ID NO 40
<211> LENGTH: 19
<212> TYPE: PRT
<213> ORGANISM: Artificial Sequence
<220> FEATURE:
<223> OTHER INFORMATION: Synthetic

<400> SEQUENCE: 40

Asn Met Asn Leu Ser Leu Met Ala Glu Tyr Ser Gly Leu Thr Met Asn
1               5                   10                  15
Leu Gln Met

<210> SEQ ID NO 41
<211> LENGTH: 19
<212> TYPE: PRT
<213> ORGANISM: Artificial Sequence
<220> FEATURE:
<223> OTHER INFORMATION: Synthetic

<400> SEQUENCE: 41

Asn Met Asn Leu Ser Leu Met Asn Glu Thr Ser Gly Leu Thr Met Asn
```

```
1               5                  10                 15

Leu Gln Met

<210> SEQ ID NO 42
<211> LENGTH: 12
<212> TYPE: PRT
<213> ORGANISM: Artificial Sequence
<220> FEATURE:
<223> OTHER INFORMATION: Synthetic

<400> SEQUENCE: 42

Gln Leu Ser Trp Glu Pro Asn Lys Trp Thr Gln Lys
1               5                  10

<210> SEQ ID NO 43
<211> LENGTH: 12
<212> TYPE: PRT
<213> ORGANISM: Artificial Sequence
<220> FEATURE:
<223> OTHER INFORMATION: Synthetic

<400> SEQUENCE: 43

Gln Gln Ser Trp Glu Pro Asn Lys Trp Thr Leu Lys
1               5                  10

<210> SEQ ID NO 44
<211> LENGTH: 12
<212> TYPE: PRT
<213> ORGANISM: Artificial Sequence
<220> FEATURE:
<223> OTHER INFORMATION: Synthetic

<400> SEQUENCE: 44

Ser Met Thr Leu Glu Pro Asn Lys Leu Thr Leu Lys
1               5                  10

<210> SEQ ID NO 45
<211> LENGTH: 19
<212> TYPE: PRT
<213> ORGANISM: Artificial Sequence
<220> FEATURE:
<223> OTHER INFORMATION: Synthetic

<400> SEQUENCE: 45

Asn Met Asn Leu Ser Leu Met Asn Glu Tyr Ser Asn Leu Thr Met Asn
1               5                  10                 15

Leu Gln Met

<210> SEQ ID NO 46
<211> LENGTH: 19
<212> TYPE: PRT
<213> ORGANISM: Artificial Sequence
<220> FEATURE:
<223> OTHER INFORMATION: Synthetic

<400> SEQUENCE: 46

Asn Met Asn Leu Ser Leu Met Asn Glu Tyr Ser Asp Leu Thr Met Asn
1               5                  10                 15

Leu Gln Met

<210> SEQ ID NO 47
<211> LENGTH: 19
<212> TYPE: PRT
<213> ORGANISM: Artificial Sequence
<220> FEATURE:
```

-continued

<223> OTHER INFORMATION: Synthetic

<400> SEQUENCE: 47

Asn Met Asn Leu Ser Leu Met Asn Glu Tyr Ser Gly Leu Thr Met Asn
1               5                   10                  15

Leu Gln Met

<210> SEQ ID NO 48
<211> LENGTH: 19
<212> TYPE: PRT
<213> ORGANISM: Artificial Sequence
<220> FEATURE:
<223> OTHER INFORMATION: Synthetic

<400> SEQUENCE: 48

Asn Met Asn Leu Ser Leu Met Leu Glu Tyr Ser Gly Leu Thr Met Asn
1               5                   10                  15

Leu Gln Met

<210> SEQ ID NO 49
<211> LENGTH: 19
<212> TYPE: PRT
<213> ORGANISM: Artificial Sequence
<220> FEATURE:
<223> OTHER INFORMATION: Synthetic

<400> SEQUENCE: 49

Glu Met Asn Leu Ser Leu Met Asn Glu Tyr Ser Gly Leu Thr Met Asn
1               5                   10                  15

Leu Lys Met

<210> SEQ ID NO 50
<211> LENGTH: 19
<212> TYPE: PRT
<213> ORGANISM: Artificial Sequence
<220> FEATURE:
<223> OTHER INFORMATION: Synthetic

<400> SEQUENCE: 50

Asn Met Asn Leu Ser Phe Met Asn Glu Tyr Ser Gly Phe Thr Met Asn
1               5                   10                  15

Leu Gln Met

<210> SEQ ID NO 51
<211> LENGTH: 19
<212> TYPE: PRT
<213> ORGANISM: Artificial Sequence
<220> FEATURE:
<223> OTHER INFORMATION: Synthetic

<400> SEQUENCE: 51

Asn Met Asn Leu Ser Trp Met Asn Glu Tyr Ser Gly Trp Thr Met Asn
1               5                   10                  15

Leu Gln Met

<210> SEQ ID NO 52
<211> LENGTH: 19
<212> TYPE: PRT
<213> ORGANISM: Artificial Sequence
<220> FEATURE:
<223> OTHER INFORMATION: Synthetic

<400> SEQUENCE: 52

```
Met Asn Leu Asn Leu Ser Phe Asn Glu Tyr Ser Gly Met Phe Thr Leu
1               5                   10                  15

Asn Met Gln
```

<210> SEQ ID NO 53
<211> LENGTH: 19
<212> TYPE: PRT
<213> ORGANISM: Artificial Sequence
<220> FEATURE:
<223> OTHER INFORMATION: Synthetic

<400> SEQUENCE: 53

```
Asn Met Asn Leu Ser Leu Met Gly Glu Tyr Ser Gly Leu Thr Met Asn
1               5                   10                  15

Leu Gln Met
```

<210> SEQ ID NO 54
<211> LENGTH: 19
<212> TYPE: PRT
<213> ORGANISM: Artificial Sequence
<220> FEATURE:
<223> OTHER INFORMATION: Synthetic

<400> SEQUENCE: 54

```
Asn Met Asn Leu Ser Leu Met Gly Glu Tyr Ser Asn Leu Thr Met Asn
1               5                   10                  15

Leu Gln Met
```

<210> SEQ ID NO 55
<211> LENGTH: 19
<212> TYPE: PRT
<213> ORGANISM: Artificial Sequence
<220> FEATURE:
<223> OTHER INFORMATION: Synthetic

<400> SEQUENCE: 55

```
Asn Met Asn Leu Ser Leu Met Asn Glu Ala Ser Gly Leu Thr Met Asn
1               5                   10                  15

Leu Gln Met
```

<210> SEQ ID NO 56
<211> LENGTH: 19
<212> TYPE: PRT
<213> ORGANISM: Artificial Sequence
<220> FEATURE:
<223> OTHER INFORMATION: Synthetic

<400> SEQUENCE: 56

```
Asn Trp Asn Leu Ser Trp Met Asn Glu Tyr Ser Gly Trp Thr Met Asn
1               5                   10                  15

Trp Gln Met
```

<210> SEQ ID NO 57
<211> LENGTH: 19
<212> TYPE: PRT
<213> ORGANISM: Artificial Sequence
<220> FEATURE:
<223> OTHER INFORMATION: Synthetic

<400> SEQUENCE: 57

```
Glu Met Asn Leu Ser Trp Met Asn Glu Tyr Ser Gly Trp Thr Met Asn
1               5                   10                  15

Leu Lys Met
```

<210> SEQ ID NO 58
<211> LENGTH: 19
<212> TYPE: PRT
<213> ORGANISM: Artificial Sequence
<220> FEATURE:
<223> OTHER INFORMATION: Synthetic

<400> SEQUENCE: 58

Asn Thr Asn Leu Ser Leu Met Asn Glu Thr Ser Gly Leu Thr Met Asn
1               5                   10                  15

Thr Gln Lys

<210> SEQ ID NO 59
<211> LENGTH: 19
<212> TYPE: PRT
<213> ORGANISM: Artificial Sequence
<220> FEATURE:
<223> OTHER INFORMATION: Synthetic

<400> SEQUENCE: 59

Asn Met Asn Leu Ser Leu Met Asn Lys Thr Ser Gly Leu Thr Met Asn
1               5                   10                  15

Leu Gln Met

<210> SEQ ID NO 60
<211> LENGTH: 19
<212> TYPE: PRT
<213> ORGANISM: Artificial Sequence
<220> FEATURE:
<223> OTHER INFORMATION: Synthetic

<400> SEQUENCE: 60

Asn Thr Asn Leu Ser Trp Met Asn Glu Thr Ser Gly Trp Thr Met Asn
1               5                   10                  15

Thr Gln Lys

<210> SEQ ID NO 61
<211> LENGTH: 19
<212> TYPE: PRT
<213> ORGANISM: Artificial Sequence
<220> FEATURE:
<223> OTHER INFORMATION: Synthetic

<400> SEQUENCE: 61

Asn Thr Asn Leu Ser Leu Met Asn Glu Tyr Ser Gly Leu Thr Met Asn
1               5                   10                  15

Thr Gln Lys

<210> SEQ ID NO 62
<211> LENGTH: 19
<212> TYPE: PRT
<213> ORGANISM: Artificial Sequence
<220> FEATURE:
<223> OTHER INFORMATION: Synthetic

<400> SEQUENCE: 62

Asn Thr Asn Leu Ser Trp Met Asn Glu Tyr Ser Gly Trp Thr Met Asn
1               5                   10                  15

Thr Gln Lys

<210> SEQ ID NO 63
<211> LENGTH: 19

```
<212> TYPE: PRT
<213> ORGANISM: Artificial Sequence
<220> FEATURE:
<223> OTHER INFORMATION: Synthetic

<400> SEQUENCE: 63

Asn Met Asn Leu Ser Leu Met Asn Ala Ala Thr Gly Leu Thr Met Asn
1               5                   10                  15

Leu Gln Met

<210> SEQ ID NO 64
<211> LENGTH: 19
<212> TYPE: PRT
<213> ORGANISM: Artificial Sequence
<220> FEATURE:
<223> OTHER INFORMATION: Synthetic

<400> SEQUENCE: 64

Asn Met Asn Leu Ser Leu Met Asn Ala Ala Thr Gly Leu Thr Met Asn
1               5                   10                  15

Leu Gln Met

<210> SEQ ID NO 65
<211> LENGTH: 19
<212> TYPE: PRT
<213> ORGANISM: Artificial Sequence
<220> FEATURE:
<223> OTHER INFORMATION: Synthetic

<400> SEQUENCE: 65

Asn Met Asn Leu Ser Leu Met Gly Asp Tyr Ser Asn Leu Thr Met Asn
1               5                   10                  15

Leu Gln Met

<210> SEQ ID NO 66
<211> LENGTH: 19
<212> TYPE: PRT
<213> ORGANISM: Artificial Sequence
<220> FEATURE:
<223> OTHER INFORMATION: Synthetic

<400> SEQUENCE: 66

Asn Met Asn Leu Ser Leu Met Gly Ala Ala Ser Asn Leu Thr Met Asn
1               5                   10                  15

Leu Gln Met

<210> SEQ ID NO 67
<211> LENGTH: 19
<212> TYPE: PRT
<213> ORGANISM: Artificial Sequence
<220> FEATURE:
<223> OTHER INFORMATION: Synthetic

<400> SEQUENCE: 67

Gln Met Gln Leu Ser Leu Met Asn Glu Tyr Ser Gly Leu Thr Met Gln
1               5                   10                  15

Leu Gln Met

<210> SEQ ID NO 68
<211> LENGTH: 19
<212> TYPE: PRT
<213> ORGANISM: Artificial Sequence
<220> FEATURE:
<223> OTHER INFORMATION: Synthetic
```

<400> SEQUENCE: 68

Gln Met Gln Leu Ser Leu Gln Asn Glu Tyr Ser Gly Leu Thr Met Gln
1               5                   10                  15

Leu Gln Gln

<210> SEQ ID NO 69
<211> LENGTH: 23
<212> TYPE: PRT
<213> ORGANISM: Artificial Sequence
<220> FEATURE:
<223> OTHER INFORMATION: Synthetic

<400> SEQUENCE: 69

Arg Gly Asn Met Asn Leu Ser Trp Met Asn Glu Tyr Ser Gly Trp Thr
1               5                   10                  15

Met Asn Leu Gln Met Gly Arg
            20

<210> SEQ ID NO 70
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION-optional

<400> SEQUENCE: 70

Arg Gly Glu Met Asn Leu Ser Trp Met Asn Glu Tyr Ser Gly Trp Thr
1               5                   10                  15

Met Asn Leu Lys Met Gly Arg
            20

<210> SEQ ID NO 71
<211> LENGTH: 23
<212> TYPE: PRT
<213> ORGANISM: Artificial Sequence
<220> FEATURE:
<223> OTHER INFORMATION: Synthetic

<400> SEQUENCE: 71

Arg Gly Glu Met Asn Leu Ser Trp Met Asn Glu Tyr Tyr Gly Trp Thr
1               5                   10                  15

Met Asn Leu Lys Met Gly Arg
            20

<210> SEQ ID NO 72
<211> LENGTH: 23
<212> TYPE: PRT
<213> ORGANISM: Artificial Sequence
<220> FEATURE:
<223> OTHER INFORMATION: Synthetic

<400> SEQUENCE: 72

Arg Gly Glu Met Ala Leu Ser Trp Met Asn Glu Tyr Ser Gly Trp Thr
1               5                   10                  15

Met Asn Leu Lys Met Gly Arg
            20

<210> SEQ ID NO 73
<211> LENGTH: 23

```
<212> TYPE: PRT
<213> ORGANISM: Artificial Sequence
<220> FEATURE:
<223> OTHER INFORMATION: Synthetic

<400> SEQUENCE: 73

Arg Gly Glu Met Asn Leu Ser Trp Met Asn Glu Tyr Tyr Gly Trp Thr
1               5                   10                  15
Cys Asn Leu Lys Met Gly Arg
            20

<210> SEQ ID NO 74
<211> LENGTH: 23
<212> TYPE: PRT
<213> ORGANISM: Artificial Sequence
<220> FEATURE:
<223> OTHER INFORMATION: Synthetic

<400> SEQUENCE: 74

Arg Gly Glu Met Asn Leu Ser Trp Met Asn Glu Tyr Tyr Gly Trp Thr
1               5                   10                  15
Met Asn Cys Lys Met Gly Arg
            20

<210> SEQ ID NO 75
<211> LENGTH: 23
<212> TYPE: PRT
<213> ORGANISM: Artificial Sequence
<220> FEATURE:
<223> OTHER INFORMATION: Synthetic

<400> SEQUENCE: 75

Arg Gly Glu Met Asn Leu Ser Trp Met Asn Glu Tyr Tyr Gly Trp Thr
1               5                   10                  15
Met Asn Leu Lys Cys Gly Arg
            20

<210> SEQ ID NO 76
<211> LENGTH: 23
<212> TYPE: PRT
<213> ORGANISM: Artificial Sequence
<220> FEATURE:
<223> OTHER INFORMATION: Synthetic

<400> SEQUENCE: 76

Arg Gly Glu Met Asn Leu Ser Trp Met Asn Glu Tyr Tyr Gly Trp Thr
1               5                   10                  15
Met Asn Leu Lys Met Cys Arg
            20

<210> SEQ ID NO 77
<211> LENGTH: 23
<212> TYPE: PRT
<213> ORGANISM: Artificial Sequence
<220> FEATURE:
<223> OTHER INFORMATION: Synthetic

<400> SEQUENCE: 77

Arg Gly Glu Met Asn Leu Ser Trp Met Asn Glu Tyr Tyr Gly Trp Cys
1               5                   10                  15
Met Asn Leu Lys Met Gly Arg
            20

<210> SEQ ID NO 78
```

```
<211> LENGTH: 23
<212> TYPE: PRT
<213> ORGANISM: Artificial Sequence
<220> FEATURE:
<223> OTHER INFORMATION: Synthetic

<400> SEQUENCE: 78

Arg Gly Glu Met Asn Leu Ser Trp Met Asn Glu Tyr Tyr Gly Trp Thr
1               5                   10                  15

Met Cys Leu Lys Met Gly Arg
            20

<210> SEQ ID NO 79
<211> LENGTH: 23
<212> TYPE: PRT
<213> ORGANISM: Artificial Sequence
<220> FEATURE:
<223> OTHER INFORMATION: Synthetic

<400> SEQUENCE: 79

Arg Gly Glu Met Asn Leu Ser Trp Met Asn Glu Tyr Tyr Gly Trp Thr
1               5                   10                  15

Met Asn Leu Cys Met Gly Arg
            20

<210> SEQ ID NO 80
<211> LENGTH: 23
<212> TYPE: PRT
<213> ORGANISM: Artificial Sequence
<220> FEATURE:
<223> OTHER INFORMATION: Synthetic

<400> SEQUENCE: 80

Arg Gly Glu Met Asn Leu Phe Trp Met Asn Glu Tyr Tyr Gly Trp Thr
1               5                   10                  15

Met Asn Leu Lys Met Gly Arg
            20

<210> SEQ ID NO 81
<211> LENGTH: 23
<212> TYPE: PRT
<213> ORGANISM: Artificial Sequence
<220> FEATURE:
<223> OTHER INFORMATION: Synthetic

<400> SEQUENCE: 81

Arg Gly Glu Met Asn Leu Ser Trp Met Asn Glu Tyr Tyr Gly Trp Thr
1               5                   10                  15

Lys Asn Leu Lys Met Gly Arg
            20

<210> SEQ ID NO 82
<211> LENGTH: 23
<212> TYPE: PRT
<213> ORGANISM: Artificial Sequence
<220> FEATURE:
<223> OTHER INFORMATION: Synthetic

<400> SEQUENCE: 82

Arg Gly Glu Met Asn Leu Ser Trp Met Asn Glu Tyr Tyr Gly Trp Thr
1               5                   10                  15

Met Asn Lys Lys Met Gly Arg
            20
```

```
<210> SEQ ID NO 83
<211> LENGTH: 23
<212> TYPE: PRT
<213> ORGANISM: Artificial Sequence
<220> FEATURE:
<223> OTHER INFORMATION: Synthetic

<400> SEQUENCE: 83

Arg Gly Glu Met Asn Leu Phe Trp Met Asn Glu Tyr Tyr Gly Trp Thr
1               5                   10                  15

Met Asn Cys Lys Met Gly Arg
            20

<210> SEQ ID NO 84
<211> LENGTH: 23
<212> TYPE: PRT
<213> ORGANISM: Artificial Sequence
<220> FEATURE:
<223> OTHER INFORMATION: Synthetic

<400> SEQUENCE: 84

Arg Gly Glu Met Asn Leu Phe Trp Met Asn Glu Tyr Tyr Gly Trp Thr
1               5                   10                  15

Arg Asn Cys Lys Met Gly Arg
            20

<210> SEQ ID NO 85
<211> LENGTH: 23
<212> TYPE: PRT
<213> ORGANISM: Artificial Sequence
<220> FEATURE:
<223> OTHER INFORMATION: Synthetic

<400> SEQUENCE: 85

Arg Gly Glu Met Asn Leu Phe Trp Met Asn Glu Tyr Tyr Gly Trp Thr
1               5                   10                  15

Lys Asn Cys Lys Met Gly Arg
            20

<210> SEQ ID NO 86
<211> LENGTH: 23
<212> TYPE: PRT
<213> ORGANISM: Artificial Sequence
<220> FEATURE:
<223> OTHER INFORMATION: Synthetic

<400> SEQUENCE: 86

Arg Gly Glu Met Asn Leu Phe Trp Met Leu Glu Tyr Tyr Gly Trp Thr
1               5                   10                  15

Met Asn Cys Lys Met Gly Arg
            20

<210> SEQ ID NO 87
<211> LENGTH: 23
<212> TYPE: PRT
<213> ORGANISM: Artificial Sequence
<220> FEATURE:
<223> OTHER INFORMATION: Synthetic

<400> SEQUENCE: 87

Arg Gly Glu Met Asn Leu Phe Trp Met His Glu Tyr Tyr Gly Trp Thr
1               5                   10                  15

Met Asn Cys Lys Met Gly Arg
            20
```

<210> SEQ ID NO 88
<211> LENGTH: 23
<212> TYPE: PRT
<213> ORGANISM: Artificial Sequence
<220> FEATURE:
<223> OTHER INFORMATION: Synthetic

<400> SEQUENCE: 88

Arg Gly Glu Met Asn Leu Phe Trp Met Met Glu Tyr Tyr Gly Trp Thr
1               5                   10                  15

Met Asn Cys Lys Met Gly Arg
            20

<210> SEQ ID NO 89
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 89

Ala Gln Gln Ile Glu Cys Ile Thr Asn Val Trp Asp Lys Glu Ile Thr
1               5                   10                  15

Met Tyr Phe Asn Val Ser Glu
            20

<210> SEQ ID NO 90
<211> LENGTH: 23
<212> TYPE: PRT
<213> ORGANISM: Artificial Sequence
<220> FEATURE:
<223> OTHER INFORMATION: Synthetic

<400> SEQUENCE: 90

Trp Arg Pro Trp Gly Ile Asp Gln Met Asn Thr Val Lys Gln Arg Lys
1               5                   10                  15

Ala Ser Val Tyr Leu Gln Pro
            20

<210> SEQ ID NO 91
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION-optional

<400> SEQUENCE: 91

Arg Gly Asn Trp Asn Glu Ser Lys Met Asn Glu Tyr Ser Gly Trp Met
1               5                   10                  15

Leu Met Leu Thr Met Gly Arg
            20

<210> SEQ ID NO 92
<211> LENGTH: 21
<212> TYPE: PRT
<213> ORGANISM: Artificial Sequence
<220> FEATURE:
<223> OTHER INFORMATION: Synthetic

<400> SEQUENCE: 92

Gln Gln Lys Ser Trp Thr Asn Ala Ala Ala Trp Thr Met Gln Leu
1               5                   10                  15

Lys Glu Pro Asn Lys
            20

<210> SEQ ID NO 93
<211> LENGTH: 21
<212> TYPE: PRT
<213> ORGANISM: Artificial Sequence
<220> FEATURE:
<223> OTHER INFORMATION: Synthetic

<400> SEQUENCE: 93

Gln Trp Lys Ser Trp Thr Asn Ala Ala Ala Trp Thr Met Gln Leu
1               5                   10                  15

Trp Asp Pro Asn Arg
            20

<210> SEQ ID NO 94
<211> LENGTH: 21
<212> TYPE: PRT
<213> ORGANISM: Artificial Sequence
<220> FEATURE:
<223> OTHER INFORMATION: Synthetic

<400> SEQUENCE: 94

Gln Gln Lys Ser Trp Thr Asn Ala Ala Ala Trp Thr Met Gln Leu
1               5                   10                  15

Lys Asp Pro Asn Arg
            20

<210> SEQ ID NO 95
<211> LENGTH: 21
<212> TYPE: PRT
<213> ORGANISM: Artificial Sequence
<220> FEATURE:
<223> OTHER INFORMATION: Synthetic

<400> SEQUENCE: 95

Leu Gln Lys Ser Trp Thr Asn Ala Ala Ala Trp Thr Met Gln Leu
1               5                   10                  15

Lys Asp Pro Asn Arg
            20

<210> SEQ ID NO 96
<211> LENGTH: 21
<212> TYPE: PRT
<213> ORGANISM: Artificial Sequence
<220> FEATURE:
<223> OTHER INFORMATION: Synthetic

<400> SEQUENCE: 96

Gln Leu Lys Ser Trp Thr Asn Ala Ala Ala Trp Thr Met Gln Leu
1               5                   10                  15

Leu Asp Pro Asn Arg
            20

<210> SEQ ID NO 97
<211> LENGTH: 21
<212> TYPE: PRT
<213> ORGANISM: Artificial Sequence
<220> FEATURE:

```
<223> OTHER INFORMATION: Synthetic

<400> SEQUENCE: 97

Trp Gln Lys Ser Trp Thr Asn Ala Ala Ala Trp Thr Met Gln Trp
1               5                   10                  15

Lys Asp Pro Asn Arg
            20

<210> SEQ ID NO 98
<211> LENGTH: 21
<212> TYPE: PRT
<213> ORGANISM: Artificial Sequence
<220> FEATURE:
<223> OTHER INFORMATION: Synthetic

<400> SEQUENCE: 98

Glu Trp Lys Ser Trp Thr Asn Ala Ala Ala Trp Thr Met Gln Leu
1               5                   10                  15

Trp Asp Pro Asn Arg
            20

<210> SEQ ID NO 99
<211> LENGTH: 21
<212> TYPE: PRT
<213> ORGANISM: Artificial Sequence
<220> FEATURE:
<223> OTHER INFORMATION: Synthetic

<400> SEQUENCE: 99

Glu Gln Lys Ser Trp Thr Asn Ala Ala Ala Trp Thr Met Gln Leu
1               5                   10                  15

Lys Asp Pro Asn Arg
            20

<210> SEQ ID NO 100
<211> LENGTH: 21
<212> TYPE: PRT
<213> ORGANISM: Artificial Sequence
<220> FEATURE:
<223> OTHER INFORMATION: Synthetic

<400> SEQUENCE: 100

Gln Gln Leu Ser Trp Thr Asn Ala Ala Ala Trp Thr Met Gln Leu
1               5                   10                  15

Lys Glu Pro Asn Lys
            20

<210> SEQ ID NO 101
<211> LENGTH: 17
<212> TYPE: PRT
<213> ORGANISM: Artificial Sequence
<220> FEATURE:
<223> OTHER INFORMATION: Synthetic

<400> SEQUENCE: 101

Gln Leu Ser Trp Thr Asn Ala Ala Ala Trp Thr Met Gln Leu Pro
1               5                   10                  15

Pro

<210> SEQ ID NO 102
<211> LENGTH: 21
<212> TYPE: PRT
<213> ORGANISM: Artificial Sequence
<220> FEATURE:
```

<223> OTHER INFORMATION: Synthetic

<400> SEQUENCE: 102

Glu Trp Lys Ser Trp Thr Asn Ala Ala Ala Trp Thr Glu Gln Leu
1               5                   10                  15

Trp Asp Pro Asn Arg
            20

<210> SEQ ID NO 103
<211> LENGTH: 21
<212> TYPE: PRT
<213> ORGANISM: Artificial Sequence
<220> FEATURE:
<223> OTHER INFORMATION: Synthetic

<400> SEQUENCE: 103

Gln Gln Lys Ser Trp Thr Asn Glu Tyr Ser Ala Trp Thr Met Gln Leu
1               5                   10                  15

Lys Glu Pro Asn Lys
            20

<210> SEQ ID NO 104
<211> LENGTH: 21
<212> TYPE: PRT
<213> ORGANISM: Artificial Sequence
<220> FEATURE:
<223> OTHER INFORMATION: Synthetic

<400> SEQUENCE: 104

Gln Gln Lys Ser Trp Thr Asn Glu Tyr Tyr Ala Trp Thr Met Gln Leu
1               5                   10                  15

Lys Glu Pro Asn Lys
            20

<210> SEQ ID NO 105
<211> LENGTH: 21
<212> TYPE: PRT
<213> ORGANISM: Artificial Sequence
<220> FEATURE:
<223> OTHER INFORMATION: Synthetic

<400> SEQUENCE: 105

Gln Gln Lys Phe Trp Thr Asn Glu Tyr Tyr Ala Trp Thr Met Gln Leu
1               5                   10                  15

Lys Glu Pro Asn Lys
            20

<210> SEQ ID NO 106
<211> LENGTH: 21
<212> TYPE: PRT
<213> ORGANISM: Artificial Sequence
<220> FEATURE:
<223> OTHER INFORMATION: Synthetic

<400> SEQUENCE: 106

Gln Gln Lys Ser Trp Thr Asn Glu Tyr Tyr Ala Trp Thr Met Gln Cys
1               5                   10                  15

Lys Glu Pro Asn Lys
            20

<210> SEQ ID NO 107
<211> LENGTH: 21
<212> TYPE: PRT
<213> ORGANISM: Artificial Sequence
<220> FEATURE:
<223> OTHER INFORMATION: Synthetic

<400> SEQUENCE: 107

Gln Gln Lys Ser Trp Thr Asn Glu Tyr Tyr Ala Trp Thr Cys Gln Leu
1               5                   10                  15

Lys Glu Pro Asn Lys
            20

<210> SEQ ID NO 108
<211> LENGTH: 21
<212> TYPE: PRT
<213> ORGANISM: Artificial Sequence
<220> FEATURE:
<223> OTHER INFORMATION: Synthetic

<400> SEQUENCE: 108

Gln Gln Lys Phe Trp Thr Asn Ala Ala Ala Ala Trp Thr Met Gln Leu
1               5                   10                  15

Lys Glu Pro Asn Lys
            20

<210> SEQ ID NO 109
<211> LENGTH: 21
<212> TYPE: PRT
<213> ORGANISM: Artificial Sequence
<220> FEATURE:
<223> OTHER INFORMATION: Synthetic

<400> SEQUENCE: 109

Gln Gln Lys Phe Trp Thr Asn Ala Ala Ala Ala Trp Thr Glu Gln Leu
1               5                   10                  15

Lys Glu Pro Asn Lys
            20

<210> SEQ ID NO 110
<211> LENGTH: 14
<212> TYPE: PRT
<213> ORGANISM: Artificial Sequence
<220> FEATURE:
<223> OTHER INFORMATION: Synthetic

<400> SEQUENCE: 110

Ser Asp Thr Leu Asp Pro Asn Arg Leu Thr Arg Lys Pro Pro
1               5                   10

<210> SEQ ID NO 111
<211> LENGTH: 14
<212> TYPE: PRT
<213> ORGANISM: Artificial Sequence
<220> FEATURE:
<223> OTHER INFORMATION: Synthetic

<400> SEQUENCE: 111

Ser Asn Thr Leu Asp Pro Asn Arg Leu Thr Arg Lys Pro Pro
1               5                   10

<210> SEQ ID NO 112
<211> LENGTH: 14
<212> TYPE: PRT
<213> ORGANISM: Artificial Sequence
<220> FEATURE:
<223> OTHER INFORMATION: Synthetic

<400> SEQUENCE: 112

-continued

Ser Leu Thr Leu Asp Pro Asn Arg Leu Thr Leu Lys Pro Pro
1               5                   10

<210> SEQ ID NO 113
<211> LENGTH: 14
<212> TYPE: PRT
<213> ORGANISM: Artificial Sequence
<220> FEATURE:
<223> OTHER INFORMATION: Synthetic

<400> SEQUENCE: 113

Ser Leu Thr Asn Asp Pro Asn Arg Arg Thr Leu Lys Pro Pro
1               5                   10

<210> SEQ ID NO 114
<211> LENGTH: 20
<212> TYPE: PRT
<213> ORGANISM: Artificial Sequence
<220> FEATURE:
<223> OTHER INFORMATION: Synthetic

<400> SEQUENCE: 114

Gln Gln Lys Phe Trp Thr Asn Ala Ala Ala Trp Thr Met Gln Lys
1               5                   10                  15

Glu Pro Asn Lys
            20

<210> SEQ ID NO 115
<211> LENGTH: 20
<212> TYPE: PRT
<213> ORGANISM: Artificial Sequence
<220> FEATURE:
<223> OTHER INFORMATION: Synthetic

<400> SEQUENCE: 115

Gln Gln Lys Phe Trp Thr Asn Glu Tyr Tyr Ala Trp Thr Met Gln Lys
1               5                   10                  15

Glu Pro Asn Lys
            20

<210> SEQ ID NO 116
<211> LENGTH: 23
<212> TYPE: PRT
<213> ORGANISM: Artificial Sequence
<220> FEATURE:
<223> OTHER INFORMATION: Synthetic

<400> SEQUENCE: 116

Lys Glu Gln Gln Leu Ser Trp Thr Asn Ala Pro Ala Ala Trp Thr Gln
1               5                   10                  15

Gln Leu Lys Gln Gln Pro Pro
            20

<210> SEQ ID NO 117
<211> LENGTH: 23
<212> TYPE: PRT
<213> ORGANISM: Artificial Sequence
<220> FEATURE:
<223> OTHER INFORMATION: Synthetic

<400> SEQUENCE: 117

Lys Glu Gln Gln Leu Ser Trp Thr Asn Ala Ala Ala Ala Trp Thr Gln
1               5                   10                  15

Gln Leu Lys Gln Gln Pro Pro
            20

```
<210> SEQ ID NO 118
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is selected from the group consisting of R,
      M, E, k, N, K, Q, S, V, L, W, w, q, and A, or is absent, wherein
      lower case letters denote D amino acids and uppercase letters
      denote L amino acids
<220> FEATURE:
<221> NAME/KEY: MISC_FEATURE
<222> LOCATION: (2)..(2)
<223> OTHER INFORMATION: Xaa is selected from the group consisting of G,
      q, E, m, n, w, t, l, A, S, Q, k, and N, wherein lower case letters
      denote D amino acids and uppercase letters denote L amino acids
<220> FEATURE:
<221> NAME/KEY: MISC_FEATURE
<222> LOCATION: (3)..(3)
<223> OTHER INFORMATION: Xaa is selected from the group consisting of E,
      Q, q, N, T, S, l, k, W, and P, wherein lower case letters denote D
      amino acids and uppercase letters denote L amino acids
<220> FEATURE:
<221> NAME/KEY: MISC_FEATURE
<222> LOCATION: (4)..(4)
<223> OTHER INFORMATION: Xaa is selected from the group consisting of q,
      m, M, l, Q, w, K, t, E, i, and a, wherein lower case letters
      denote D amino acids and uppercase letters denote L amino acids
<220> FEATURE:
<221> NAME/KEY: MISC_FEATURE
<222> LOCATION: (5)..(5)
<223> OTHER INFORMATION: Xaa is selected from the group consisting of Q,
      N, E, S, l, L, t, k, w, q, A, W, and G, wherein lower case letters
      denote D amino acids and uppercase letters denote L amino acids
<220> FEATURE:
<221> NAME/KEY: MISC_FEATURE
<222> LOCATION: (6)..(6)
<223> OTHER INFORMATION: Xaa is selected from the group consisting of l,
      G, w, S, i, E, f, and s, wherein lower case letters denote D amino
      acids and uppercase letters denote L amino acids
<220> FEATURE:
<221> NAME/KEY: MISC_FEATURE
<222> LOCATION: (7)..(7)
<223> OTHER INFORMATION: Xaa is selected from the group consisting of S,
      N, T, K, w, M, F, Q, L, k, t, W, l, E, G, I, Y, and D, wherein
      lower case letters denote D amino acids and uppercase letters
      denote L amino acids
<220> FEATURE:
<221> NAME/KEY: MISC_FEATURE
<222> LOCATION: (8)..(8)
<223> OTHER INFORMATION: Xaa is selected from the group consisting of w,
      R, N, T, G, A, n, a, K, q, E, k, L, t, and l, wherein lower case
      letters denote D amino acids and uppercase letters denote L amino
      acids
<220> FEATURE:
<221> NAME/KEY: MISC_FEATURE
<222> LOCATION: (9)..(9)
<223> OTHER INFORMATION: Xaa is selected from the group consisting of T,
      M, k, A, N, P, E, K, D, L, W, w, and Q, wherein lower case letters
      denote D amino acids and uppercase letters denote L amino acids
<220> FEATURE:
<221> NAME/KEY: MISC_FEATURE
<222> LOCATION: (10)..(10)
<223> OTHER INFORMATION: Xaa is selected from the group consisting of N,
      E, S, A, P, Y, T, t, l, V, q, L, H, and M, wherein lower case
      letters denote D amino acids and uppercase letters denote L amino
      acids
<220> FEATURE:
<221> NAME/KEY: MISC_FEATURE
<222> LOCATION: (11)..(11)
<223> OTHER INFORMATION: Xaa is selected from the group consisting of A,
      E, p, n, S, T, L, Q, Y, P, R, W, and N, wherein lower case letters
      denote D amino acids and uppercase letters denote L amino acids
<220> FEATURE:
```

```
<221> NAME/KEY: MISC_FEATURE
<222> LOCATION: (12)..(12)
<223> OTHER INFORMATION: Xaa is selected from the group consisting of A,
      Y, N, M, W, a, D, G, k, q, L, and V, wherein lower case letters
      denote D amino acids and uppercase letters denote L amino acids
<220> FEATURE:
<221> NAME/KEY: MISC_FEATURE
<222> LOCATION: (13)..(13)
<223> OTHER INFORMATION: Xaa is selected from the group consisting of A,
      S, K, L, W, a, I, F, W, M, l, Y, V, R, and Q, or is absent,
      wherein lower case letters denote D amino acids and uppercase
      letters denote L amino acids
<220> FEATURE:
<221> NAME/KEY: MISC_FEATURE
<222> LOCATION: (14)..(14)
<223> OTHER INFORMATION: Xaa is selected from the group consisting of a,
      A, W, N, t, k, f, G, Q, S, l, w, q, T, Y, and E, or is absent,
      wherein lower case letters denote D amino acids and uppercase
      letters denote L amino acids
<220> FEATURE:
<221> NAME/KEY: MISC_FEATURE
<222> LOCATION: (15)..(15)
<223> OTHER INFORMATION: Xaa is selected from the group consisting of q,
      k, Q, w, t, T, W, G, I, M, L, R, and K, or is absent, wherein
      lower case letters denote D amino acids and uppercase letters
      denote L amino acids
<220> FEATURE:
<221> NAME/KEY: MISC_FEATURE
<222> LOCATION: (16)..(16)
<223> OTHER INFORMATION: Xaa is selected from the group consisting of t,
      M, G, q, Q, n, l, K, k, L, T, c, and m, or is absent, wherein
      lower case letters denote D amino acids and uppercase letters
      denote L amino acids
<220> FEATURE:
<221> NAME/KEY: MISC_FEATURE
<222> LOCATION: (17)..(17)
<223> OTHER INFORMATION: Xaa is selected from the group consisting of Q,
      M, n, l, L, q, N, W, T, S, t, k, m, C, K, R, and A, or is absent,
      wherein lower case letters denote D amino acids and uppercase
      letters denote L amino acids
<220> FEATURE:
<221> NAME/KEY: MISC_FEATURE
<222> LOCATION: (18)..(18)
<223> OTHER INFORMATION: Xaa is selected from the group consisting of q,
      n, L, w, k, m, H, D, W, l, Q, E, L, T, S, y, c, and s, or is
      absent; wherein lower case letters denote D amino acids and
      uppercase letters denote L amino acids
<220> FEATURE:
<221> NAME/KEY: MISC_FEATURE
<222> LOCATION: (19)..(19)
<223> OTHER INFORMATION: Xaa is selected from the group consisting of L,
      k, S, Q, K, M, F, q, T, W, r, t, C, N, and V, or is absent;
      wherein lower case letters denote D amino acids and uppercase
      letters denote L amino acids
<220> FEATURE:
<221> NAME/KEY: MISC_FEATURE
<222> LOCATION: (20)..(20)
<223> OTHER INFORMATION: Xaa is selected from the group consisting of k,
      M, T, S, n, c, y, t, N, Q, and q, or is absent; wherein lower case
      letters denote D amino acids and uppercase letters denote L amino
      acids
<220> FEATURE:
<221> NAME/KEY: MISC_FEATURE
<222> LOCATION: (21)..(21)
<223> OTHER INFORMATION: Xaa is selected from the group consisting of Q,
      M, G, W, N, q, T, E, t, k, l, V, C, and L, or is absent; wherein
      lower case letters denote D amino acids and uppercase letters
      denote L amino acids
<220> FEATURE:
<221> NAME/KEY: MISC_FEATURE
<222> LOCATION: (22)..(22)
<223> OTHER INFORMATION: Xaa is selected from the group consisting of G,
      R, Y, H, n, S, C, and Q, or is absent; wherein lower case letters
      denote D amino acids and uppercase letters denote L amino acids
<220> FEATURE:
<221> NAME/KEY: MISC_FEATURE
<222> LOCATION: (23)..(23)
<223> OTHER INFORMATION: Xaa is selected from the group consisting of R,
      M, E, and P, or is absent; wherein lower case letters denote D
``` amino acids and uppercase letters denote L amino acids

<400> SEQUENCE: 118

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 119
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is selected from the group consisting of S,
      q, l, w, e, Q, and k; wherein lower case letters denote D amino
      acids and upper case letters denote L amino acids.
<220> FEATURE:
<221> NAME/KEY: MISC_FEATURE
<222> LOCATION: (2)..(2)
<223> OTHER INFORMATION: Xaa is selected from the group consisting of l,
      Q, W, L, E, d, and n; wherein lower case letters denote D amino
      acids and upper case letters denote L amino acids.
<220> FEATURE:
<221> NAME/KEY: MISC_FEATURE
<222> LOCATION: (3)..(3)
<223> OTHER INFORMATION: Xaa is selected from the group consisting of T,
      k, l, q, and S; wherein lower case letters denote D amino acids
      and upper case letters denote L amino acids.
<220> FEATURE:
<221> NAME/KEY: MISC_FEATURE
<222> LOCATION: (4)..(4)
<223> OTHER INFORMATION: Xaa is selected from the group consisting of l,
      S, Q, w, n, and F; wherein lower case letters denote D amino acids
      and upper case letters denote L amino acids.
<220> FEATURE:
<221> NAME/KEY: MISC_FEATURE
<222> LOCATION: (5)..(5)
<223> OTHER INFORMATION: Xaa is selected from the group consisting of D,
      w, l, and T; wherein lower case letters denote D amino acids and
      upper case letters denote L amino acids.
<220> FEATURE:
<221> NAME/KEY: MISC_FEATURE
<222> LOCATION: (6)..(6)
<223> OTHER INFORMATION: Xaa is selected from the group consisting of p,
      T, S, N, and W, wherein lower case letters denote D amino acids
      and upper case letters denote L amino acids.
<220> FEATURE:
<221> NAME/KEY: MISC_FEATURE
<222> LOCATION: (7)..(7)
<223> OTHER INFORMATION: Xaa is selected from the group consisting of N,
      w, and A, wherein lower case letters denote D amino acids and
      upper case letters denote L amino acids.
<220> FEATURE:
<221> NAME/KEY: MISC_FEATURE
<222> LOCATION: (8)..(8)
<223> OTHER INFORMATION: Xaa is selected from the group consisting of R,
      A, T, and E, wherein lower case letters denote D amino acids and
      upper case letters denote L amino acids.
<220> FEATURE:
<221> NAME/KEY: MISC_FEATURE
<222> LOCATION: (9)..(9)
<223> OTHER INFORMATION: Xaa is selected from the group consisting of l,
      L, A, N, and Y, wherein lower case letters denote D amino acids
      and upper case letters denote L amino acids.
<220> FEATURE:
<221> NAME/KEY: MISC_FEATURE
<222> LOCATION: (10)..(10)
<223> OTHER INFORMATION: Xaa is selected from the group consisting of T,
      t, A, a, S, and Y, wherein lower case letters denote D amino acids
      and upper case letters denote L amino acids.
<220> FEATURE:
<221> NAME/KEY: MISC_FEATURE

```
<222> LOCATION: (11)..(11)
<223> OTHER INFORMATION: Xaa is selected from the group consisting of l,
      L, a, P, A, R, and W, wherein lower case letters denote D amino
      acids and upper case letters denote L amino acids.
<220> FEATURE:
<221> NAME/KEY: MISC_FEATURE
<222> LOCATION: (12)..(12)
<223> OTHER INFORMATION: Xaa is selected from the group consisting of K,
      k, W, A, and t, wherein lower case letters denote D amino acids
      and upper case letters denote L amino acids.
<220> FEATURE:
<221> NAME/KEY: MISC_FEATURE
<222> LOCATION: (13)..(13)
<223> OTHER INFORMATION: Xaa is selected from the group consisting of p,
      t, a, and M, wherein lower case letters denote D amino acids and
      upper case letters denote L amino acids.
<220> FEATURE:
<221> NAME/KEY: MISC_FEATURE
<222> LOCATION: (14)..(14)
<223> OTHER INFORMATION: Xaa is selected from the group consisting of P,
      M, W, q, E, and C, wherein lower case letters denote D amino acids
      and upper case letters denote L amino acids.
<220> FEATURE:
<221> NAME/KEY: MISC_FEATURE
<222> LOCATION: (15)..(15)
<223> OTHER INFORMATION: Xaa is selected from the group consisting of q,
      t, and L, or is absent, wherein lower case letters denote D amino
      acids and upper case letters denote L amino acids.
<220> FEATURE:
<221> NAME/KEY: MISC_FEATURE
<222> LOCATION: (16)..(16)
<223> OTHER INFORMATION: Xaa is selected from the group consisting of L,
      W, Q, P, k, and C, or is absent, wherein lower case letters denote
      D amino acids and upper case letters denote L amino acids.
<220> FEATURE:
<221> NAME/KEY: MISC_FEATURE
<222> LOCATION: (17)..(17)
<223> OTHER INFORMATION: Xaa is selected from the group consisting of k,
      w, l, q, p, P, and E, or is absent, wherein lower case letters
      denote D amino acids and upper case letters denote L amino acids.
<220> FEATURE:
<221> NAME/KEY: MISC_FEATURE
<222> LOCATION: (18)..(18)
<223> OTHER INFORMATION: Xaa is selected from the group consisting of E,
      D, L, p, and P, or is absent, wherein lower case letters denote D
      amino acids and upper case letters denote L amino acids.
<220> FEATURE:
<221> NAME/KEY: MISC_FEATURE
<222> LOCATION: (19)..(19)
<223> OTHER INFORMATION: Xaa is selected from the group consisting of p,
      k, and N, or is absent, wherein lower case letters denote D amino
      acids and upper case letters denote L amino acids.
<220> FEATURE:
<221> NAME/KEY: MISC_FEATURE
<222> LOCATION: (20)..(20)
<223> OTHER INFORMATION: Xaa is selected from the group consisting of N,
      Q, and K, or is absent, wherein lower case letters denote D amino
      acids and upper case letters denote L amino acids.
<220> FEATURE:
<221> NAME/KEY: MISC_FEATURE
<222> LOCATION: (21)..(21)
<223> OTHER INFORMATION: Xaa is selected from the group consisting of K,
      R, and q, or is absent, wherein lower case letters denote D amino
      acids and upper case letters denote L amino acids.
<220> FEATURE:
<221> NAME/KEY: MISC_FEATURE
<222> LOCATION: (22)..(22)
<223> OTHER INFORMATION: Xaa is selected from the group consisting of P
      or is absent, wherein lower case letters denote D amino acids and
      upper case letters denote L amino acids.
<220> FEATURE:
<221> NAME/KEY: MISC_FEATURE
<222> LOCATION: (23)..(23)
<223> OTHER INFORMATION: Xaa is selected from the group consisting of p
      or is absent, wherein lower case letters denote D amino acids and
      upper case letters denote L amino acids.

<400> SEQUENCE: 119
```

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20
```

<210> SEQ ID NO 120
<211> LENGTH: 14
<212> TYPE: PRT
<213> ORGANISM: Artificial Sequence
<220> FEATURE:
<223> OTHER INFORMATION: Synthetic

<400> SEQUENCE: 120

```
Ser Leu Thr Leu Asp Pro Asn Arg Leu Thr Leu Lys Pro Pro
1               5                   10
```

<210> SEQ ID NO 121
<211> LENGTH: 14
<212> TYPE: PRT
<213> ORGANISM: Artificial Sequence
<220> FEATURE:
<223> OTHER INFORMATION: Synthetic

<400> SEQUENCE: 121

```
Ser Leu Thr Leu Asp Pro Asn Arg Leu Thr Leu Lys Pro Pro
1               5                   10
```

<210> SEQ ID NO 122
<211> LENGTH: 18
<212> TYPE: PRT
<213> ORGANISM: Artificial Sequence
<220> FEATURE:
<223> OTHER INFORMATION: Synthetic

<400> SEQUENCE: 122

```
Gln Leu Ser Asn Thr Trp Ala Ala Ala Trp Thr Met Gln Leu Lys
1               5                   10                  15

Pro Pro
```

<210> SEQ ID NO 123
<211> LENGTH: 20
<212> TYPE: PRT
<213> ORGANISM: Artificial Sequence
<220> FEATURE:
<223> OTHER INFORMATION: Synthetic

<400> SEQUENCE: 123

```
Gln Gln Lys Ser Trp Thr Asn Glu Tyr Tyr Ala Trp Thr Met Gln Leu
1               5                   10                  15

Glu Pro Asn Lys
            20
```

<210> SEQ ID NO 124
<211> LENGTH: 19
<212> TYPE: PRT
<213> ORGANISM: Artificial Sequence
<220> FEATURE:
<223> OTHER INFORMATION: Synthetic

<400> SEQUENCE: 124

```
Gln Gln Leu Ser Trp Thr Asn Ala Ala Ala Ala Trp Thr Met Gln Leu
1               5                   10                  15

Lys Pro Pro
```

-continued

<210> SEQ ID NO 125
<211> LENGTH: 14
<212> TYPE: PRT
<213> ORGANISM: Artificial Sequence
<220> FEATURE:
<223> OTHER INFORMATION: Synthetic

<400> SEQUENCE: 125

Ser Leu Thr Asn Asp Pro Asn Arg Arg Thr Leu Lys Pro Pro
1               5                   10

<210> SEQ ID NO 126
<211> LENGTH: 23
<212> TYPE: PRT
<213> ORGANISM: Artificial Sequence
<220> FEATURE:
<223> OTHER INFORMATION: Synthetic

<400> SEQUENCE: 126

Arg Gly Glu Met Asn Leu Ser Trp Met Asn Glu Tyr Ser Ala Trp Thr
1               5                   10                  15

Met Asn Leu Lys Met Gly Arg
            20

<210> SEQ ID NO 127
<211> LENGTH: 22
<212> TYPE: PRT
<213> ORGANISM: Artificial Sequence
<220> FEATURE:
<223> OTHER INFORMATION: Synthetic

<400> SEQUENCE: 127

Arg Gly Glu Met Asn Leu Ser Trp Met Glu Pro Asn Lys Trp Thr Met
1               5                   10                  15

Asn Leu Lys Met Gly Arg
            20

<210> SEQ ID NO 128
<211> LENGTH: 23
<212> TYPE: PRT
<213> ORGANISM: Artificial Sequence
<220> FEATURE:
<223> OTHER INFORMATION: Synthetic

<400> SEQUENCE: 128

Met Gly Glu Met Glu Gly Asn Arg Lys Ser Asn Met Leu Asn Arg Gly
1               5                   10                  15

Leu Trp Ser Thr Trp Tyr Met
            20

<210> SEQ ID NO 129
<211> LENGTH: 17
<212> TYPE: PRT
<213> ORGANISM: Artificial Sequence
<220> FEATURE:
<223> OTHER INFORMATION: Synthetic

<400> SEQUENCE: 129

Gln Gln Leu Ser Trp Thr Asn Ala Ala Ala Ala Trp Thr Gln Gln Leu
1               5                   10                  15

Lys

<210> SEQ ID NO 130
<211> LENGTH: 19
<212> TYPE: PRT

```
<213> ORGANISM: Artificial Sequence
<220> FEATURE:
<223> OTHER INFORMATION: Synthetic

<400> SEQUENCE: 130

Asn Met Asn Leu Ser Leu Met Ala Ala Ala Ala Leu Thr Met Asn
1               5                   10                  15

Leu Gln Met

<210> SEQ ID NO 131
<211> LENGTH: 22
<212> TYPE: PRT
<213> ORGANISM: Artificial Sequence
<220> FEATURE:
<223> OTHER INFORMATION: Synthetic

<400> SEQUENCE: 131

Arg Gly Glu Met Asn Tyr Phe Trp Met Asn Glu Tyr Tyr Gly Trp Thr
1               5                   10                  15

Met Asn Lys Met Gly Arg
            20

<210> SEQ ID NO 132
<211> LENGTH: 19
<212> TYPE: PRT
<213> ORGANISM: Artificial Sequence
<220> FEATURE:
<223> OTHER INFORMATION: Synthetic

<400> SEQUENCE: 132

Val Ala Leu Lys Leu His Lys Asn Glu Tyr Tyr Gly Val Ala Leu Lys
1               5                   10                  15

Leu His Lys

<210> SEQ ID NO 133
<211> LENGTH: 19
<212> TYPE: PRT
<213> ORGANISM: Artificial Sequence
<220> FEATURE:
<223> OTHER INFORMATION: Synthetic

<400> SEQUENCE: 133

Leu Ala Leu Lys Ser Asp Phe Asn Glu Tyr Tyr Gly Leu Ala Leu Lys
1               5                   10                  15

Ser Asp Phe

<210> SEQ ID NO 134
<211> LENGTH: 21
<212> TYPE: PRT
<213> ORGANISM: Artificial Sequence
<220> FEATURE:
<223> OTHER INFORMATION: Synthetic

<400> SEQUENCE: 134

Gln Trp Glu Gln Ser Leu Gln Lys Asn Ala Pro Ala Ala Lys Gln Leu
1               5                   10                  15

Thr Trp Gln Gln Thr
            20

<210> SEQ ID NO 135
<211> LENGTH: 21
<212> TYPE: PRT
<213> ORGANISM: Artificial Sequence
<220> FEATURE:
```

```
<223> OTHER INFORMATION: Synthetic

<400> SEQUENCE: 135

Trp Ser Gln Gln Thr Gln Leu Trp Asn Ala Pro Ala Ala Gln Gln Lys
1               5                   10                  15

Lys Leu Gln Thr Glu
            20

<210> SEQ ID NO 136
<211> LENGTH: 21
<212> TYPE: PRT
<213> ORGANISM: Artificial Sequence
<220> FEATURE:
<223> OTHER INFORMATION: Synthetic

<400> SEQUENCE: 136

Gln Gln Glu Thr Lys Trp Lys Thr Asn Ala Pro Ala Ala Ser Gln Leu
1               5                   10                  15

Leu Gln Gln Gln Trp
            20

<210> SEQ ID NO 137
<211> LENGTH: 21
<212> TYPE: PRT
<213> ORGANISM: Artificial Sequence
<220> FEATURE:
<223> OTHER INFORMATION: Synthetic

<400> SEQUENCE: 137

Trp Gln Glu Thr Leu Leu Gln Gln Asn Ala Pro Ala Ala Lys Gln Gln
1               5                   10                  15

Lys Trp Gln Ser Thr
            20

<210> SEQ ID NO 138
<211> LENGTH: 21
<212> TYPE: PRT
<213> ORGANISM: Artificial Sequence
<220> FEATURE:
<223> OTHER INFORMATION: Synthetic

<400> SEQUENCE: 138

Lys Gln Gln Trp Trp Gln Thr Thr Asn Ala Pro Ala Ala Leu Lys Gln
1               5                   10                  15

Leu Glu Gln Ser Gln
            20

<210> SEQ ID NO 139
<211> LENGTH: 21
<212> TYPE: PRT
<213> ORGANISM: Artificial Sequence
<220> FEATURE:
<223> OTHER INFORMATION: Synthetic

<400> SEQUENCE: 139

Gln Lys Glu Trp Gln Trp Ser Gln Asn Ala Pro Ala Ala Leu Gln Gln
1               5                   10                  15

Gln Leu Thr Lys Thr
            20

<210> SEQ ID NO 140
<211> LENGTH: 21
<212> TYPE: PRT
<213> ORGANISM: Artificial Sequence
```

-continued

```
<220> FEATURE:
<223> OTHER INFORMATION: Synthetic

<400> SEQUENCE: 140

Ser Gln Leu Thr Gln Gln Lys Thr Asn Ala Pro Ala Ala Trp Gln Leu
1               5                   10                  15

Trp Glu Gln Gln Lys
            20

<210> SEQ ID NO 141
<211> LENGTH: 21
<212> TYPE: PRT
<213> ORGANISM: Artificial Sequence
<220> FEATURE:
<223> OTHER INFORMATION: Synthetic

<400> SEQUENCE: 141

Gln Thr Lys Gln Ser Trp Trp Glu Asn Ala Pro Ala Ala Gln Gln Thr
1               5                   10                  15

Leu Gln Gln Lys Leu
            20

<210> SEQ ID NO 142
<211> LENGTH: 21
<212> TYPE: PRT
<213> ORGANISM: Artificial Sequence
<220> FEATURE:
<223> OTHER INFORMATION: Synthetic

<400> SEQUENCE: 142

Lys Leu Gln Thr Glu Gln Trp Gln Asn Ala Pro Ala Ala Ser Gln Leu
1               5                   10                  15

Lys Gln Trp Thr Gln
            20

<210> SEQ ID NO 143
<211> LENGTH: 21
<212> TYPE: PRT
<213> ORGANISM: Artificial Sequence
<220> FEATURE:
<223> OTHER INFORMATION: Synthetic

<400> SEQUENCE: 143

Gln Glu Trp Gln Leu Gln Leu Lys Asn Ala Pro Ala Ala Gln Trp Gln
1               5                   10                  15

Lys Thr Ser Thr Gln
            20

<210> SEQ ID NO 144
<211> LENGTH: 21
<212> TYPE: PRT
<213> ORGANISM: Artificial Sequence
<220> FEATURE:
<223> OTHER INFORMATION: Synthetic

<400> SEQUENCE: 144

Leu Leu Gln Gln Gln Lys Glu Trp Asn Ala Pro Ala Ala Gln Thr Lys
1               5                   10                  15

Gln Ser Thr Gln Trp
            20

<210> SEQ ID NO 145
<211> LENGTH: 21
<212> TYPE: PRT
```

<213> ORGANISM: Artificial Sequence
<220> FEATURE:
<223> OTHER INFORMATION: Synthetic

<400> SEQUENCE: 145

Gln Gln Glu Trp Ser Gln Leu Lys Asn Ala Pro Ala Ala Gln Trp Lys
1               5                   10                  15
Leu Gln Thr Gln Thr
            20

<210> SEQ ID NO 146
<211> LENGTH: 21
<212> TYPE: PRT
<213> ORGANISM: Artificial Sequence
<220> FEATURE:
<223> OTHER INFORMATION: Synthetic

<400> SEQUENCE: 146

Lys Gln Gln Gln Trp Glu Gln Leu Asn Ala Pro Ala Ala Thr Lys Leu
1               5                   10                  15
Gln Gln Thr Ser Trp
            20

<210> SEQ ID NO 147
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION-optional

<400> SEQUENCE: 147

Met Asn Trp Glu Ser Lys Gly Glu Trp Leu Arg Met Arg Tyr Gly Thr
1               5                   10                  15
Met Leu Ser Asn Gly Asn Met
            20

<210> SEQ ID NO 148
<211> LENGTH: 12
<212> TYPE: PRT
<213> ORGANISM: Artificial Sequence
<220> FEATURE:
<223> OTHER INFORMATION: Synthetic

<400> SEQUENCE: 148

Gln Gln Gln Gln Glu Pro Asn Lys Gln Gln Gln Gln
1               5                   10

<210> SEQ ID NO 149
<211> LENGTH: 23
<212> TYPE: PRT
<213> ORGANISM: Artificial Sequence
<220> FEATURE:
<223> OTHER INFORMATION: Synthetic

<400> SEQUENCE: 149

Arg Gly Glu Ala Trp Met Tyr Leu Lys Asn Asn Leu Ser Glu Thr Met
1               5                   10                  15
Met Ser Asn Met Trp Gly Arg
            20

<210> SEQ ID NO 150

```
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION-optional

<400> SEQUENCE: 150

Arg Gly Glu Met Asn Tyr Phe Trp Met Asn Glu Tyr Tyr Gly Trp Thr
1               5                   10                  15

Met Asn Cys Lys Met Gly Arg
            20

<210> SEQ ID NO 151

<400> SEQUENCE: 151

000

<210> SEQ ID NO 152
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION-optional

<400> SEQUENCE: 152

Ala Gln Gln Ile Glu Cys Leu Thr Asn Val Trp Asp Lys Glu Leu Thr
1               5                   10                  15

Met Tyr Phe Asn Val Ser Glu
            20

<210> SEQ ID NO 153
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION-optional

<400> SEQUENCE: 153

Trp Arg Pro Trp Ala Ile Asp Gln Met Asn Thr Val Lys Gln Arg Lys
1               5                   10                  15

Ala Ser Val Tyr Leu Gln Pro
            20

<210> SEQ ID NO 154
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 154
```

Lys Leu Lys Pro Leu Leu Thr Ser Glu Asn Thr Leu
1               5                   10

<210> SEQ ID NO 155
<211> LENGTH: 12
<212> TYPE: PRT
<213> ORGANISM: Artificial Sequence
<220> FEATURE:
<223> OTHER INFORMATION: Synthetic

<400> SEQUENCE: 155

Ser Trp Thr Trp Glu Pro Asn Lys Trp Thr Trp Lys
1               5                   10

<210> SEQ ID NO 156
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 156

Ser Leu Thr Leu Glu Pro Asn Lys Leu Thr Leu Lys
1               5                   10

<210> SEQ ID NO 157
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 157

Val Ala Leu Lys Leu Asp Lys Asn Glu Tyr Tyr Gly Val Ala Leu Lys
1               5                   10                  15

Leu Asp Lys

<210> SEQ ID NO 158
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 158

Arg Gly Glu Met Asn Ile Ser Trp Met Asn Glu Tyr Ser Gly Trp Thr
1               5                   10                  15

Met Asn Leu Lys Met Gly Arg
            20